US007094873B1

(12) United States Patent
Patterson et al.

(10) Patent No.: US 7,094,873 B1
(45) Date of Patent: Aug. 22, 2006

(54) POLYPEPTIDE THAT INTERACTS WITH HEAT SHOCK PROTEINS

(75) Inventors: Winston Campbell Patterson, Chapel Hill, NC (US); Carol A. Ballinger, Santa Fe, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/573,473

(22) Filed: May 17, 2000

Related U.S. Application Data

(60) Provisional application No. 60/134,433, filed on May 17, 1999.

(51) Int. Cl.
*C07K 14/00* (2006.01)

(52) U.S. Cl. ..................................... 530/350; 536/23.5
(58) Field of Classification Search ............... 536/23.5; 530/350
See application file for complete search history.

(56) References Cited

U.S. PATENT DOCUMENTS

| | | | |
|---|---|---|---|
| 4,436,815 A | 3/1984 | Hershberger et al. | |
| 4,440,859 A | 4/1984 | Rutter et al. | |
| 6,043,084 A * | 3/2000 | Scanlan et al. ........... | 435/252.3 |
| 6,165,767 A * | 12/2000 | Lal et al. ..................... | 435/196 |
| 6,218,521 B1 * | 4/2001 | Obata ......................... | 536/23.1 |
| 6,338,952 B1 | 1/2002 | Young | |

FOREIGN PATENT DOCUMENTS

WO    WO-9904265 A2 *  1/1999

OTHER PUBLICATIONS

Yang, X, et al, 1998, Human BAG-1/RAP46 protein is generated as four isoforms by alternative initiation and overexpressed in cancer cells, Oncogene, vol. 17, No. 8, pp. 981-989.*
Takayama, S. et al, 1995, Cloning and functional analysis of BAG-1: a novel Bcl-2 binding protein with anti-cell death activity. Cell, vol. 80, No. 2, pp. 279-284.*
Froesch, BA, et al, 1998, BAG-1L protein enhances androgen receptor function, Journal of Biological Chemistry, vol. 273, No. 19, pp. 11660-11666.*
Cato, ACB, et al, 2001, BAG-1 family of cochaperones in the modulation of nuclear receptor action, Journal of Steroid Biochemistry & Molecular Biology, vol. 78, No. 5, pp. 379-388.*
Prapapanich, V, et al, 1996, Mutational analysis of the hsp-70-interacting protein Hip, Molecular and Cellular Biology, vol. 16, No. 11, pp. 6200-6207.*
Jiang, J., et al, 2001, CHIP is a U-box-dependent E3 ubiquitin ligase, Journal of Biological Chemistry, vol. 276, No. 46, pp. 42938-42944.*
Prapapanich, V, et al, 1998, Mutation of Hip's carboxyl-terminal region inhibits a transitional stage of progesterone receptor assembly, Molecular and Cellular Biology, vol. 18, No. 2, pp. 944-952.*
Bork, P, 2000, Powers and pitfalls in sequence analysis: the 70% hurdle, Genome Research, vol. 10, pp. 398-400.*

Burgess, WH, et al, 1990, Possible dissociation of the heparin-binding and mitogenic activities of heparin-binding (acidic fibroblast) growth factor-1, J Cell Biology, vol. 111, pp. 2129-2138.*
Lazar, E, et al, 1988, Transforming growth factor alpha: mutation of aspartic acid 47 and leucine 48 results in different biological activities, Molecular and Cellular Biology, vol. 8, pp. 1247-1252.*
Bowie, JU, et al, 1990, Deciphering the message in protein sequences: tolerance to amino acid substitutions, Science, vol. 247, pp. 1306-1310.*
Scanlan, MJ, Direct Submission, Dec. 23, 1997, Database GenBank Accession No. AF039689, *Homo sapiens* antigen NY-CO-7 (NY-CO-7) mRNA, complete cds.*
Gura T. Science Nov. 7, 1997; 278: 1040-1.*
Bergers G, et al. Cur Opin Genetics Develop 2000; 10: 120-7.*
Skolnick, J, et al. Trends Biotechnol Jan. 2000; 18: 34-9.*
De Plaen E, et al. Immunogenetics. 1994; 40: 360-9.*
Tockman MS, et al. Cancer Res. 1992; 52 (Suppl.): 2711s-2718s.*
Ward AM. Developmental Oncol. 1985; 21: 90-106.*
Goebl M, et al. Trends Biochem Sci. May 1991;16 (5): 173-7.*
Murata S, et al. EMBO Rep. Dec. 2001;2 (12): 1133-8.*
Nickolay R, et al. J biol Chem. Jan. 23, 2004; 279 (4): 2673-8.*
Murata S, et al. Int J Biochem Cell Biol. 2003; 35: 572-8.*
Kampringa et al. (Mol. Cell. Biol. Jul. 2003; 23 (14): 4948-4958).*
Luque et al. (Biochemistry. Nov. 19, 2002; 41 (46): 13663-13671.*
Vucic et al. (J. Biol. Chem. Dec. 18, 1998; 273 (51): 33915-33921).*
Takada et al. (Mol. Endocrinol. 2000; 14 (5): 733-740).*
Guo et al. (Proc. Natl. Acad. Sci. USA. Jun. 22, 2004; 101 ;(25): 9205-9210).*
Ballinger et al., "p35 is a Novel Protein Highly Expressed in Striated Muscle that Interacts with Members of the Heat Shock Protein Family," Abstract 643, 71st Annual Meeting of the American Heart Association, Nov. 8-11, Dallas, *Supplement to Circulation*,*98*(17):125 (Oct. 27, 1998).
Ballinger et al., "Identification of CHIP, a Novel Striated Muscle-Restricted TPR-Containing Protein that Negatively Regulates Chaperone Functions," Abstract 370.7 and Poster, Annual Meeting of Professional Research Scientists and American Association of Anatomists, Experimental Biology '99, Apr. 17-21, Washington, D.C., *The FASEB Journal*, *13*(4):A442, (Mar. 12, 1999).
Ballinger et al., "Identification of CHIP, a Novel Tetratricopeptide Repeat-Containing Protein That Interacts with Heat Shock Proteins and Negatively Regulates Chaperone Functions," *Molecular and Cellular Biology*, *19*(6):4535-4545 (Jun. 1999; available on line May 17, 1999).

(Continued)

*Primary Examiner*—Stephen L. Rawlings
(74) *Attorney, Agent, or Firm*—Mueting, Raasch & Gebhardt, P.A.

(57) ABSTRACT

An isolated polypeptide having negative regulating activity for a heat shock protein is provided. Also provided is an isolated nucleic acid encoding the polypeptide of the invention, methods for identifying inhibitors of the polypeptide and recombinant preparation of the polypeptide. Also provided are compositions such as inhibitor compositions.

12 Claims, 15 Drawing Sheets

OTHER PUBLICATIONS

Ballinger et al., "Ubiquitylation of HSC70 is Mediated by CHIP, a Novel Ubiquitylation Factor," Abstract and oral presentation, Cold Spring Harbor Meeting on Molecular Chaperones & Heat Shock Response, May 3-7, Cold Spring Harbor, N.Y. (May 4, 2000).

Barr et al., "7-Deaza-2'-Deoxyguanosine-5'-Triphosphate: Enhanced Resolution in M13 Dideoxy Sequencing," *BioTechniques*, 4(5):428-432 (1986).

Baumann et al., "Dexamethasone Regulates the Program of Secretory Glycoprotein Synthesis in Hepatoma Tissue Culture Cells," *The Journal of Cellular Biology*, 85:1-8 (1980).

Benaroudj et al., "The COOH-terminal Peptide Binding Domain Is Essential for Self-association of the Molecular Chaperone HSC70," *The Journal of Biological Chemistry*, 272(13):8744-8751 (1997).

"BLAST," National Institutes of Health [online] United States, [retrieved Oct. 23, 2000]. Retrived from the Internet.

Boice et al., "A Mutational Study of the Peptide-binding Domain of Hsc70 Guided by Secondary Structure Prediction," *The Journal of Biological Chemistry*, 272(40):24825-24831 (1997).

Braun et al., "The base of the proteasome regulatory particle exhibits chaperone-like activity," *Nature Cell Biology*, 1:221-226 (Aug. 1999).

Broach, "[21] Construction of High Copy Yeast Vectors Using 2-μm Circle Sequences," *Methods in Enzymology: vol. 101 Recombinant DNA*, pp. 307-325 (1983).

Carrello et al., "The Common Tetratricopeptide Repeat Acceptor Site for Steroid Receptor-associated Immunophilins and Hop Is Located in the Dimerization Domain of Hsp90," *The Journal of Biological Chemistry*, 274(5):2682-2689 (Jan. 29, 1999).

Chakrabarti et al., "Vaccina Virus Expression Vector: Coexpression of β-Galactosidase Provides Visual Screening of Recombinant Virus Plaques," *Molecular and Cellular Biology*, 5(12):3403-3409 (1985).

Chappell et al., "The ATPase Core of a Clathrin Uncoating Protein," *The Journal of Biological Chemistry*, 262(2):746-751 (1987).

Chen et al., "Interactions of p60, a Mediator of Progesterone Receptor Assembly, with Heat Shock Proteins Hsp90 and Hsp70," *Molecular Endocrinology*, 10(6):682-693 (1996).

Clewell et al., "Supercoiled Circular DNA-Protein Complex in *Escherichia coli*: Purification and Induced Conversion to an Open Circular DNA Form," *Proceedings of the National Academy of Sciences USA*, 62:1159-1166 (1969).

Clewell, "Nature of Col $E_1$ Plasmid Replication in *Escherichia coli* in the Presence of Chlorampenicol," *Journal of Bacteriology*, 110(2):667-676 (1972).

Cohen et al., "Nonchromosomal Antibiotic Resistance in Bacteria: Genetic Transformation of *Escherichia coli* by R-Factor DNA," *Proceedings of the National Academy of Sciences USA*, 69(8):2110-2114 (1972).

Connell et al., "CHIP's Interaction with HSP90 Regulates Glucocorticoid Receptor Function and Degradation," Abstract and poster, Cold Spring Harbor Meeting on Molecular Chaperones & Heat Shock Response, May 3-7, Cold Spring Harbor, N.Y., 25 pages (May 4, 2000).

Connell et al., "The co-chaperone CHIP regulates protein triage decisions mediated by heat shock proteins," *Nature Cell Biology*, 3(1):93-96 (2001).

Das et al., "The structure of the tetratricopeptide repeats of protein phosphatase 5: implications for TPR-mediated protein-protein interactions," *The EMBO Journal*, 17(5):1192-1199 (1998).

De Boer et al., "The *tac* promoter: A functional hybrid derived from the *trp* and *lac* promoters," *Proceedings of the National Academy of Sciences USA*, 80:21-25 (1983).

Demand et al., "The Carboxy-Terminal Domain of Hsc70 Provides Binding Sites for a Distinct Set of Chaperone Cofactors," *Molecular and Cellular Biology*, 18(4):2023-2028 (1998).

Deuerling et al., "Trigger factor and DnaK cooperate in folding of newly synthesized proteins," *Nature*, 400:693-696 (Aug. 12, 1999).

Dittmar et al., "Folding of the Glucocorticoid Receptor by the Reconstituted hsp90-based Chaperone Machinery," *The Journal of Biological Chemistry*, 272(20):13047-13054 (1997).

Dubiel et al., "Molecular cloning and expression of subunit 12: a non-MCP and non-ATPase subunit of the 26 S protease," *FEBS Letters*, 363:97-100 (1995).

Ellis, "The "Bio" in Biochemistry: Protein Folding Inside and Outside the Cell," *Science*, 272:1448-1449 (1996).

Fiers et al., "Complete nucleotide sequence of SV40 DNA," *Nature*, 273(5658):113-120 (1978).

Frydman et al., "Folding of nascent polypeptide chains in a high molecular mass assembly with molecular chaperones," *Nature*, 370:111-117 (1994).

Frydman et al., "Principles of Chaperone-Assisted Protein Folding: Differences Between in Vitro and in Vivo Mechanisms," *Science*, 272:1497-1502 (1996).

"GenomeNet WWW server," Institute for Chemical Research, Kyoto University [online]. Kyoto, Japan, updated Oct. 14, 2000 [retrieved Oct. 23, 2000]. Retrieved from the Internet: <URL: http://www.genome.ad.jp/SIT/CLUSTALW.html>, 2 pages.

Goebl et al., "The TPR snap helix: a novel protein repeat motif from mitosis to transcription," *Trends in Biochemical Sciences*, 16(5):173-177 (1991).

Goeddel et al., "Synthesis of human fibroblast interferon by *E. coli,*" *Nucleic Acids Research*, 8(18):4057-4074 1980).

Graham et a., "A New Technique for the Assay of Infectivity of Human Adenovirus 5 DNA," *Virology*, 52:456-467 (1973).

Gyuris et al., "Cdi1, a Human G1 and S Phase Protein Phosphatase That Associates with Cdk2," *Cell*, 75:791-803 (1993).

Harlow et al., *Antibodies; a Laboratory Manual*, Cold Spring Harbor Laboratory Press, Cold Spring Harbor, NY, Title page, publication page, and table of contents only, 9 pages (1988).

Hartl, "Molecular chaperones in cellular protein folding," *Nature*, 381:571-579 1996.

Hinnen et al., "Transformation of yeast," *Proceedings of the National Academy of Sciences USA*, 75(4):1929-1933 (1978).

Hirano et al., "Snap Helix with Knob and Hole: Essential Repeats in S. pombe Nuclear Protein $nuc2^{+,\ Cell,\ 60}$:319-328 (1990).

Hitzeman et al., "Isolation and Characterization of the Yeast 3-Phosphoglycerokinase Gene (PGK) by an Immunological Screening Technique," *The Journal of Biological Chemistry*, 255(24):12073-12080 (1980).

Höhfeld et al., "Hip, a Novel Cochaperone Involved in the Eukaryotic Hsc70/hsp40 Reaction Cycle," *Cell*, 83:589-598 (1995).

Höhfeld et al., "GrpE-like regulation of the Hsc70 chaperone by the anit-apoptotic protein BAG-1," *The EMBO Journal*, 16(20):6209-6216 (1997).

Höhfeld, "Regulation of the Heat Schock Cognate Hsc70 in the Mammalian Cell: The Characterization of the Anti-Apoptotic Protein BAG-1 Provides Novel Insights," *Biological Chemistry*, 379:269-274 (1998).

Holland et al., "The Primary Structures of Two Yeast Enolase Genes," *The Journal of Biological Chemistry*, 256(3):1385-1395 (1981).

Irmer et al., "Characterization of Functional Domains of the Eukaryotic Co-chaperone Hip," *The Journal of Biological Chemistry*, 272(4):2230-2235 (1997).

Johnson et al., "Characterization of a Novel 23-Kilodalton Protein of Unactive Progesterone Receptor Complexes," *Molecular and Cellular Biology*, 14(3):1956-1963 (1994).

Johnson et al., "A Proteolytic Pathway That Recognizes Ubiquitin as a Degradation Signal," *The Journal of Biological Chemistry*, 270(29):17442-17456 (1995).

Kay, "Structure-function relationships in the FK506-binding protein (FKBP) family of peptidylprolyl *cis-trans* isomerases," *B iochemical Journal*, 314:361-385 (1996).

Kieffer et al., "Cyclophilin-40, a Protein with Homology to the P59 Component of the Steroid Receptor Complex," *The Journal of Biological Chemistry*, 268(17):12303-12310 (1993).

Koegl et al., "A Novel Ubiquitination Factor, E4, Is Involved in Multiubiquitin Chain Assembly," *Cell*, 96:635-644 (Mar. 5, 1999).

Lamb et al., "Tetratrico peptide repeat interactions: to TPR or not to TPR?" *Trends in Biochemical Sciences*, 20:257-259 (1995).

Lee et al., "Selective Inhibitors of the Proteasome-dependent and Vacuolar Pathways of Protein Degradation in *Saccharomyces cerevisiae*," *The Journal of Biological Chemistry*, 271(44):27280-27284 (1996).

Liberek et al., "*Escherichia coli* DnaJ and GrpE heat shock proteins jointly stimulate ATPase activity of DnaK," *Proceedings of the National Academy of Sciences USA*, 88:2874-2878 (1991).

Lu et al., "The Conserved Carboxyl Terminus and Zinc Finger-like Domain of the Co-chaperone Ydj1 Assist Hsp70 in Protein Folding," *The Journal of Biological Chemistry, 273*;(10):5970-5978 (1998).

Luckow et al., "High Level Expression of Nonfused Foreign Genes with *Autographa californica* Nuclear Polyhedrosis Virus Expression Vectors," *Virology, 170*:31-39 (1989).

Lüders et al., "Cofactor-Induced Modulation of the Functional Specificity of the Molecular Chaperone Hsc70," *Biological Chemistry, 379*:1217-1226 (1998).

Mackett et al., "General Method for Production and Selection of Infectious Vaccinia Virus Recombinants Expressing Foreign Genes," *Journal of Virology, 49*(3):857-864 (1984).

Maheswaran et al., "Inhibition of cellular proliferation by the Wilms tumor suppressor WT1 requires association with the inducible chaperone Hsp70," *Genes & Development, 12*:1108-1120 (1998).

Mather, "Establishment and Characterization of Two Distinct Mouse Testicular Epithelial Cell Lines," *Biology of Reproduction, 23*:243-252 (1980).

Mather et al., "Culture of Testicular Cells in Hormone-Supplemented Serum-Free Medium," *Annals of the New York Academy of Sciences, 383*:44-68 (1982).

Maxam et al., "[57] Sequencing End-Labeled DNA with Base-Specific Chemical Cleavages," *Methods in Enzymology, vol. 65, Nucleic Acids Part I*, pp. 499-590 (1980).

Meacham et al., "The Hc70 co-chaperone CHIP targets immature CFTR for proteasomal degradation," *Nature Cell Biology, 3*(1):100-105 (2001).

Messing et al., "A system for shotgun DNA sequencing," *Nucleic Acids. Research, 9*(2):309-321 (1981).

Minami et al., "Regulation of the Heat-shock Protein 70 Reaction Cycle by the Mammalian DnaJ Homolog, Hsp40," *The Journal of Biological Chemistry, 271*(32):19617-19624 1996).

Morimoto, "Regulation of the heat shock transcriptional response: cross talk between a family of heat shock factors, molecular chaperones, and negative regulators," *Gene & Development, 12*:3788-3496 (1998).

Moss, "Vaccinia Virus Expression Vectors," *Gene Transfer Vectors for Mammalian Cells*, Miller et al., eds., Cold Spring Harbor Laboratory Press, Cold Spring Harbor, NY, Title page, publication page, table of contents, and pp. 10-14 (1987).

Nair et al., "Molecular Cloning of Human FKBP51 and Comparisons of Immunophilin Interactions with Hsp90 and Progesterone Receptor," *Molecular and Cellular Biology, 17*(2):594-603 (1997).

National Center for Biotechnology Information, National Library of Medicine, National Institutes of Health, GenBank Locus HUMHSP70D, Accession No. M11717 M15432, "Human heat shock protein (hsp 70) gene," [online]. Bethesda, MD [retrieved on Oct. 24, 2000]. Retrived from the Internet.

National Center for Biotechnology Information, National Library of Medicine, National Institutes of Health, GenBank Locus HSHSC70, Accession No. Y00371, "Human hsc 70 gene for 71 kd heat shock cognate protein," [online]. Bethesda, MD [retrieved on Oct. 24, 2000]. Retrived from the Internet.

National Center for Biotechnology Information, National Library of Medicine, National Institutes of Health, GenBank Locus CVU57443, Accession No. U57443, "Cloning vector pODB8, GAL4 DNA-binding domain vector, complete sequence," [online]. Bethesda, MD [retrieved on Jan. 25, 2001]. Retrieved from the Internet.

National Center for Biotechnology Information, National Library of Medicine, National Institutes of Health, GenBank Locus MMU20344, Accession No. U20344, "Mus musculus gut-enriched Kruppel-like factor GKLF mRNA," [online]. Bethesda, MD [retrieved on Nov. 3, 2000]. Retrieved from the Internet.

National Center for Biotechnology Information, National Library of Medicine, National Institutes of Health, GenBank Locus AF039689, Accession No. AF039689, "*Homo sapiens* antigen NY-CO-7 (NY-CO-7) mRNA," [online]. Bethesda, MD [retrieved on Oct. 24, 2000]. Retrieved from the Internet.

National Center for Biotechnology Information, National Library of Medicine, National Institutes of Health, GenBank Locus AF129084, Accession No. AF129084, "*Drosophila melanogaster* carboxy terminus of Hsp70-interacting protein (CHIP) mRNA," [online]. Bethesda, MD [retrieved on Oct. 24, 2000]. Retrieved from the Internet.

National Center for Biotechnology Information, National Library of Medicine, National Institutes of Health, GenBank Locus AF129085, Accession No. AF129085, "*Homo sapiens* carboxy terminus of Hsp70-interacting protein (CHIP) mRNA," [online]. Bethesda, MD [retrieved on Oct. 24, 2000]. Retrieved from the Internet.

National Center for Biotechnology Information, National Library of Medicine, National Institutes of Health, GenBank Locus AF129086, Accession No. AF129086, "*Mus musculus* carboxy terminus of Hsp7-interacting protein (Chip) mRNA," [online]. Bethesda, MD [retrieved on Oct. 24, 2000]. Retrieved from the Internet.

National Center for Biotechnology Information, National Library of Medicine, National Institutes of Health, GenBank Locus HS313D11, Accession No. Z92544, "Human DNa sequence from cosmid 313D11 from a contig on the short arm of chromosome 16," [online]. Bethesda, MD [retrieved on Oct. 24, 2000]. Retrieved from the Internet.

National Center for Biotechnology Information, National Library of Medicine, National Institutes of Health, GenBank Locus NM_004323, Accession No. NM_004323, "*Homo sapiens*BCL2-associated athanogene (BAG1), mRNA," [online]. Bethesda, MD [retrieved on Nov. 15, 2000]. Retrieved from the Internet.

Naylor et al., "Evidence for the Existence of Distinct Mammalian Cytosolic, Microsomal, and Two Mitochondrial GrpE-like Proteins, the Co-chaperones of Specific Hsp70 Members," *The Journal of Biological Chemistry, 273*(33):21169-21177 (1998).

Netzer et al., "Protein folding in the cytosol: chaperonin-dependent and -independent mechanisms," *Trends in Biochemical Sciences, 23*:68-73 (1998).

Owens-Grillo et al., "The Cyclosporin A-binding Immunophilin CyP-40 and the FK506-binding Immunophilin hsp56 Bind to a Common Site on hsp90 and Exist in Independent Cytosolic Heterocomplexes with the Untransformed Glucocorticoid Receptor," *The Journal of Biological Chemistry, 270*(35):20479-20484 (1995).

Owens-Grillo et al., "A Model of Protein Targeting Mediated by Immunophilins and Other Proteins That Bind to hsp90 via Tetratricopeptide Repeat Domains," *The Journal of Biological Chemistry, 271*(23):13468-13475 (1996).

Patterson et al., "Cloning and Functional Analysis of the Promoter for KDR/flk-1, a Receptor for Vascular Endothelial Growth Factor," *The Journal of Biological Chemistry, 270*(39):23111-23118 (1995).

Patterson, Winston C., "Mechanisms of KDR-FLK-1 Gene Regulation," Grant Abstract, Grant No. 1K08HL03658-01 [online]. National Heart, Lung, and Blood Institute, National Institutes of Health, project dates Jul. 1, 1997-Jun. 30, 2002 [retrieved on Jan. 24, 2001]. Retrieved from the Internet.

Patterson, Winston C., "Mechanisms of KDR-FLK-1 Gene Regulation," Grant Abstract, Grant No. 5K08HL03658-02 [online]. National Heart, Lung, and Blood Institute, National Institutes of Health, project dates Jul. 1, 1997-Jun. 30, 2002 [retrieved on Jan. 24, 2001]. Retrieved from the Internet.

Patterson, Winston C., "Mechanisms of Neovascularization in Ahtersclerosis," Grant Abstract, Grant No. 1R03AG15234-01 [online]. National Institute on Aging, National Institutes of Health, project dates Sep. 30, 1997-Sep. 29, 1998 [retrieved on Jan. 24, 2001]. Retrieved from the Internet.

Patterson et al., Poster and abstract, "Flavopiridol Inhibits Vascular Smooth Muscle Cell Proliferation in Vitro and Neointimal Formation in Vivo After Carotid Injury in the Rat," Conifer, Excerpta Medica Medical Communications B.V. [online]. Abstract 407-4, American College of Cardiology meeting, New Orleans, LA, Mar.

7-10, 1999, available on-line Jan. 31, 1999[abstract retrieved on Feb. 16, 2001]. Retrieved from the Internet.

Patterson et al., Poster, Keystone Conference: Protein Folding, Degradation, and Molecular Chaperones, Apr. 10-16, Copper Mountain Resort, Copper Mountain, CO, 22 pages (1999).

Pratt et al., "Steroid Receptor Interactions with Heat Shock Protein and Immunophilin Chaperones," *Endocrine Reviews*, 18(3):306-360 1997).

Prodromou et al., "Regulation of Hsp90 ATPase activity by tetratricopeptide repeat (TPR)-domain co-chaperones," *The EMBO Journal*, 18(3):754-762 (Feb. 1, 1999).

Pukatzki et al., "A Novel Component Involved in Ubiquitination Is Required for Development of *Dictyostelium discoideum*," *The Journal of Biological Chemistry*, 273(37):24131-24138 (1998).

Sambrook et al., *Molecular Cloning, A Laboratory Manual*, Cold Spring Harbor Laboratory Press, Cold Spring Harbor, NY, Title page, publication page, and table of contents only, 30 pages (1989).

Sanger et al., "DNA sequencing with chain-terminating inhibitors," *Proceedings of the National Academy of Sciences US*, 74(12):5463-5467 (1977).

Scanlan et al., "Characterization of Human Colon Cancer Antigens Recognized by Autologous Antibodies," *International Journal of Cancer*, 765):652-658 (1998).

Scherrer et al., "Structural and Functional Reconstitution of the Glucocorticoid Receptor-Hsp90 Complex," *The Journal of Biological Chemistry*, 265(3):21397-21400 1990).

Schneider et al., "Pharmacologic shifting of a balance between protein refolding and degradation mediated by Hsp90," *Proceedings of the National Academy of Sciences USA*, 93(25):14536-14541 (1996).

Schumacher et al., "ATP-dependent Chaperoning Activity of Reticulocyte Lysate," *The Journal of Biological Chemistry*, 269(13):9493-9499 (1994).

Segnitz et al., "The Function of Steroid Hormone Receptors Is Inhibited by the hsp90-specific Compound Geldanamycin," *The Journal of. Biological Chemistry*, 272(30):18694-18701 (1997).

Shields et al., "Two Potent Nuclear Localization Signals in the Gut-enriched Krüppel-like Factor Define a Subfamily of Closely Related Krüppel Proteins," *The Journal of Biological Chemistry*, 272(29):18504-18507 (1997).

Shimatake et al., "Purified λ regulatory protein cII positively activates promoters for lysogenic development," *Nature*, 292(5819):128-132 (1981).

Sikorski et al., "A Repeating Amino Acid Motif in *CDC23* Defines a Family of Proteins and a New Relationship among Genes Required for Mitosis and RNA Synthesis," *Cell*, 60:307-317 1990).

Smith et al., "Production of Human Beta Interferon in Insect Cells Infected with a Baculovirus Expression Vector," *Molecular and Cellular Biology*, 3(12):2156-2165 (1983).

Smith et al., "Identification of a 60-Kilodalton Stress-Related Protein, p60, Which Interacts with hsp90 and hsp70," *Molecular and Cellular Biology*, 13:869-876 (1993).

Smith et al., "Molecular Chaperones: Biology and Prospects for Pharmacological Intervention," *Pharmacological Reviews*, 50(4):493-513 (1998).

Summers et al., "A Manual of Methods for Baculovirus Vectors and Insect Cell Culture Procedures," *Texas Agricultural Experiment Station Bulletin No. 1555*, Department of Entomology, Texas Agricultural Experiment Station and Texas A&M University, Title page and pp. 1-56 (1987).

Takayama et al., "BAG-1 modulates the chaperone activity of Hsp70/Hsc70," *The EMBO Journal*, 16(16):4887-4896 (1997).

Teter et al., "Polypetide Flux through Bacterial Hsp70: DnaK Cooperates with Trigger Factor in Chaperoning Nascent Chains," *Cell*, 97:755-765 (Jun. 11, 1999).

Ungewickell et al., "Functional Interaction of the Auxilin J Domain with the Nucleotide- and Substrate-binding Modules of Hsc70," *The Journal of Biological Chemistry*, 272(31):19594-19600 (1997).

Urlaub et al., "Isolation of Chinese hamster cell mutants deficient in dihydrofolate reductase activity," *Proceedings of the National Academy of Sciences USA*, 77(7):4216-4220 (1980).

Whitesell et al., "Stable and Specific Binding of Heat Shock Protein 90 by Geldanamycin Disrupts Glucocorticoid Receptor Function in Intact Cells," *Molecular Endocrinology*, 10(6):705-712 (1996).

Wickner et al., "Posttranslational Quality Control: Folding, Refolding, and Degrading Proteins," *Science*, 286:1888-1893 (Dec. 3, 1999).

Wu et al., "Differential transcriptional regulation of the *human thrombin receptor* gene by the Sp family of transcription factors in human endothelial cells," *Biochemical Journal*, 330:1469-1474 (1998).

Wu et al., "The Human *KDR/flk-1* Gene Contains a Functional Initiator Element That Is Bound and Transactivated by TFII-I,"0 *The Journal of Biological Chemistry*, 274(5):3207-3214 (Jan. 29, 1999).

Wu et al., "The human KDR/flk-1 gene contains a functional initiator element that is bound and trasnsactivated by TFII-I," Abstract 425.1, Annual Meeting of Professional Research Scientists and American Association of Anatomists, Experimental Biology '99, Apr. 17-21, Washington, D.C., *The FASEB Journal*, 13(4):A531 (Mar. 12, 1999).

Young et al., "Specific Binding of Tetratricopeptide Repeat Proteins to the C-terminal 12-kDa Domain of hsp90," *The Journal of Biological Chemistry*, 273(29):18007-18010 (1998).

Zeiner et al., "Mammalian protein RAP46: an interaction partner and modulator of 70 kDa heat shock proteins," *The EMBO Journal*, 16(18):5483-5490 (1997).

Ballinger et al., "CHIP's Interaction with HSP90 Regulates Glucocorticoid Receptor Function and Degradation," Abstract and oral presentation, Cold Spring Harbor Meeting on Molecular Chaperones & Heat Shock Response, May 3-7, Cold Spring Harbor, N.Y. (May 4, 2000).

Benjamin et al., "Stress (Heat Shock) Proteins Milecular Chaperones in Cardiovascular Biology and Disease," *Circulation Research Journal of the American Heart Association*, Jul. 27, 1998; 83(2):117-132.

Chang et al., "Phenotypic expression in *E. coli* of a DNA sequence coding for mouse dihydrofolate reductase," *Nature*, 275(19):617-624 (1978).

Hu et al., "Hsp90 is required for the activity of a hepatitis B virus reverse transcriptase," *Proc. Natl. Acad. Sci. USA*. 1996; 93:1060-1064.

Itakura et al., "Expression in *Escherichia coli* of a Chemically Synthesized Gene for the Hormone Somatostatin," *Science*, 198:1056-1063 (1977).

Netting, "Cells have molecule for protein triage," *Science News Online*, Jan. 27, 2001; 159(4).

Schute et al., "Disruption of the Raf-1-Hsp90 Molecular Complex Results in Destabilization of Raf-1 and Loss of Raf-1-Ras Association," *The Journal of Biological Chemistry*, 1995; 270(41):24585-24588.

Sharp et al., "Heat-Shock Protein Protection," *Research News*, 1999;22(3):97-99.

Slavotinek et al., "Unfolding the Role of Chaperones and Chaperonins in Human Disease," *TRENDS in Genetics*, Sep. 2001;17(19):528-535.

Smith et al., "Molecular chaperones: Biology and Prospects for Pharmacological Intervention," *Pharmacological Reviews*, 1998;50(4):493-513.

Xu et al., "Heat-shock protein hsp90 governs the activity of pp60$^{v-src}$ kinase," *Proc. Natl. Acad. Sci. USA*, Aug. 1993; 90:7074-7078.

Yenari et al., "The Neuroprotective Potential of Heat Shock Protein 70 (HSP70)," *Molecular Medicine Today*, Dec. 1999; 5:525-531.

Imai et al., "CHIP Is Associated with Parkin, a Gene Responsible for Familial Parkinson's Disease, and Enhances its Ubiquitin Ligase Activity," *Molecular Cell*, Jul. 2002;10: 55-67.

Taverna and Goldstein, "Why are Proteins So Robust To Site Mutations?" *Journal of Mol. Biology*, 2002;315:479-484.

Yan et al., "AtCHIP, a U-Box-Containing E3 Ubigquitin Ligase, Plays a Critical Role in Temperature Stress Tolerance in Arabidopsis," *Plant Physiology*, Jun. 2003;132:861-869.

Amalfitano and Parks, "Separating Fact from Ficton: Assessing he Potential of Modified Adenovirus Vectors for Use in Human Gene Therapy," *Current Gene Therapy*, 2002;2:111-133.

Houdebine, "Production of pharmaceutical proteins from transgenic animals," *Journal of Biotechnology*, 1994:34:269-287.

Pandha et al., "Oncological applications of gene therapy," *Curr Opin Invest Drugs*, 2000;1(1):122-34.

Patterson A.P., "Notification of a Serious Adverse Event," Memorandum Department of Health and Human Services, Jan. 14, 2003: 3 pgs.

Verma and Somia, "Gene therapy-promises, problems and prospects," *Nature*, Sep. 18, 1997;389:239-42.

"CHIP (C-terminus of Hsc70-Interacting Protein) A U-box-dependent E3 ubiquitin ligase," [online].*Phoenix Pharmaceuticals, Inc.* [retrieved on Jul. 19, 2005].

"In Vitro Protein Expression Guide," *Promega*, 50 pgs, Apr. 2005.

* cited by examiner

```
   1                          CGGATCGCGGGCTCGGGCTGCGGGGCTCCGGCTGCG
  37 GGCGCTGGCCGCGAGGCGCGGAGCTTGGGAGCGGAGCCCAGGCCGTGCCGCGCGGCGCC
  97 ATGAAGGGCAAGGAGGAGAAGGAGGGCGGCGCACGGCTGGGCGCTGGCGGCGGAAGCCCC
      M  K  G  K  E  E  K  E  G  G  A  R  L  G  A  G  G  G  S  P    20
 157 GAGAAGAGCCCGAGCGCGCAGGAGCTCAAGGAGCAGGGCAATCGTCTGTTCGTGGGCCGA
      E  K  S  P  S  A  Q  E  L  K  E  Q  G  N  R  L  F  V  G  R    40
 217 AAGTACCCGGAGGCGGCGGCCTGCTACGGCCGCGTGATCACCCGGAACCCGCTGGTGGCC
      K  Y  P  E  A  A  A  C  Y  G  R  V  I  T  R  N  P  L  V  A    60
 277 GTGTATTACACCAACCGGGCCTTGTGCTACCTGAAGATGCAGCAGCACGAGCAGGCCCTG
      V  Y  Y  T  N  R  A  L  C  Y  L  K  M  Q  Q  H  E  Q  A  L    80
 337 GCCGACTGCCGGCGCGCCCTGGAGCTGGACGGGCAGTCTGTGAAGGCGCACTTCTTCCTG
      A  D  C  R  R  A  L  E  L  D  G  Q  S  V  K  A  H  F  F  L   100
 397 GGGCAGTGCCAGCTGGAGATGGAGAGCTATGATGAGGCCATCGCCAATCTGCAGCGAGCT
      G  Q  C  Q  L  E  M  E  S  Y  D  E  A  I  A  N  L  Q  R  A   120
 457 TACAGCCTGGCCAAGGAGCAGCGGCTGAACTTCGGGGACGACATCCCCAGCGCTCTTCGA
      Y  S  L  A  K  E  Q  R  L  N  F  G  D  D  I  P  S  A  L  R   140
 517 ATCGCGAAGAAGAAGCGCTGGAACAGCATTGAGGAGCGGCGCATCCACCAGGAGAGCGAG
      I  A  K  K  K  R  W  N  S  I  E  E  R  R  I  H  Q  E  S  E   160
 577 CTGCACTCCTACCTCTCCAGGCTCATTGCCGCGGAGCGTGAGAGGGAGCTGGAAGAGTGC
      L  H  S  Y  L  S  R  L  I  A  A  E  R  E  R  E  L  E  E  C   180
 637 CAGCGAAACCACGAGGGTGATGAGGACGACAGCCACGTCCGGGCCCAGCAGGCCTGCATT
      Q  R  N  H  E  G  D  E  D  D  S  H  V  R  A  Q  Q  A  C  I   200
 697 GAGGCCAAGCACGACAAGTACATGGCGGACATGGACGAGCTTTTTTCTCAGGTGGATGAG
      E  A  K  H  D  K  Y  M  A  D  M  D  E  L  F  S  Q  V  D  E   220
 757 AAGAGGAAGAAGCGAGACATCCCCGACTACCTGTGTGGCAAGATCAGCTTTGAGCTGATG
      K  R  K  K  R  D  I  P  D  Y  L  C  G  K  I  S  F  E  L  M   240
 817 CGGGAGCCGTGCATCACGCCCAGTGGCATCACCTACGACCGCAAGGACATCGAGGAGCAC
      R  E  P  C  I  T  P  S  G  I  T  Y  D  R  K  D  I  E  E  H   260
 877 CTGCAGCGTGTGGGTCATTTTGACCCCGTGACCCGGAGCCCCCTGACCCAGGAACAGCTC
      L  Q  R  V  G  H  F  D  P  V  T  R  S  P  L  T  Q  E  Q  L   280
 937 ATCCCCAACTTGGCTATGAAGGAGGTTATTGACGCATTCATCTCTGAGAATGGCTGGGTG
      I  P  N  L  A  M  K  E  V  I  D  A  F  I  S  E  N  G  W  V   300
 997 GAGGACTACTGAGGTTCCCTGCCCTACCTGGCGTCCTGGTCCAGGGGAGCCCTGGGCAGA
      E  D  Y  *                                                   303
1057 AGCCCCCGGCCCCTATACATAGTTTATGTTCCTGGCCACCCCGACCGCTTCCCCCAAGTT
1117 CTGCTGTTGGACTCTGGACTGTTTCCCCTCTCAGCATCGCTTTTGCTGGGCCGTGATCGT
1177 CCCCCTTTGTGGGCTGGAAAAGCAGGTGAGGGTGGGCTGGGCTGAGGCCATTGCCGCCAC
1237 TATCTGTGTAATAAAATCCGTGAGCACGAGGTGGGACGTGCTGGTGTGTG
```

FIG. 1

| Consensus | AXXYKNRAXXXLKLXXYEXAIADYXRAIELDPXX |
|---|---|
| hCHIP-TPR1 | AQELKEQGNRLFVGRKYPEAAACYGRVITRNPLV |
| hCHIP-TPR2 | AVYYTNRALCYLKMQQHEQALADCRRALELDGQS |
| hCHIP-TPR3 | VKAHFFLGQCQLEMESYDEAIANLQRAYSLAKEQ |
| hHIP-TPR1 | ANDKKVAAIEALNDGELQKAIDLFTDAIKLNPRL |
| hHIP-TPR2 | AILYAKRASVFVKLQKPNAAIRDCDRAIEINPDS |
| hHIP-TPR3 | AQPYKWRGKAHRLLGHWEEAAHDLALACKLDYDE |
| hPP5-TPR1 | AEELKTQANDYFKAKDYENAIKFYSQAIELNPSN |
| hPP5-TPR2 | AIYYGNRSLAYLRTECYGYALGDATRAIELDKKY |
| hPP5-TPR3 | IKGYYRRAASNMALGKFRAALRDYETVVKVKPHD |
| hCYP-TPR1 | TEDLKNIGNTFFKSQNWEMAIKKYAEVLRYVDSS |
| hCYP-TPR2 | LSCVLNIGACKLEMSNWQGAIDSCLEALELDPSN |
| hCYP-TPR3 | TKALYRRAQGWQGLKEYDQALADLKKAQGIAPED |

FIG. 2

| | | | | | | |
|---|---|---|---|---|---|---|
| Human ORF | MKCKEEKEGG | ARIGAGGG-S | PEKSPSAQFL | KEQGNRLEVG | RKYPHAALGY | 4 |
| Mouse ORF | MKCKEEKEGG | ARGTGGGGS | PDKSPSAQFL | KEQGNRLEVG | RKYPHAALGY | 5 |
| Drosophila ORF | MTKHIY-ST | UN-------- | ----SDLGIL | KEQGNGLAA | RKDDAINGY | 3 |
| Consensus | MKCKEEKEGG | ARIG.GGG-S | P.KSPSAQFL | KEQGNRLEVG | RKYPHAALGY | 5 |
| | | | | | | |
| Human ORF | GRVITRNPLV | AVMYTNRALG | MLKVQQHPDA | LADRRATEL | EGDSVKPHEE | 9 |
| Mouse ORF | GRAITRNPLV | AVMYTNRALG | MLKVQQHPDA | LADRRATEL | EGDSVKPHEE | 10 |
| Drosophila ORF | SKATIKNPIN | AIYFDNRALG | NLKLKRWELC | CQDSRKAEI | PGNLLKGPEE | 8 |
| Consensus | GRAITRNPLV | AVMYTNRALG | MLKVQQ.PDA | LADRRATEL | EGDSVKPHEE | 10 |
| | | | | | | |
| Human ORF | EGGCQLEMES | YDEATANQR | AYSPAKEQRL | NEGDDIPSAL | RIAKKKRWNS | 14 |
| Mouse ORF | EGGCQLEMES | YDEATANQR | AYSPAKEQRL | NEGDDIPSAL | RIAKKKRWNS | 15 |
| Drosophila ORF | EGGLMEIDN | RDEATKEQR | AYDLEKEQKQ | NEGDDITLQL | SRIARKKRWAV | 13 |
| Consensus | EGGCQLEMES | YDEATANQR | AYSPAKEQRL | NEGDDIPSAL | RIAKKKRWNS | 15 |
| | | | | | | |
| Human ORF | IEDRRIHOES | EHSYLSRLTI | AAERERELEE | CQRNHIGDED | DSHVRAQQAC | 19 |
| Mouse ORF | IEDRRIHOES | EHSYLTRLTI | AAERERELEE | CQRNHIGDED | DGHIRAQQAC | 20 |
| Drosophila ORF | MEHKRIQQEI | EQSVINGLT | KGSMESRIAN | --LKLANQVH | DEQLKDKQQE | 18 |
| Consensus | IEDRRIHOES | EHSYL.RLTI | AAERERELEE | CQRNHIGDED | D.H.RAQQAC | 20 |
| | | | | | | |
| Human ORF | IPAKHDKYMA | DMDELESQVD | EKKKRDIPD | MLGGKISKEL | MREDITISC | 24 |
| Mouse ORF | IPAKHDKYMA | DMDELESQVD | EKKKRDIPD | MLGGKISKEL | MREDITISC | 25 |
| Drosophila ORF | IRQECEDHIK | ENNIESVID | ERKKRDIPD | HLGGKISPEI | TPMIDSC | 23 |
| Consensus | IPAKHDKYMA | DMDELESQVD | EKKKRDIPD | MLGGKISKEL | MREDITISC | 25 |
| | | | | | | |
| Human ORF | LTYPRQDEEH | HIQRVGHPDP | VTSHLIQEQV | LPNLAMKEVI | IDAETISENW | 29 |
| Mouse ORF | LTYPRQDEEH | HIQRVGHPDP | VTSHLIQEQV | LPNLAMKEVI | IDAETISENW | 30 |
| Drosophila ORF | LTYRQDIEEH | HIQRVGHPDP | VTRVKLIQEQ | TPNFSMKEVM | DEETAENW | 28 |
| Consensus | LTYPRQDEEH | HIQRVGHPDP | VTSHLIQEQV | LPNLAMKEVI | IDAETISENW | 30 |
| | | | | | | |
| Human ORF | VEDY | | | | | 30 |
| Mouse ORF | VEDY | | | | | 30 |
| Drosophila ORF | SIDY | | | | | 28 |
| Consensus | VEDY | | | | | 30 |

FIG. 3 mouse cDNA II Sequence

```
GGGCTGCGAG ATCTAGGTGG CCGGGCGCGG AGCCCAAGCC GTGCCGCGCG      50
GCGCCATGAA GGGCAAGGAG GAAAAGGAGG GCGGCGCGCG GCTGGGCACT     100
GGTGGCGGCG GCAGCCCTGA TAAGAGCCCG AGTGCGCAAG AGCTCAAGGA     150
GCAGGGAAAC CGGCTCTTCG TGGGCCGCAA GTACCCGGAG GCGGCGGCCT     200
GCTACGCCG CGCCATCACT CGGAACCCAC TTGTGGCAGT GTACTACACC      250
AACCGGGCCC TGTGCTATCT GAAGATGCAG CAGCCTGAAC AGGCACTTGC     300
TGACTGCCGG CGAGCCCTGG AGCTGGACGG GCAGTCTGTG AAGGCGCACT     350
TCTTCCTGGG GCAGTGCCAG CTGGAGATGG AGAGTTATGA TGAGGCCATT     400
GCCAATCTGC AGCGAGCCTA TAGTTTGGCC AAGGAGCAGC GACTCAACTT     450
TGGGGATGAT ATTCCTAGTG CCCTTCGCAT TGCTAAGAAG AAGCGCTGGA     500
ACAGTATCGA GGAACGGCGC ATCCACCAGG AGAGTGAGCT GCATTCATAT     550
CTCACCAGGC TCATTGCTGC TGAGCGAGAG AGGGAACTGG AGGAGTGTCA     600
GCGGAACCAC GAGGGTCATG AAGATGATGG CCACATCCGG GCCCAGCAGG     650
CCTGCATTGA GGCCAAGCAC GATAAATACA TGGCAGATAT GGATGAGCTC     700
TTCTCTCAGG TGGACGAGAA AAGAAAGAAG CGAGATATCC CTGACTACTT     750
GTGTGGCAAG ATTAGCTTTG AGCTGATGCG GGAACCCTGC ATTACACCA      800
GTGGTATCAC CTATGACCGC AAGGACATTG AGGAGCACCT GCAGCGTGTG     850
GGCCACTTTG ACCCTGTCAC CCGGAGCCCT CTGACCCAGG AACAGCTCAT     900
CCCCAACTTG GCCATGAAGG AAGTCATTGA CGCTTTCATC TCTGAGAACG     950
GCTGGGTAGA GGACTATTGA GGCCCCATGT CCTGCCTGGC ACCCTGGCCC    1000
AGGAGGATCT GGAGACGGAA GCTCCAGTCC CTGTATAGTT TGTGTCCCTG    1050
GGCCTGCCCC CATCGGCCCT GCTGATGGGT TCTGAACTGC TCCCTTCTC     1100
AGCATACCCC TTGCTGGACC ATGAGCCTCC CTTGTCCCCC TTCTGGGCTG    1150
GAGAGTGGGT GAGGGTGGGC TGAGGTTGCT GCTGCTGCCA CTGTCCTGTA    1200
ATAAAGTCTG TGAGCACT                                       1218
```

FIG. 9A mouse ORF II Sequence

```
MKGKEEKEGG ARLGTGGGGS PDKSPSAQEL KEQGNRLFVG RKYPEAAACY     50
GRAITRNPLV AVYYTNRALC YLKMQQPEQA LADCRRALEL DGQSVKAHFF    100
LGQCQLEMES YDEAIANLQR AYSLAKEQRL NFGDDIPSAL RIAKKKRWNS    150
IEERRIHQES ELHSYLTRLI AAERERELEE CQRNHEGHED DGHIRAQQAC    200
IEAKHDKYMA DMDELFSQVD EKRKKRDIPD YLCGKISFEL MREPCITPSG    250
ITYDRKDIEE HLQRVGHFDP VIRSPLTQEQ LIPNLAMKEV IDAFISENGW    300
VEDY                                                       304
```

FIG. 9B

Drosophila cDNA Sequence

```
AAAATTGTTT TATGTTAAT TAAATACAGG CGAATAGCTC AAGATCTTTT      50
TGGTGTTATG AGCGTTCAAA AGTCACTACC GTTTCCCACT TAATACTTTG    100
TTAACTGTTA AGTTCGTGCA GCAGTTCCCC AATTCTTGCA GAGGAAACAA    150
ATTTACGAGT GCTTCGGTGT TGTTGGACAC ACACTCACTT TTCATCGGTG    200
GAAAATCAAA TTTGGGACCA GGCGCAGAAG ATTCGTCAGG ATGACGACCA    250
AGCACATCTA TTCCACGACC AATTTATCAG ATCTGCAATT AAAGGAGCAG    300
GGAAACTGCT TGTTTGCAGC CCGAAAATAT GACGACGCAA TAAATTGCTA    350
CTCAAAGGCC ATCATAAAGA ACCCCACAAA CGCCACATAC TTCACAAACC    400
GAGCCCTCTG CAACCTGAAA CTGAAGAGAT GGGAACTGTG CTGCCAGGAT    450
AGTCGGCGCG CCCTCGACAT CGATGGGAAT CTGTTGAAGG GTCACTTCTT    500
CCTGGGCCAA GGACTCATGG AAATCGACAA CTTTGACGAG GCTATAAAGC    550
ACCTTCAACG GGCATACGAT CTGTCCAAGG AGCAGAAGCA AAACTTTGGG    600
GATGATATTA CACTACAGTT GCGACTAGCT CGCAAAAAGC GCTGGAATGT    650
TATGGAGGAG AAGCGAATAC AGCAGGAAAT CGAGCTGCAA AGCTATTTAA    700
ATGGTCTAAT AAAAGGGGAC ATGGAAAGCC GTTTGGCCAA TTTAAAGCTG    750
AATGGAAATG TACACGATGA GCAGCTGAAA GACAAGCAAC AGGAAATTGA    800
GCAAGAATGC GATGACCATA TTAAGGAACT TAACAATATA TTTTCTAAGG    850
TTGACGAACG TCGAAAGAAA CGTGAAGTTC CCGATTTTCT ATGTGGCAAA    900
ATAAGTTTTG AAATATTAAC AGACCCTGTG ATAACTCCAT CTGGAATTAC    950
GTATGAACCA AAAGATATAG AAGAACACTT GCAGCGGGTT GGACATTTCG   1000
ATCCTGTGAC ACGCGTTAAG CTCACTCAGG ATCAACTAAT ACCAAATTTT   1050
TCAATGAAGG AAGTGGTTGA CTCTTTTATT GCCGAGAATG AATGGTCTTT   1100
AGATTATTAA GTTACTTATT AGTTGGCATT GTCATTGTAA TTGATTAGAT   1150
GTTAGAACCC AGTTCCCATT GTCTAAAAAC CAGATAAGTG ATAATAAATG   1200
TGGATCTGCA ATTGAGATTT ATATG                              1225
```

FIG. 10A

Drosophila ORF Sequence

```
MTKHIYSIT NLSDLQLKEQ GNCLFAARKY DDAINCYSKA IIKNPINATY      50
FTNRALCNLK LKRWELCCQD SRRALDIDGN LLKGHFFLGQ GLMEIDNFDE    100
AIKHLQRAYD LSKEQKQNFG DDITLQLRLA RKKRWNVMEE KRIQQEIELQ    150
SYLNGLIKGD MESRLANLKL NGNVHDEQLK DKQQEIEQEC DHIKELNNI     200
FSKVDERRKK REVPDFLCGK ISFEILIDPV ITPSGITYER KDIEEHLQRV    250
GHFDPVIRVK LTQDQLIPNF SMKEVVDSFI AENEWSLDY               289
```

FIG. 10B

```
                             ARNT            ARNT             MyoD
-2000    ctgtgggagctgggggcacgcgggatggctgggggccgggcgtgtggtcaggccaggtgtgtggtcaggccgggt
         GR             ets/Nkx-2.5
-1925    gtgtgatcaggcgtgagtttgggaagtgtttattgagctcccgtagtggccagcctcctcttcagcctccctgcc
                                        MyoD
-1850    gtccagtgagacccggaggcctgaggttctgtggcaggtgagcaggcctgggccatggccaagtttactcggcct
                 NF-1                                             NF-1
-1775    gggttccatgcttcttggctggcctagcatcctcgtgggtggccaggctggggccaaggttgggcagcaggtctg
              GR  NF-E2                                                    GR
-1700    ggcacagcctctgccccacagcccaggtccacagtgctgtctccactaggtagggagtccactgtcctgaggcac
         GR                                                              GR
-1625    tggctagggagggcacacggactcaggcccaggggcacgggccaccccaacctgcccacacacagttcattccc
-1550    cttggctcagagctgtggcccgctcttgaacctggcccaggtacagcaggtagtacctgagggtgtactgtgggg
                                      MyoD                                MyoD
-1475    ccggccagccgggcactgtggccaccgcctcatctgacatgaaggcctccatctctggagctccagctgccagga
                                      GR                 GR
-1400    ctgctgtgaacagcgaggagaagcagccagacacaccccatcaggacaagtctgggagacctgctcccagcag
                                           ARNT
 1325    cccagggccctatggttcctgctcctagcgacacgcaagggcccagactgccgcttcacagacaagaacgccta
                                                                      GR
 1250    tgtacccaagtcgtgcccacccaactcacccgaggctgtggtgggcccacaccgcagagggcacacagctcggtg
                                  MyoD                                       CCAAT
 1175    actgcagccccacatctggcaggaggcagaaggtggcggtcgaacagtgcacaaccagctcaggggattggtg
                 MyoD            NFκB              PPAR   Myogenin
 1100    gccaccagctgctgcagacgtggccggaaagcgccctctgtgggaggccaggtcagggtgcctggggtgctggac
                       NFκB/Sp1
 1025    ccaccagggagggccccgccccactggagacacccgccccgccgatgccacgccccaatgaagacccgcgctacg
               Sp1
  950    gaggccctgccctcggggcgggccgcccttcacagtcaagctgccaggccagcagccgctccagctccctgtcac
           USF   NF-E2                      ets/GATA        ets/Sp1
  875    atgcttctctgctctgcccctgatggccgctggcaactcttcccgatacctgaggaagggcggtgaggggaggac
                                          GATA
         Sp1
  800    tggccacggaggacgctcgccccaccgatctctatccccttccactctaccaacagtccggggcttccagccgcc
  725    ctcggggctcgcgctcgcccgtagcacctctcgtggcgctccagaatggcagcccagcgactgggggtcctcaca
             Ets                         Sp1                    Sp1
  650    ccccacagcgcgtgggaaagccgctacgttcacgcgcaggggcggggaggcggcggctggggcggggcctctgctg
                        Sp1       CCAAT              Sp1
 -575    atgggccgggtgctggggcggggcctctggattgggcggttgctggggcggggcctctgcggatggggctgg
             Sp1                        Sp1           CCAAT/Sp1              Sp1
 -500    gggcggggcctctgctgatggggccggcggctggggcggggcctctggattgggcggctgctggggcggggcc
                                         Sp1                          Sp1
 -425    tctgcggatggggccggctgctggggcggggcctctggatggggccggctgccggggagggtctctgcgcgt
           GR    Sp1       MyoD      GR                              Nkx-2.5/IRF
 -350    tgggacaggggcgggaaccccaggtggtcgggacaggctgttgcgggagcgcgccctcagcgaaagcaagtgaggca
                                                      C/EBP/NF-1
 -275    tctcactgggaaagtcgaatgtgtgtggcggccgccgccgaggcgggttccgaagagacctcagcagggcaggcc
                                                                   GR              ets
 -200    agggcctacgcgaacgccaccccttaagagcgcgggggacagggaactggagcgttcctcccagccccgacgtcg
```

FIG. 11 (page 1)

```
                    GR
-125       cgggcccagtgtccccgtccaggctggttgggcgcacgcgcggccccactcgcccccacgcgtgcgtcccgctg
           Sp1        NFκB (pal)
 D50       gtcccgccccggccggaagttccggcggcggagctgggccgggcccgagCGGATCGCGGGCTCGGGCTGCGGGG +26       CTCCGGCTGCGGGCGCTGGGCCGCGAGGCGCGGAGCTTGGGAGCGGAGCCCAGGCCGTGCCGCGCGGCGCCATGA
                                   Exon 1A                        Sp1
                          GR
+101       AGGGCAAGGAGGAGAAGGAGGGCGGCGCACGGCTGGGCGCTGGCGGCGGAAGCCCCGAGAAGAGCCCGAGCGCGC +176       AGGAGCTCAAGGAGCAGGGCAATCGTCTGTTCGTGGGCCGAAAGTACCCGGAGGCGGCGGCCTGCTACGGCCGCG
           E2F           EGR      Sp1
+251       CGATCgtgagtgcgcccgcgcggggagggcggcggcggtggcaccggggagggccgggcccgggcccggccggcc
                               GR
+326       ccaccgagggtctggctcctcttcggggcgtgtcctcggctcccaaagcccagccgtggttctcgagCCCAGCGC +401       CGGGTGCCGGAGAACGAGGGTGCGATGCTGGATGGAGGCCGGCCGGGTGGGGGGAGGGCAGGGGCCCTCGACCCT +476       TGAGGACCCCAGGTCCTAAGCCCGGACTCTCCAAAGATTTGGAAAACTTTACAAAACCAAGTGGAATCAAGCGGA
      Exon 1B
+551       TAGGCTCAGCCAGTACTCCACTGTGCACAGATCCTTGGACCCAGGGGCTTTGACAACTGAGAAACCTAGTTTCTT +626       GATTCTAGCCAGAGCGCAGAAGCTGGGACGGGCCGTGGGTCAGAGTGGGCACGCTGAGCCTACGCCCTCATGCGG +701       CTGGCCCGGCCTTGGTCCCTAGACCCGGAACCCGCTGGTGGCCGTGTATTACACCAACCGGGCCTTGTGCTACCT +776       GAAGATGCAGCAGCACGAGCAGGCCCTGGCCGACTGCCGGCGCGCCCTGGAGCTGGACGGGCAGTCTGTGAAGGC
      Exon 2
+851       GCACTTCTTCCTGGGGCAGTGCCAGCTGGAGATGGAGAGCTATGATGAGGCCATCGCCAATCTGCAGCGAGgttg +926       gctgacaagctgcccggttgtggggcctctggggccaggcgggtggactggccagagagtgacgtgaagcccccg +1001      ttccccagCTTACAGCCTGGCCAAGGAGCAGCGGCTGAACTTCGGGGACGACATCCCCAGCGCTCTTCGAATCGC
      Exon 3A
+1076      GAAGAAGAAGCGCTGGAACAGCATTGAGGAGCGGCGCATCCACCAGGAGAGCGAGCTGCACTCCTACCTCTCCAG +1151      GCTCATTGCCGCGGAGCGTGAGAGgtgggaccctcaccccaggccgccctgtcttgggataattctgaatcaccg +1226      actcccgacacaagcgtttatcgaaggctttactggcaagcaggaaatgtggggaagtgtggatgttagctctga
      Exon 3B
+1301      gattgggtgtggtcagacatctggccaggtccatctctgaccggctcctggtcaaccccagGGAGCTGGAAGA
      Exon 3C
+1376      GTGCCAGCGAAACCACGAGGGTGATGAGGACGACAGCCACGTCCGGGCCCAGCAGGCCTGCATTGAGGCCAAGCA +1451      Cgtgaagggtgcccccacccacatgtgggtctgtgtgtgtgcacgtggcgtgggagcatcccgccttgtgttgg
      Exon 3D
+1526      gtctgtgcccatggaggagggaggtggggtgtctcccccaagcacagcactcaactcttcacagGACAAGTACA
      Exon 3E
+1601      TGGCGGACATGGACGAGCTTTTTTCTCAGGTGGATGAGAAGAGGAAGgtgagtgtgtgtcgcttgctgccgatgg +1676      ctggcaggtgctcgtgcagtgccccttttcagcctctgaccgtgtgcccctgtgccacagAAGCGAGACATCCCC +1751      GACTACCTGTGTGGCAAGATCAGCTTTGAGCTGATGCGGGAGCCGTGCATCACGCCCAGTGGCATCACCTACGAC
      Exon 4
+1826      CGCAAGGACATCGAGGAGCACCTGCAGgtgaggcctgcggctgggggagcagggccagtggcatggtcctgggcc +1901      ccatgactgccctctgcccttcttgtcactgcagCGTGTGGGTCATTTTGACCCCGTGACCCGGAGCCCCCTGAC +1976      CCAGGAACAGCTCATCCCCAACTTGGCTATGAAGGAGGTTATTGACGCATTCATCTCTGAGAATGGCTGGGTGGA
```

```
+2051          GGACTACTGAGGTTCCCTGCCCTACCTGGCGTCCTGGTCCAGGGGAGCCCTGGGCAGAAGCCCCCGGCCCCTATA
      Exon 5
+2126          CATAGTTTATGTTCCTGGCCACCCCGACCGCTTCCCCCAAGTTCTGCTGTTGGACTCTGGACTGTTTCCCCTCTC +2201          AGCATCGCTTTTGCTGGGCCGTGATCGTCCCCCTTTGTGGGCTGGAAAAGCAGGTGAGGGTGGGCTGGGCTGAGG +2276          CCATTGCCGCCACTATCTGTGTAATAAAATCCGTGAGCACGAGGTGGGACGTGCTGGTGTGTGaccggcagtcct
               gccagctgttttggctagccgaggaaggtggagatgaagacgctggtgtcaaggttgagcgtagcatgccaccag
+2426          cggtcggggaagtacagcacctggtggaggaaggggtgcagcagagattagctgcgggcctctagcctggcctg
               gccctctcctgccagccactgacctcaccagcccggatggtacactccaggggccgtgcagacggtggcagggct
+2576          tgagcagcagtgtcacccttgcccgttttggtcagcgagtcccaagcctcaacccccaccccgtgctgaccttac
               gaccgtagatcacttctgagtacccgggtccatgccagtggaagggcaccccgagccagctcctgtggggttat
+2726          gagcacctggtgaccaacccatttgtactcaccgacagaagcctcagtccttcccagtcccaagaagcacccac
               ctgcgattccaaagctgtaagctggagcggttcccagcaggccaaatgggggtggggagtagtgccgaaagagag
+2876          aggcccactcggtgaagttgttgtccccgaagaagtacagggtgtctgccaacagagacggcggggacagggatc
               ctggcacctggagactccaagcgtccccaccccctaccgccgcctagggctgcctcaccattgcccagggaggtg
+3026          gggtcctgggggtgcagcagctgctccacatactcctggaagggcaagtccactgcaggaaagagacgggtcagg
               accgtctggtccagccgccccggtgttggcaaatgggcgggcccaggggtgaggccgcgtaccttttgtggtagg
+3176          agtaggtgttggcggtgctcagccggaccactctgtccccaaacgaagccagcaacctgtcgcgggagcac
```

FIG. 11 (page 3)

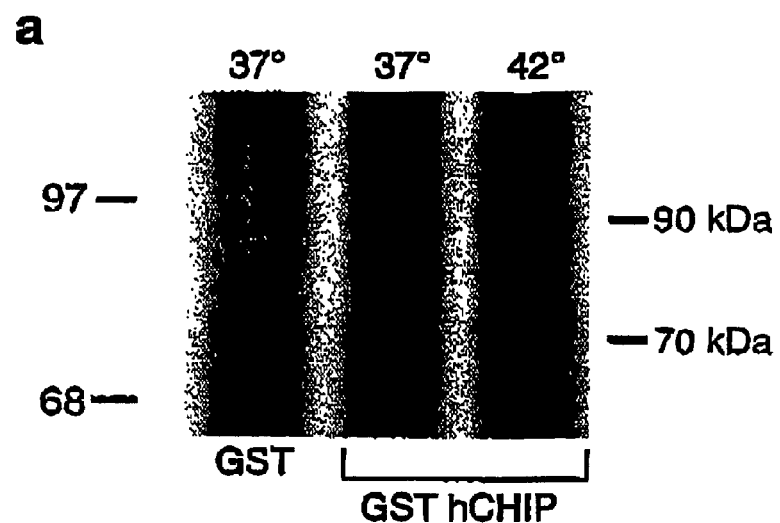
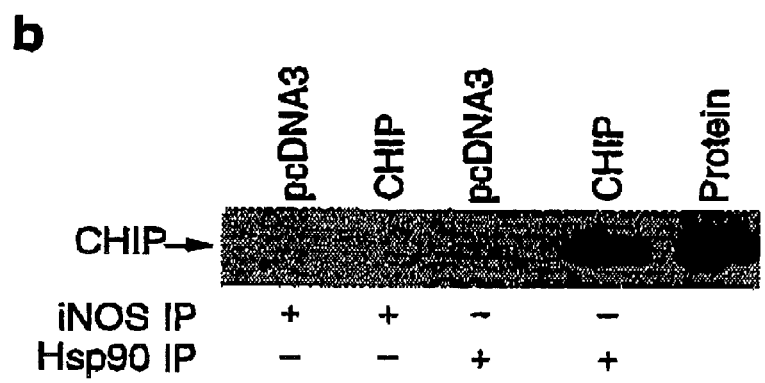
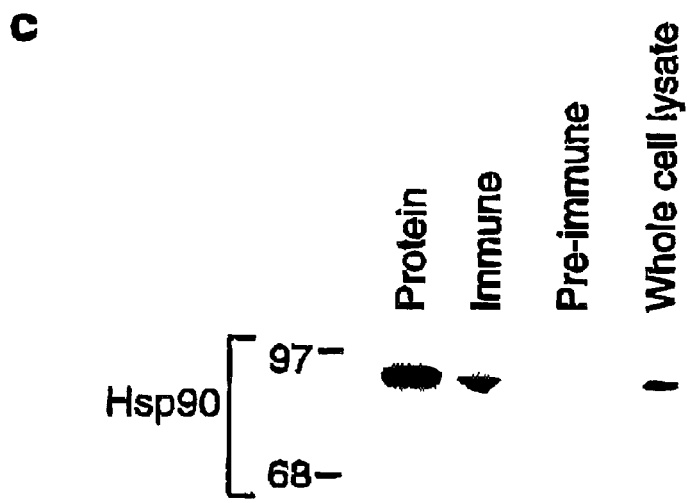
Figure 12

POLYPEPTIDE THAT INTERACTS WITH HEAT SHOCK PROTEINS

PRIORITY APPLICATION

This application claims benefit of U.S. Provisional Patent Application Ser. No. 60/134,433, filed May 17, 1999, which is incorporated herein by reference.

STATEMENT OF GOVERNMENT RIGHTS

The present invention was made with support from the National Institutes of Health under Grant Nos. HL03658 and AG15234. The government may have certain rights in this invention.

BACKGROUND

Multi-protein complexes, which are the product of protein—protein interactions, participate in a variety of cellular processes. Such exemplary cellular processes include, for example, cell signaling, gene regulation, protein assembly and degradation, and mechanical events such as sarcomere shortening. Conserved structural motifs in many proteins have evolved to facilitate the interaction of specific proteins in the assembly of multi-protein complexes. The tetratricopeptide repeat (TPR) domain is one such structural motif that was originally identified by sequence comparisons among yeast proteins (Hirano et al., *Cell,* 60:319–328 (1990), Sikorski et al., *Cell,* 60:307–317 (1990)). The TPR domain contains a 34-amino acid structural motif with a loose consensus that is present, usually as multiple tandem repeats, in proteins with many cellular functions, including mitosis, transcription, protein transport, and development (Lamb et al., *Trends in Biochemical Sciences,* 20:257–259 (1995)). Structural analysis of the TPR domain demonstrates that it forms two α-helical regions separated by a turn, such that opposed bulky and small side chains form a "knob and hole" structure (Hirano et al., *Cell,* 60:319–328 (1990)). It is thought that a hydrophobic surface of this particular TPR domain mediates protein—protein interactions between TPR- and non-TPR-containing proteins.

TPR-containing proteins are typically known to play a diverse and important role in cellular function. Several TPR-containing proteins are known to participate in interactions with the major members of the heat shock protein family, Hsp70, Hsc70, and Hsp90. It is believed that these TPR-containing proteins are necessary for appropriate regulation of protein folding and transport. The TPR domains of protein phosphatase 5, cyclophilin 40 (CyP-40), and FKBP52 are known to mediate binding of these proteins to Hsp90 and assist in trafficking of nuclear hormone receptors (J. E. Kay, *Biochem. J.,* 314:361–385 (1996)). A different group of TPR-containing proteins are known to interact with Hsc70 and Hsp70. Hsc70-Interacting Protein (HIP), also known as p48, binds to the ATPase domain of Hsc70, stabilizes the ADP-bound conformation, and increases the affinity for substrate proteins (Höhfeld et al., *Cell* 83:589–598 (1995)). Hsc70–Hsp90-Organizing Protein (HOP), also known as p60 or Sti1, serves as a coupling factor that facilitates the cooperation between Hsc70 and Hsp90, although it does not directly assist in chaperoning functions (Schumacher et al., *J. Biol. Chem.,* 269:9493–9499 (1994)). In contrast to HIP, HOP interacts with the carboxy-terminal domain of Hsc70 (Demand et al., *Mol. Cell. Biol.,* 18:2023–2028 (1998)).

In addition to fHP, at least two other proteins are known to regulate the reaction cycle of mammalian Hsc70 and Hsp70. Hsp40 stimulates the ATPase activity of Hsc70 and thus promotes the conversion of ATP-bound, low substrate-affinity Hsc70 to ADP-bound, high substrate-affinity Hsc70 (J. Höhfeld, *Biol. Chem.,* 379:269–274 (1998)). The reverse reaction cycle, which involves exchange of ATP for ADP and loss of substrate affinity, was recently shown to be facilitated by the anti-apoptotic protein BAG-1 (Zeiner et al., *EMBO J.,* 16:5483–5490 (1997)). Whereas HIP inhibits this reverse reaction cycle and stabilizes the ADP-bound conformation, no cellular inhibitors of the forward reaction cycle of the binding of a heat shock protein to a substrate to form a protein—protein complex have yet been identified.

Thus, there is a need for further understanding cellular components that regulate and interact with heat shock proteins, and identifying such cellular components.

SUMMARY OF THE INVENTION

Described herein are the isolation and characterization of a polypeptide, particularly a tetratricopeptide repeat (TPR)-containing polypeptide that is an interactive partner with heat shock proteins. A preferred polypeptide is referred to herein as Carboxyl terminus of Hsc70-Interacting Protein or "CHIP," not only because of its ability to negatively regulate formation of heat shock protein-substrate complexes by interacting with the forward reaction cycle of heat shock proteins and other accessory chaperone cofactors, but also because the polypeptide interacts in an ATP-independent fashion with these heat shock proteins. The nucleic acid and deduced amino acid sequences of this polypeptide in humans, mice, and *Drosophila* are provided.

Accordingly, the present invention provides an isolated polypeptide that negatively regulates binding of a heat shock protein to a substrate. Preferably, the polypeptide negatively regulates the heat shock proteins Hsc70, Hsp70, and Hsp90. The polypeptide can be a recombinant polypeptide. The polypeptide preferably has a molecular weight of about 30 kD to about 40 kD as determined by SDS polyacrylamide gel electrophoresis.

The present invention also provides a preferred isolated polypeptide having an amino acid sequence having greater than about 40% sequence identity to that of at least one of SEQ ID NOs. 2, 7, and 8. A particularly preferred polypeptide contains at least amino acids 1–197 from any of the polypeptides of SEQ ID NOs. 2, 7, and 8 is capable of negatively regulating the binding of a heat shock protein to a substrate. The polypeptide can be recombinant.

In another preferred embodiment, the present invention further provides an isolated polypeptide having an amino acid sequence represented by at least one of SEQ ID NOs. 2, 7, and 8. Preferably, the polypeptide is capable of negatively regulating the binding of a heat shock protein to a substrate. The polypeptide can be recombinant.

In another preferred embodiment, the present invention also provides a polypeptide containing an amino acid sequence represented by at least one of SEQ ID NOs. 2, 7, and 8, wherein the polypeptide has a molecular weight as determined by SDS polyacrylamide gel electrophoresis of about 30 kD to about 40 kD.

Also provided is a preferred polypeptide that negatively regulates binding of a heat shock protein to a substrate wherein nucleic acid encoding the polypeptide hybridizes to the nucleic acid or the nucleic acid complement of at least one of SEQ ID NOs. 1, 9, 10, and 11 under hybridization conditions of 0.015 M NaCl/0.0015 M sodium citrate (SSC) and about 0.1% sodium dodecyl sulfate (SDS) at about 50° C. to about 65° C.

The present invention further provides a nucleic acid fragment capable of hybridizing to at least one of SEQ ID NOs. 1, 9, 10, and 11, or a complement of at least one of SEQ ID NOs. 1, 9, 10, and 11, under hybridization conditions of 0.015 M NaCl/0.0015 M sodium citrate (SSC) and about 0.1% sodium dodecyl sulfate (SDS) at about 50° C. to about 65C. Preferably, the nucleic acid fragment encodes at least a portion of a polypeptide, which is preferably capable of negatively regulating binding of a heat shock protein to a substrate. The nucleic acid fragment may further be provided in a nucleic acid vector, such as an expression vector that is capable of producing at least a portion of a polypeptide.

In another embodiment, the present invention provides a host cell that includes the nucleic acid fragment described herein. The host cell can be prokaryotic or eukaryotic.

A particularly preferred embodiment of the present invention is an isolated nucleic acid fragment having the nucleic acid sequence represented by at least one of SEQ ID NOs. 1, 9, 10, and 11, or a complement thereof.

The present invention also provides a nucleic acid fragment having a nucleic acid sequence with at least about 60% nucleic acid identity to that of at least one of SEQ ID NOs. 1, 9, 10, and 11, and a complement of the nucleic acid fragment.

The present invention further provides a method for identifying an inhibitor of a polypeptide that has negative regulating activity for a heat shock protein, the method includes incubating the polypeptide with a compound under conditions that promote the negative regulating activity of the polypeptide when the compound is not present, and determining if the negative regulating activity of the polypeptide is reduced relative to the negative regulating activity of the polypeptide in the absence of the compound.

Also provided is a method of expressing a nucleic acid fragment that encodes a polypeptide, the presence of which is associated with negative regulation of a heat shock protein, the method includes expressing the nucleic acid fragment in a cultured host cell transformed with an expression vector containing the nucleic acid fragment operably linked to control sequences recognized by the host cell. A suitable host cell of the invention may be a prokaryotic or eukaryotic cell, preferably a prokaryotic cell, which can form a part of a gram negative or gram positive organism. Preferably, the host cell is an *E. coli* cell. Preferably, the nucleic acid fragment has a nucleic acid sequence represented by at least one of SEQ ID NOs. 1, 9, 10, and 11, or a complement thereof. The expressed polypeptide preferably contains an amino acid sequence having greater than about 40% amino acid sequence identity to that of at least one of SEQ ID NOs. 2, 7, and 8.

The present invention also provides a method for producing a recombinant polypeptide by: a) providing an expression vector that contains a nucleic acid fragment having a nucleic acid sequence with at least about 60% nucleic acid identity to that of at least one of SEQ ID NOs. 1, 9, 10, and 11, or a complement of the nucleic acid fragment, operably linked to control sequences recognized by a host cell; b) transforming the host cell with the expression vector; and c) culturing the transformed cell under conditions that allow expression of the recombinant polypeptide encoded by the nucleic acid fragment. A suitable host cell may be a prokaryotic or eukaryotic cell, preferably a prokaryotic cell, which can form a part of a gram negative or gram positive organism. Preferably, the host cell is an *E. coli* cell.

Further provided is a method for inhibiting a polypeptide that negatively regulates binding of a heat shock protein to a substrate in a mammal by administering to the mammal a composition containing an amount of an inhibitor to an isolated polypeptide having an amino acid sequence identity greater than about 40% to that of at least one of SEQ ID NOs. 2, 7, and 8. Preferably, the composition is therapeutically effective for a neoplastic disease, ischemic disease, or a disease characterized by inflammation.

The present invention also provides a method for inhibiting a nucleic acid that encodes a polypeptide that negatively regulates binding of a heat shock protein to a substrate in a mammal by administering to the mammal a composition containing an amount of an inhibitor to an isolated nucleic acid fragment having a nucleic acid sequence with at least about 60% nucleic acid identity to that of at least one of SEQ ID NOs. 1, 9, 10, and 11, or a complement of the nucleic acid fragment.

The present invention further provides an inhibitory composition having an amount of an inhibitor to an isolated polypeptide, which negatively regulates binding of a heat shock protein to a substrate, that is effective to immunize or treat a mammal for a neoplastic disease, an ischemic disease, or a disease characterized by inflammation. Preferably, the inhibitory composition is provided in an amount effective to provide a therapeutic effect to a mammal diagnosed with a neoplastic disease, an ischemic disease, or a disease characterized by inflammation. The composition may optionally contain a pharmaceutically acceptable carrier.

Definitions

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations, and the like.

As used herein, the term "isolated" means that a polypeptide is either removed from its natural environment or synthetically derived. Preferably, the polypeptide is purified, i.e., essentially free from any other polypeptides and associated cellular products or other impurities.

The term "recombinant nucleic acid," or "recombinant polynucleotide" as used herein, refers to a nucleic acid of genomic, cDNA, semisynthetic, or synthetic origin which by virtue of its origin or manipulation is not associated with all or a portion of a nucleic acid with which it is associated in nature, is linked to a nucleic acid other than that to which it is linked in nature, or does not occur in nature.

The term "recombinant polypeptide" refers to a polypeptide that is not necessarily translated from a designated nucleic acid. The recombinant polypeptide may be generated in any manner, including for example, chemical synthesis, or expression of a recombinant expression system. A recombinant polypeptide may include one or more analogs of amino acid residues or unnatural amino acid residues in its sequence. Methods of inserting analogs of amino acid residues into a sequence are known in the art. The recombinant polypeptide further includes a "fusion polypeptide." As used herein, a "fusion" polypeptide is a product of a first nucleic acid, for example a polypeptide according to the present invention, and a second nucleic acid, for example a glutathione S-transferase sequence (GST), operably linked at either the carboxyl terminus or amino terminus of the first sequence. Expression of this fusion polypeptide results in a single or continuous polypeptide when expressed and isolated from a host cell. The product of this expression can enhance properties relating to, for example, purification, isolation, targeting, and increased immunogenicity.

The term "operably linked" is defined to mean that at least one nucleic acid or nucleic acid fragment is placed in a functional relationship with at least one other nucleic acid or nucleic acid fragment. For example, a nucleic acid fragment for a presequence or secretory leader can be operably linked to nucleic acid fragment that encodes a polypeptide or a fusion polypeptide according to the present invention. A promoter or enhancer is "operably linked" to a nucleic acid fragment, e.g., a coding region, if it affects the transcription of the sequence or if it is positioned so as to facilitate translation. Generally, "operably linked" means that nucleic acids being linked are contiguous and, in the case of a secretory leader, contiguous and in reading frame. Linking is accomplished by ligation at convenient restriction sites. If such sites do not exist, the synthetic oligonucleotide adaptors, linkers, or primers are used in accord with conventional practice.

A "coding region," also referred to as an "open reading frame" (ORF), is a nucleic acid which is transcribed into mRNA and/or translated into a polypeptide when placed under the control of appropriate regulatory sequences. The boundaries of the coding region are determined by a translation start codon at the 5'-terminus and a translation stop codon at the 3'-terminus. A coding region can include, but is not limited to mRNA, cDNA, and recombinant nucleic acid.

"CHIP" refers to a preferred polypeptide according to the present invention that possesses "negative regulating activity" with respect to the binding of a heat shock protein to a substrate to form a heat shock protein-substrate complex, e.g., a protein—protein complex. Although not intending to be limited to a particular mechanism or theory, it is believed this "negative regulating activity" may occur by reducing or inhibiting heat shock protein ATPase activity, inhibiting or reducing binding of one or more accessory chaperone cofactors to a heat shock protein, by the direct binding or complexing of the heat shock protein with a CHIP polypeptide, and/or by the targeting of substrates for degradation. ATPase activity may be reduced or inhibited by the polypeptide's ability to interfere with the forward reaction cycle which includes the hydrolysis of ATP to ADP and inorganic phosphate and the subsequent binding of a heat shock protein to a substrate to form a protein—protein complex.

A "nucleic acid fragment" as used herein refers to a linear polymeric form of nucleotides of any length, either ribonucleotides or deoxynucleotides, and includes both double- and single-stranded DNA and RNA. A nucleic acid fragment may include both coding regions and noncoding regions that can be obtained directly from a natural source (e.g., a microorganism), or can be prepared with the aid of recombinant techniques (including chemical synthetic techniques, as defined herein). A nucleic acid molecule may be equivalent to this nucleic acid fragment or it can include this fragment in addition to one or more other nucleotides. For example, the nucleic acid molecule of the invention can be a vector, such as an expression system or cloning vector.

"Recombinant host cells," "host cells," "cells," "cell lines," "cell cultures," and other such terms denoting microorganisms or higher eukaryotic cell lines cultured as unicellular entities refer to cells that can be, or have been used as recipients for a nucleic acid vector or other transfer nucleic acid, and include the progeny of the original cell which has been transformed. It is understood that the progeny of a single parental cell may not necessarily be completely identical in morphology or in genomic or total nucleic acid complement as the original parent, due to natural, accidental or deliberate mutation.

An "active analog" or "active fragment" of a polypeptide of the invention is one that is characterized by negative regulating activity as described herein. Active analogs and active fragments are described in greater detail herein.

"Amino acid identity" or "percentage amino acid identity," refers to a comparison of the amino acid residues of two polypeptides. The polypeptides to be compared are preferably aligned such that the amino acid residues are aligned to maximize the number of amino acids that the polypeptides have in common along the lengths of their sequences; gaps in either or both sequences are permitted in making the alignment in order to maximize the number of shared amino acids, although the amino acids in each sequence must nonetheless remain in their proper order. The percentage amino acid identity is the number of amino acids that the two sequences have in common within the alignment, divided by the number of amino acids in the amino acid sequence of interest, e.g., at least one of SEQ ID NOs. 2, 7, and 8 multiplied by 100. Preferably, the polypeptide has greater than a 40% amino acid identity, and more preferably at least about 50% amino acid identity to at least one of SEQ ID NOs. 2, 7, and 8. Amino acid identity may be determined, for example, using the sequence alignment program CLUSTAL W available on the World Wide Web at genome.ad.jp/SIT/CLUSTALW.html, and percent amino acid identity can be determined by BLAST 2 SEQUENCE'S at National Center for Biotechnology Information (NCBI) website: on the World Wide Web at .ncbi.nlm.nih.gov.

"Amino acid similarity" or "percentage amino acid similarity," refers to a comparison of the amino acid residues of two polypeptides wherein conservative amino acid residue substitutions are permitted, i.e., amino acid residues that share the same charge and the same polarity are considered "similar." Potential conservative amino acid residue substitutions are described in greater detail below. Preferably, a candidate polypeptide has at least about 60% amino acid similarity, and more preferably at least about 70% amino acid similarity. Amino acid similarity may be determined as described above in reference to determination of amino acid identity.

"Nucleic acid identity" or "percentage nucleic acid identity" refers to a comparison of the nucleic acids of two nucleic acid fragments as described herein. A "high degree" of nucleic acid sequence identity refers to a nucleic acid fragment that typically has at least about 60% nucleic acid sequence identity, and preferably at least about 70% nucleic acid sequence identity. Sequence identity may be determined, for example, using sequence techniques such as GCG FastA (Genetics Computer Group, Madison, Wis.), MacVector™ 4.5 (Kodak/IBI software package) or other suitable sequencing programs or methods known in the art.

BRIEF DESCRIPTION OF THE DRAWINGS

FIG. 1. Human CHIP (hCHIP) cDNA: Nucleic acid (upper line) (SEQ ID NO: 1) and deduced amino acid sequence (lower line) (SEQ ID NO: 2) of hCHIP. Residues containing the three tetratricopeptide repeat (TPR) domains (TPR1, amino acid residues 26–59), (TPR2, amino acid residues 60–93), and (TPR3, amino acid residues 94–127) are singly underlined. A region rich in highly charged residues (amino acid residues 143–190) is doubly underlined. A sequence similar to ubiquitin-proteasome-related proteins (amino acid residues 219–290) is represented by a dashed underline. Potential nuclear localization signals (amino acid residues 143–146 and amino acid residues 221–225) are in boldface.

FIG. 2. Comparison of TPR motifs: hCHIP TPR1 (amino acid residues 26–59 of SEQ ID NO: 2), hCHIP TPR2 (amino acid residues 60–93 of SEQ ID NO: 2), and hCHIP TPR3 (amino acid residues 94–127 of SEQ ID NO: 2) with the three TPR motifs of human HIP (hHIP), hHIP TPR1 (SEQ ID NO: 3), hHIP TPR2 (SEQ ID NO: 16), and hHIP TPR3 (SEQ ID NO: 17), the three TPR motifs of human protein phosphatase 5 (hPP5), hPP5 TPR1 (SEQ ID NO: 4), hPP5 TPR2 (SEQ ID NO: 18), and hPP5 TPR3 (SEQ ID NO: 19), and the three TPR motifs of human cyclophilin-40 (hCYP), hCYP TPR1 (SEQ ID NO: 5), hCYP TPR2 (SEQ ID NO: 20), hCYP TPR3 (SEQ ID NO: 13), illustrates a consensus sequence (SEQ ID NO: 6) for this class of TPR domains.

FIGS. 3A–3B (Hereinafter referred to as FIG. 3). Comparison of the human, mouse, and Drosophila CHIP amino acid sequences: The deduced amino acid sequences derived from human CHIP (SEQ ID NO: 2), mouse CHIP (SEQ ID NO: 7), and Drosophila CHIP (SEQ ID NO: 8), Open Reading Frames (ORFs) were aligned with GENEWORKS 2.5.1. (IntelliGenetics, Campbell, Calif.) using the default parameters. A consensus sequence (SEQ ID NO: 12) is also shown Similar or identical amino acid residues are boxed.

The aggregation of rhodanese was measured at 340 nm over 5 minutes in the absence (♦___) or presence of hCHIP (○___), Hsp70+Hsp40 (□___), or CHIP+Hsp70+Hsp40 (▲___). The measured optical densities were normalized to the zero reading for each individual well of a microtiter plate and the increase in absorbance plotted as a percent of the total increase of rhodanese alone. Each condition was repeated for a total of eight replicates, and points represent the mean±SEM.

Figure 7:
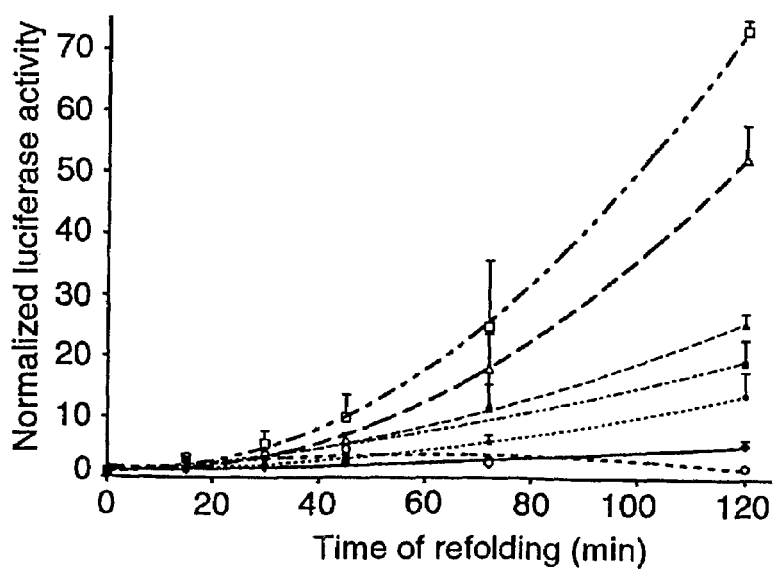

FIG. 7. Luciferase activity was measured as an indication of refolding after thermal denaturation. The refolding reactions were performed with Hsc70 (___□) Hsp40 (___○), or both (___△) in the absence (open symbols) and presence (closed symbols) of CHIP (+CHIP alone). Luciferase activity was measured at various intervals between 0–120 minutes and the activity for each reaction was normalized to luciferase in refolding buffer alone. Each condition was repeated for a total of 12 replicates, and points represent the mean±SEM.

Figure 8:
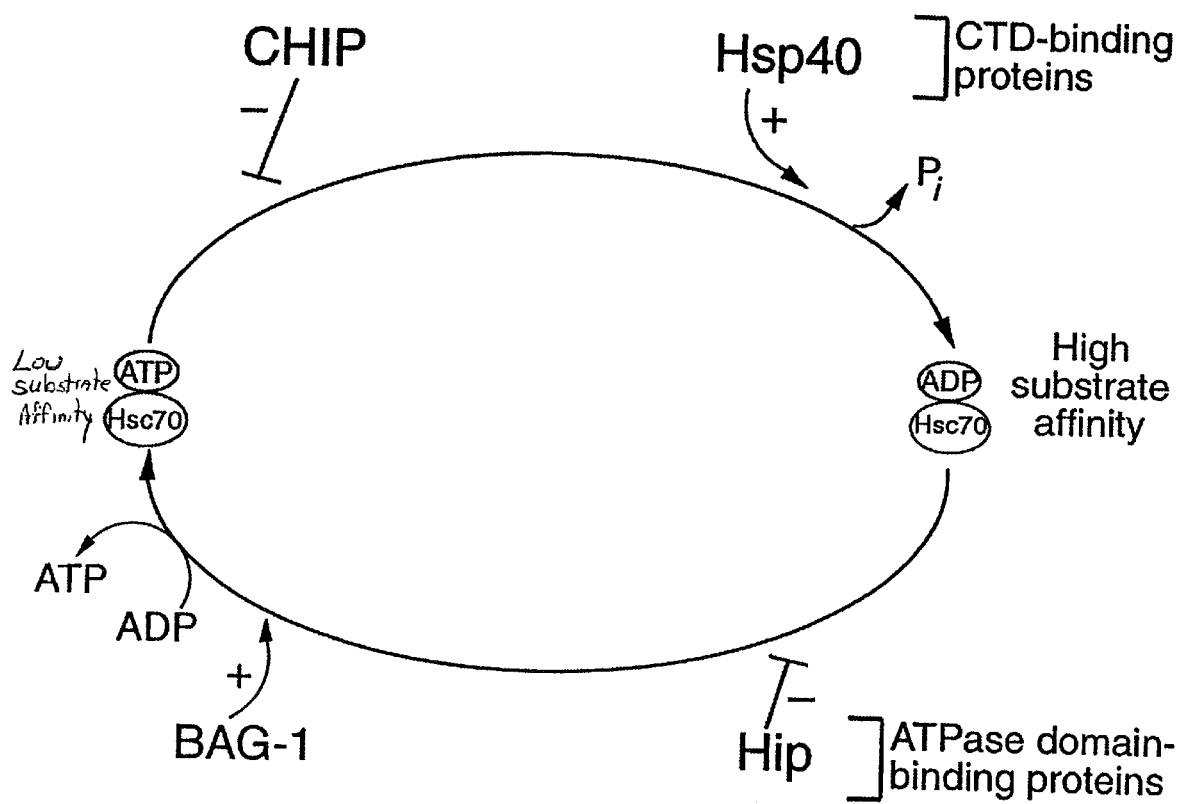

FIG. 8. Model of the eukaryotic reaction cycle in the presence of hCHIP, Hsp40, HIP and BAG-1: The forward reaction cycle, in which ATP is hydrolyzed to ADP and inorganic phosphate (Pi) is released, is enhanced by Hsp40. The biochemical data suggests that hCHIP blocks this forward reaction cycle. HIP stabilizes the ADP-bound, high substrate affinity conformation of Hsc70, and thus enhances chaperone activity. Conversely, BAG-1 accelerates nucleotide exchange, promoting substrate release and the formation of the low substrate affinity, ATP-bound conformation of Hsc70. In this model, both BAG-1 and hCHIP would favor the low affinity Hsc70 conformation, whereas HIP and Hsp40 would favor the high affinity conformation. CTD represents the carboxy-terminal domain of a heat shock protein, such as Hsp70 or Hsp70.

FIG. 9: (A) The cDNA sequence of mouse CHIP (mCHIP) (SEQ ID. NO: 9), and (B) the amino acid sequence of the open reading frame (SEQ ID NO: 7).

FIG. 10: (A) The cDNA sequence of Drosophila CHIP (SEQ ID NO: 10), and (B) the amino acid sequence of the open reading frame (SEQ ID NO: 8).

FIGS. 11A–11E (hereinafter referred to as FIG. 11). The human CHIP (hCHIP) genomic nucleotide sequence (SEQ ID NO: 11).

FIG. 12. CHIP associates with Hsp90 in vivo: (A) Human skeletal muscle cells were incubated at 37° C. or 42° C. $^{35}$S-Methionine-labeled lysates (150 µg) were precipitated with GST or GST-CHIP (15 µg). Sizes of proteins are indicated in kilodaltons. (B) COS-7 cells were immunoprecipitated (IP) with 3G3 or a control antibody (iNOS) and analyzed by Western blotting with anti-CHIP antiserum. (C) Human skeletal muscle cell lysates were immunoprecipitated with anti-CHIP or preimmune serum and analyzed by Western blotting with AC88 to detect Hsp90.

Figure 13:
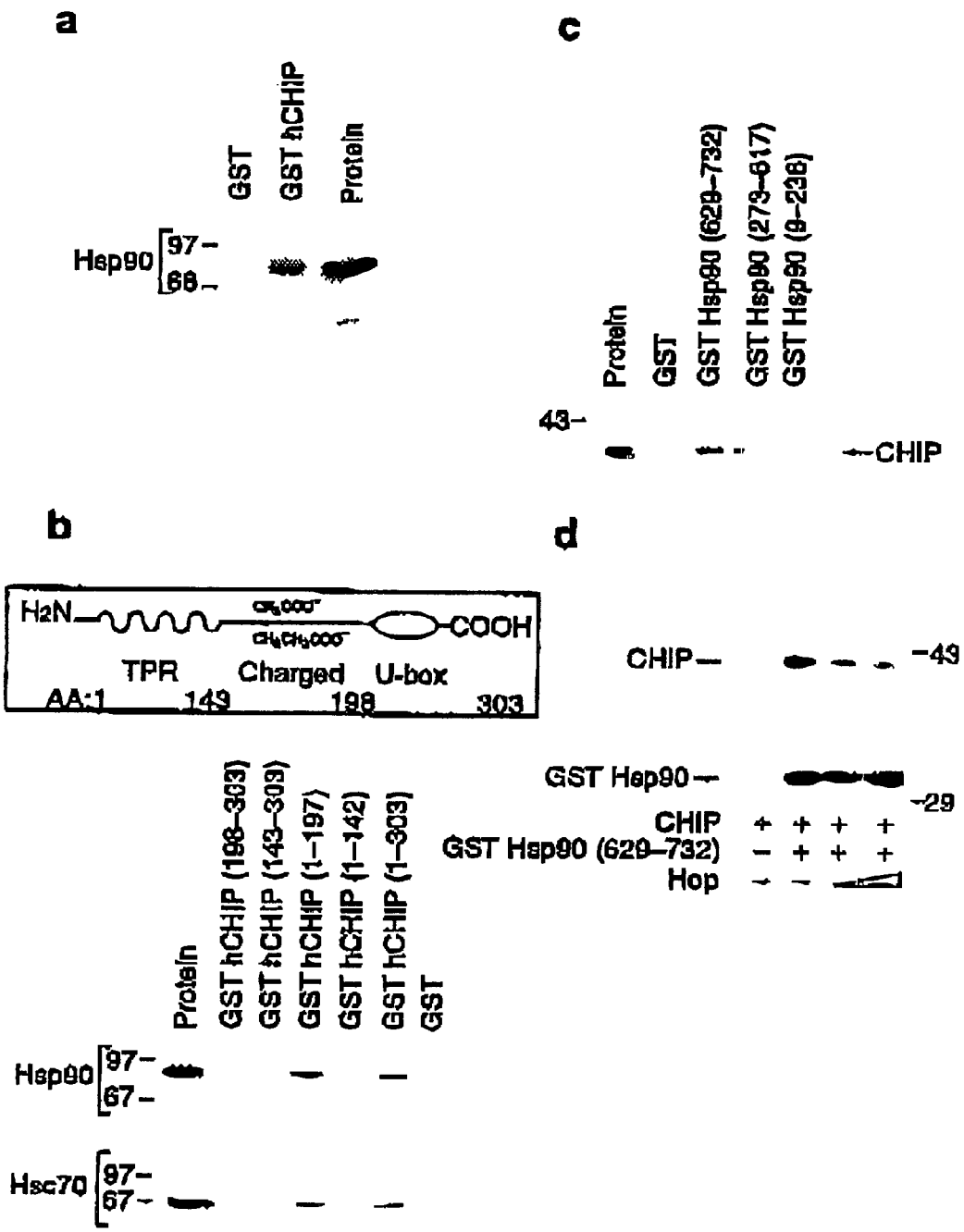

FIG. 13. CHIP interacts with the TPR acceptor site of Hsp90: (A) Binding assays were performed with Hsp90 and GST or GST-CHIP. Blots were probed with AC88 to detect Hsp90. (B) Binding assays were performed with Hsp90 or Hsc70 and GST or GST-CHIP fusion proteins containing the amino acid residues in brackets. Western blots were probed with anti-Hsp90 or anti-Hsc70 antibodies (AA, amino acids). (C) Binding assays were performed with recombinant CHIP and GST or GST fusion proteins containing the indicated amino acid residues of Hsp90. (D) CHIP was incubated with Hsp90 (629–732) fused to GST in the absence or presence of equimolar or 10-fold molar excess of Hop. CHIP bound to Hsp90 was visualized by Western blotting.

Figure 14:
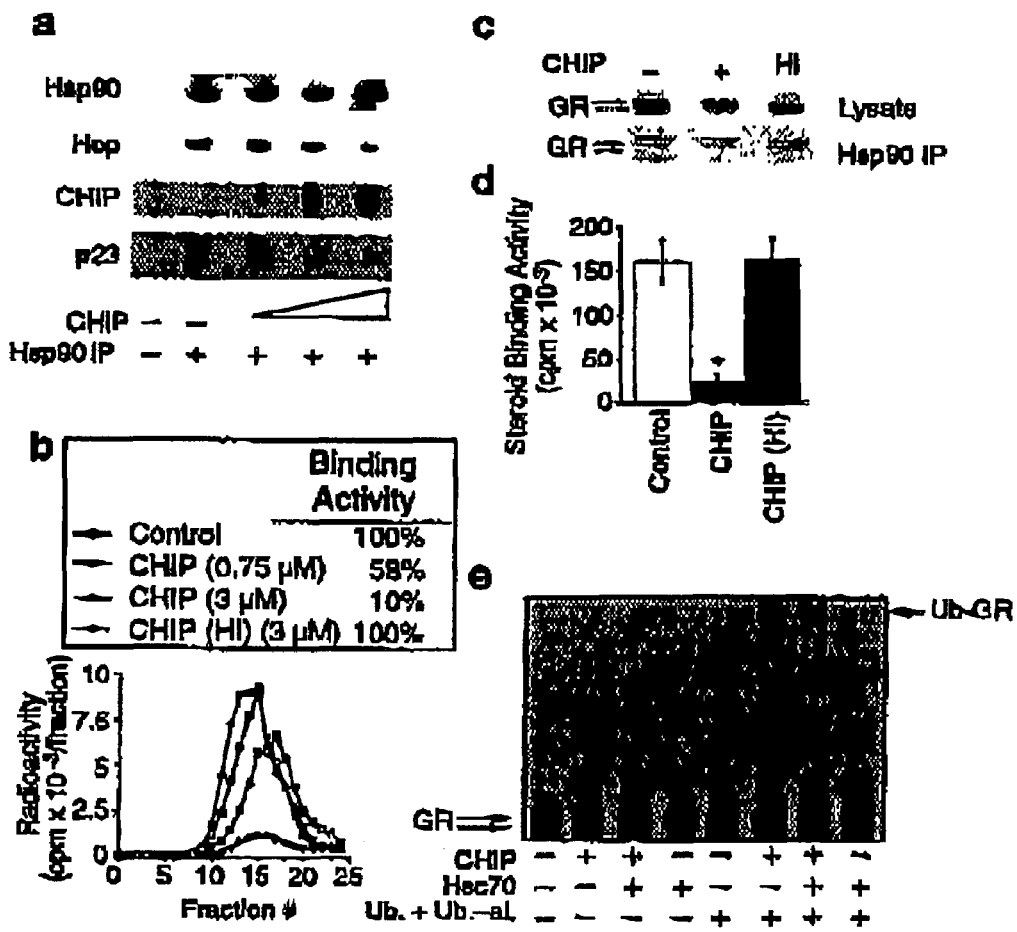

FIG. 14. CHIP blocks Hsp90-mediated chaperoning of GR in reticulocyte lysates. (A) Reticulocyte lysate was incubated with increasing concentrations of CHIP. Hsp90 was immunoprecipitated with 3G3 and Western blots were probed with appropriate antibodies. (B) Hormone binding activity of GR was assessed by incubating samples synthesized in the absence or presence of CHIP (0.75 and 3 µM) or heat-inactivated (HI) CHIP (3 µM) with $^3$H-triamcinolone. The activity is indicated as percent of glucocorticoid binding when CHIP is absent (control). (C) $^{35}$S-Labeled GR was synthesized in the absence or presence of CHIP or heat-inactivated CHIP (upper panel). The effects of CHIP or GR association with Hsp90 were measured by immunoprecipitating $^{35}$S-labeled lysates with 3G3 (lower panel). (D) Hormone binding by the Hsp90-complexed GR was assessed by incubating equivalent amounts of GR from immunoprecipitates with $^3$H-triamcinolone. Shown are the mean values +/–SEM from 4 experiments. *p<0.001. (E) GR was incubated in reticulocyte lysate, with or without CHIP, Hsc70, and/or ubiquitin (Ub) and ubiquitin-aldehyde (Ub-al). The receptor and covalently modified forms of the receptor were detected by autoradiography. Ub-GR indicates the multiubiquitylated forms of GR that accumulate in the presence of CHIP and ubiquitin plus ubiquitin-aldehyde.

Figure 15:
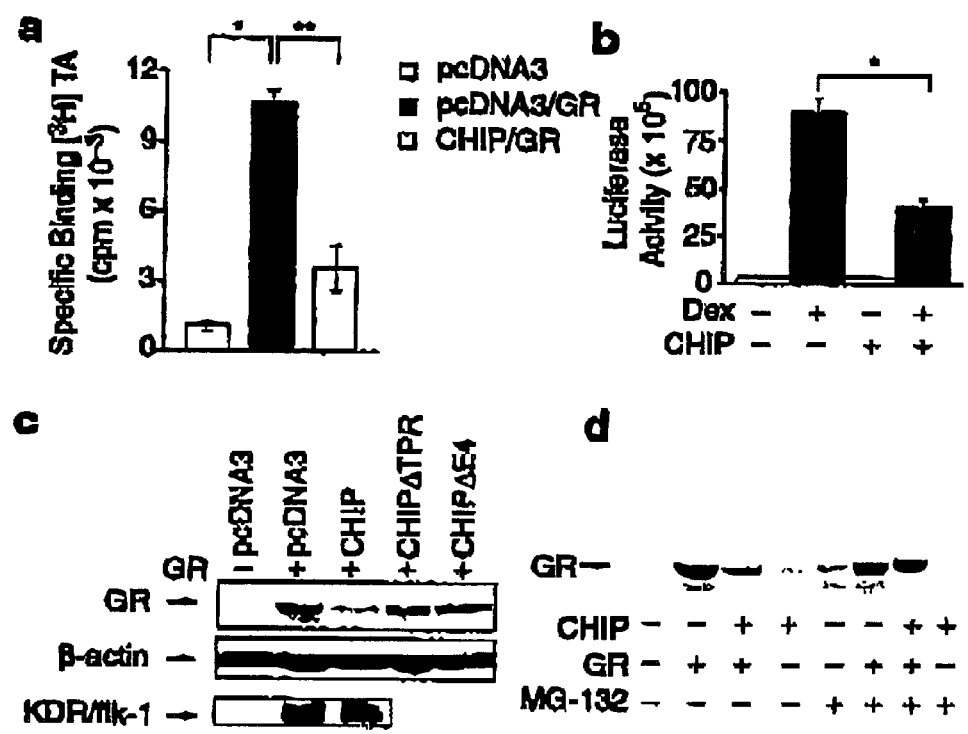
Figure 4:
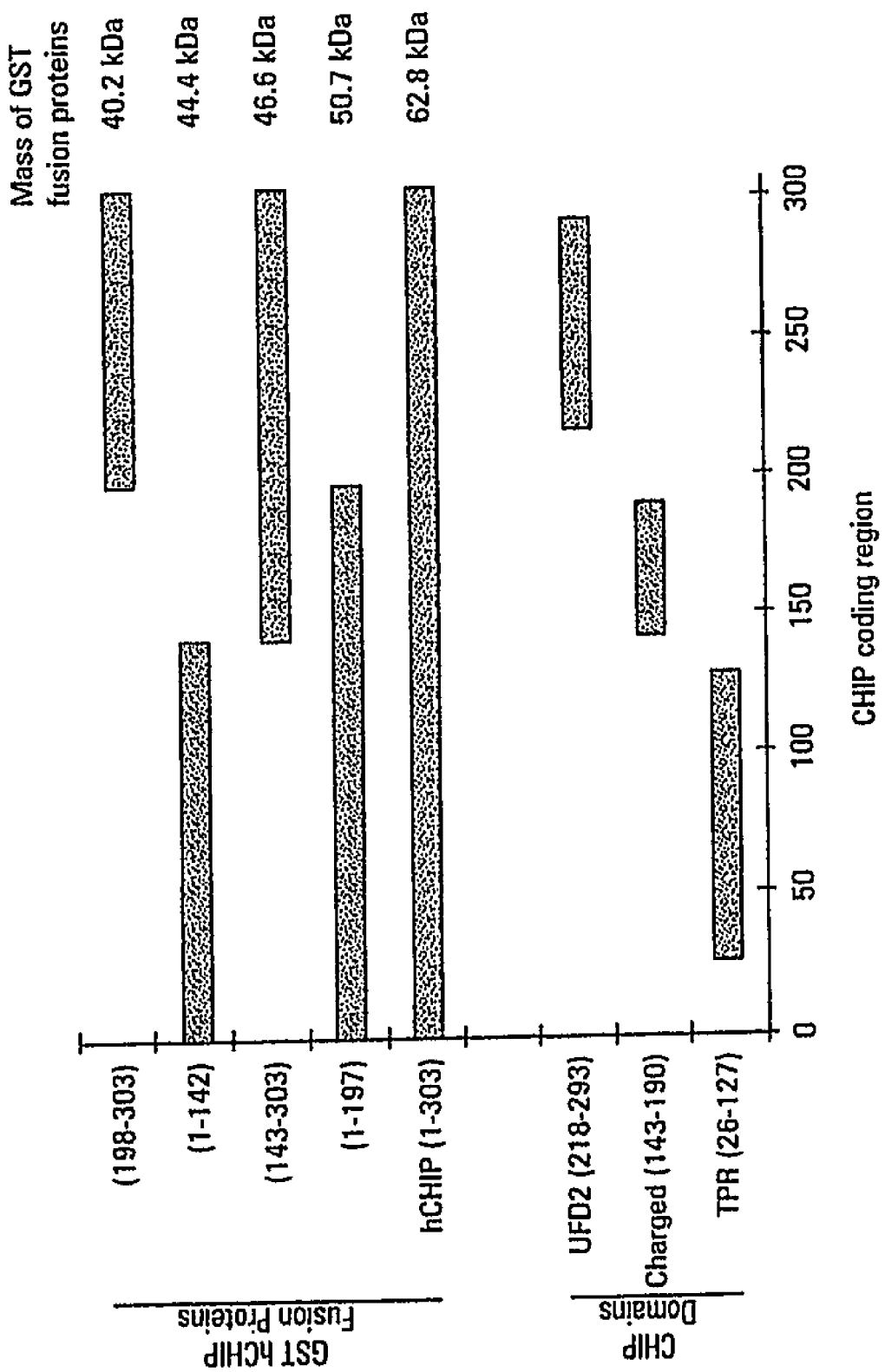
Figure 5:
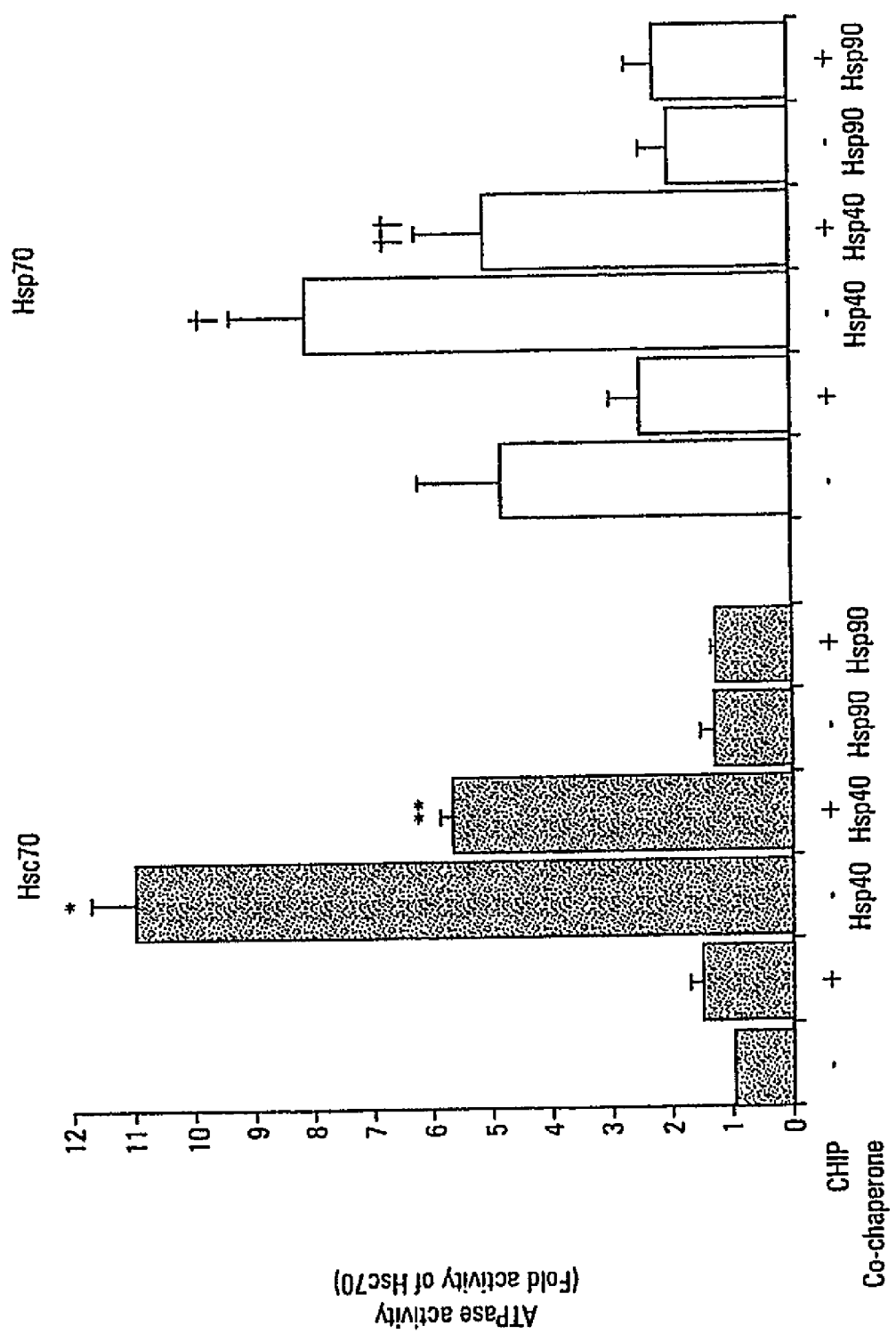
Figure 6:
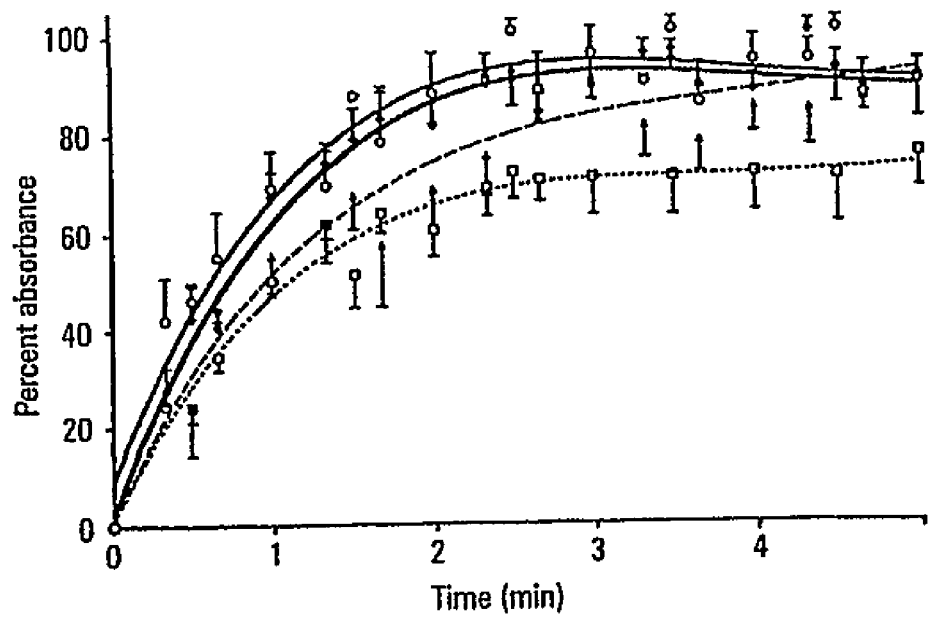
Figure 7:
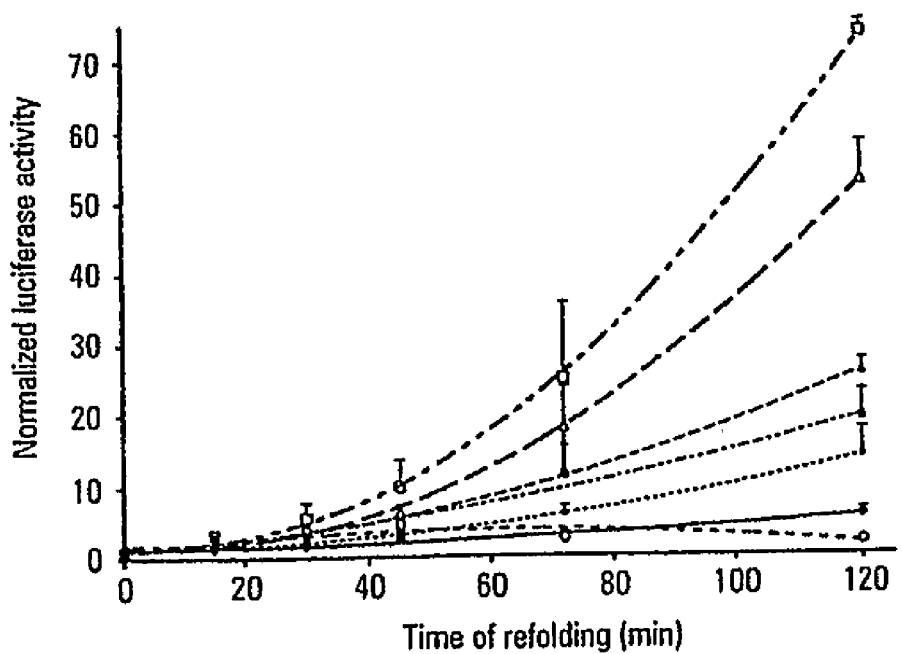
Figure 8:
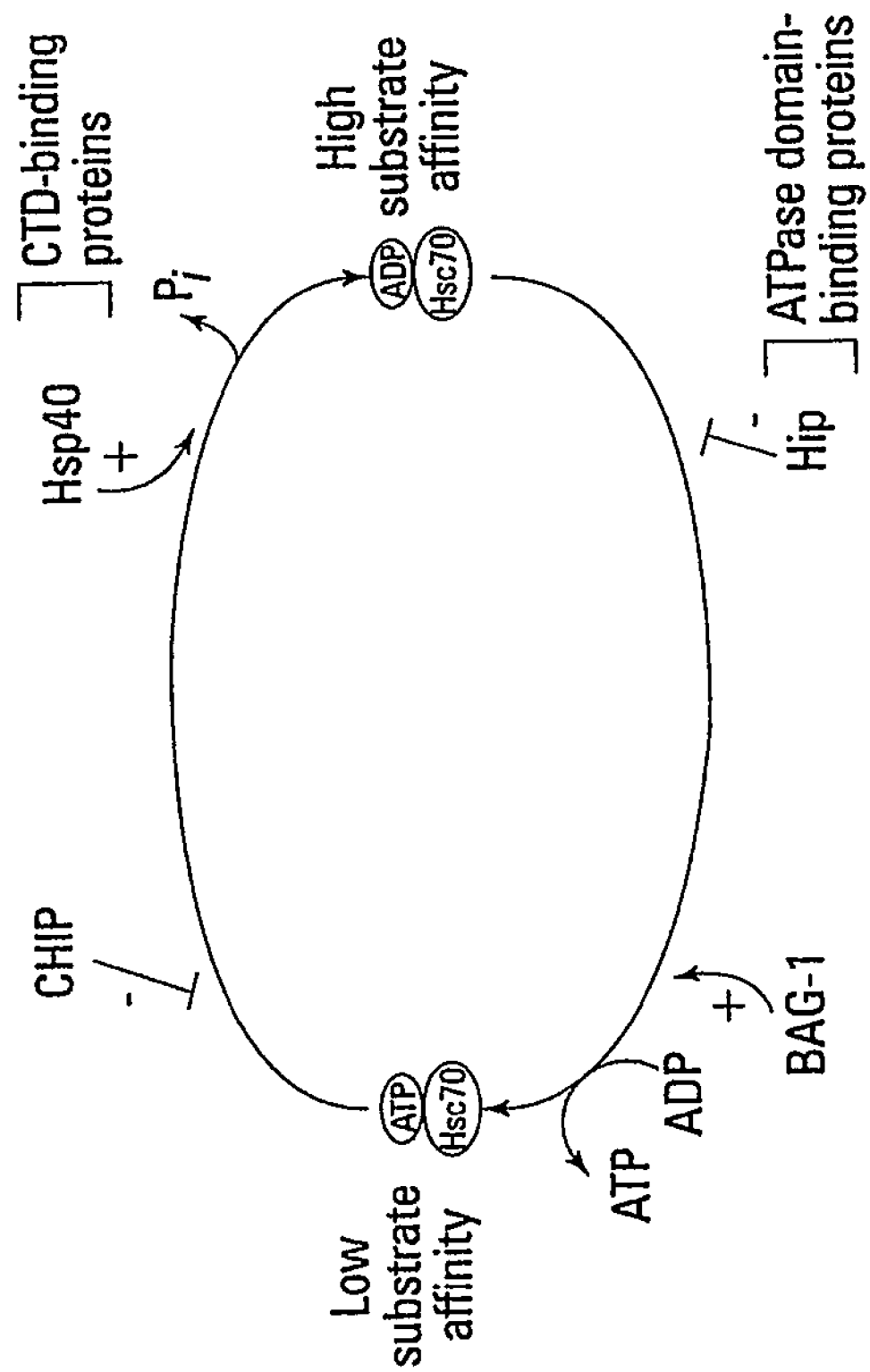

FIG. 15. CHIP inhibits the function and expression of GR in vivo: (A) COS-7 cells were transfected with vectors expressing GR and CHIP or empty vector as a control. Cells were incubated with $^3$H-triamcinolone to measure steroid-binding activity. Shown are the means+/–SEM of 6 experiments. *p<0.0001, **p<0.001. (B) COS-7 cells were transfected with the GR expression plasmid and a dexamethasone-responsive luciferase reporter, with or without the CHIP expression vector. Cells were treated with (black) or without (white) dexamethosone (Dex). Shown are the mean+/–SEM of 12 experiments. *p<0.0001. (C)COS-7 cells were transfected with human GR (upper panel) or KDR/flk-1 (lower panel) with or without CHIP or deletions lacking the TPR (residues 1–145) or U-box (residues 196–303) domains. Western blots were probed with antibodies to the respective proteins or to endogenously expressed β-actin (middle panel). (D) COS-7 cells were transfected with GR with or without CHIP. Cells were incubated with vehicle of MG-132.

DETAILED DESCRIPTION OF PREFERRED EMBODIMENTS

Molecular chaperones, such as the heat shock proteins, work with a set of associated polypeptides and assist, for example, in the folding of other proteins. Molecular chaperones are known to demonstrate an affinity for exposed hydrophobic regions on incompletely folded or denatured proteins, and are also known to hydrolyze ATP, possibly binding and releasing a substrate with each forward reaction cycle of ATP hydrolysis.

Molecular chaperones include a large number of proteins that are involved not only in the acquisition of conformation of individual substrates, but also in the assembly of macromolecular structures. "Chaperoning" is an energy-dependent process that requires the hydrolysis of significant amounts of ATP. A major subgroup of molecular chaperones includes three families of proteins whose functions are required for many individual polypeptides to acquire proper, folded, conformation. These three families are named after individual heat shock proteins and are identified as: Hsp70, a polypeptide of about 70 kD (kilodaltons) molecular weight; Hsp60, a component of a large complex; and Hsp90, whose role is more specifically restricted to interacting with certain transcription factors.

According to the present invention, heat shock proteins of particular interest are the cytosolic proteins of the Hsp70 family, Hsp70 and Hsc70. Hsp70 and Hsc70 are known to function in a similar manner and, as described herein, are regulated either by inhibition or enhancement of their cellular activity by one or more molecular accessory chaperone cofactors. Several chaperone cofactors have been previously identified and are known to regulate the binding of substrates to the heat shock proteins such as Hsc70 and Hsp70. For example, chaperone cofactor Hsp40, is known to enhance the forward reaction cycle of Hsc70 by increasing ATPase activity and promoting the formation of the ADP-bound, high substrate-affinity Hsc70 conformation (Minami et al., *J. Biol. Chem.*, 271:19617–19624 (1996)). Additionally, the Hsc70-Interacting Polypeptide ("HIP") is also known to stabilize ADP-bound Hsc70 (Höhfeld et al., *Cell*, 83:589–598 (1995)). Both HIP and Hsp40are capable of positively regulating the binding of substrates and hence the formation of protein—protein complexes by enhancing heat shock protein mediated refolding.

In contrast to the enhancing properties of HIP and Hsp40, the anti-apoptotic polypeptide BAG-1 has been demonstrated to facilitate the reverse reaction cycle by promoting the exchange of ATP for ADP and the release of substrate (Höhfeld et al., *EMBO J.*, 16:6209–6216 (1997)). BAG-1 therefore opposes the actions of HIP and Hsp40 and attenuates Hsc70 chaperone activity (FIG. 8). As used herein, the "reverse reaction cycle" refers to an exchange of ATP for ADP and inorganic phosphate and a decreased substrate affinity. Thus, whereas HIP may be considered to antagonize the reverse reaction cycle of the heat shock protein reaction cycle, a negative regulator of the forward reaction cycle has not been previously described.

Described herein is the isolation, characterization, and method of recombinant preparation of a polypeptide according to the present invention. A preferred polypeptide is the carboxyl terminus of Hsc70-Interacting Protein or "CHIP," which has been demonstrated herein to have activity as a negative regulator of heat shock proteins in an ATP-independent manner. That is, the polypeptide exhibits negative regulating activity for the binding of a heat shock protein to a substrate without requiring energy from the hydrolysis of ATP. As demonstrated herein, CHIP negatively regulates heat shock protein ATPase activities and the chaperoning activities of heat shock proteins, such as Hsc70, Hsp70, and Hsp90. As further demonstrated herein, CHIP is highly conserved among species and is readily isolatable, for example, from mammalian tissues, such as striated muscle.

In the adult human, an examination of the tissue distribution of CHIP mRNA in vivo, reveals notable differences in its expression. For example, expression is highest in striated muscle (skeletal muscle and heart), less in the pancreas and brain, and negligible in other tissues. Common features of the highly expressing organs such as skeletal muscle and heart, include a large proportion of terminally differentiated, nonproliferating cells and relatively high levels of metabolic activity. CHIP is also expressed in a developmentally and spatially regulated fashion in the mouse embryo, particularly in the developing nervous system and during the course of cardiac and skeletal myogenesis.

CHIP is a previously undescribed cytoplasmic polypeptide that complexes with heat shock proteins, such as, Hsc70 (GENBANK accession no. Y00371), Hsp70 (GENBANK accession no. M11717), and Hsp90. CHIP is characteristically distinguished by the percent amino acid identity with which it is conserved among species, such as *Drosophila* CHIP (SEQ ID NO: 8), mouse CHIP (SEQ ID NO: 7), and human CHIP (SEQ ID NO: 2) (FIG. 3). As shown herein, in each of these three CHIP sequences, three TPR domains are present. The percent amino acid similarity of these three TPR domains are highly conserved within these species, i.e., at least about 60% similarity and at least about 50% identity. The amino acid sequences in the carboxy-terminus of SEQ ID NOs. 2, 7, and 8 (amino acid residues 210–303) have at least about an 85% similarity and at least about a 70% identity. The CHIP carboxy-terminus is not similar in amino acid sequence to that of any other known polypeptide, e.g., cyclophilins, that interacts with or regulates heat shock proteins, thereby suggesting that the cellular function of CHIP is unique among polypeptides interacting with heat shock proteins.

The presence of multiple TPR domains in hCHIP suggests that hCHIP participates in interactions with other proteins. Employing a yeast two-hybrid system to define potential hCHIP interaction partners (e.g., binding partners) in vivo (see, Example 6), it was determined that both Hsc70 and Hsp70 are the most frequently identified interaction partners. Since interactions of hCHIP with Hsp70 or Hsc70 in the yeast two-hybrid system assay may reflect a nonspecific interaction with polypeptides that misfold in yeast, interactions of this type could represent Hsc70 and Hsp70 chaperone activities rather than functional protein—protein interactions. However, experimental evidence suggests that this is not the case as: 1) these interactions are also detected in vitro with bacterially expressed and in vitro translated hCHIP; 2) the interaction domain of hCHIP contains TPR motifs similar to those of other members of heat shock protein-associated complexes; 3) hCHIP interacts with the carboxy-terminal domain of Hsp70 and Hsc70 in vitro and in vivo, rather than with their substrate-binding domains, which are known to interact with misfolded proteins (Chappell et al., *J. Biol. Chem.*, 262:746–751 (1987)); and 4) CHIP-Hsc70 complexes can be detected in vivo by immunoprecipitation. Thus, based on the interactions observed in vitro and in vivo, it has been determined that hCHIP is a direct interaction partner with heat shock proteins, such as Hsp70 and Hsc70.

As stated above, a preferred polypeptide of the invention contains three tandem TPR domains, and is classified as a member of the TPR-containing polypeptide family. For example, these tandem TPR domains span amino acid residues 26–59, 60–93, and 94–127 of any of SEQ ID NOs. 2, 7, and 8, and are similar to such domains in other chaperone cofactors. As experimentally established by CHIP's ability to negatively regulate the forward reaction cycle of Hsp70, Hsc70, and Hsp90, and accessory activity of chaperone cofactors, such as Hsp40, Hip, and the Hsc70–Hsp90-Organizing Protein (HOP), CHIP is the first described negative regulator polypeptide of the binding of heat shock proteins to a substrate. Without being bound by any particular theory or mechanism, CHIP is thought to negatively act on the forward reaction cycles of heat shock proteins by establishing a low substrate-affinity conformation. This is in contrast to HIP and Hsp40 chaperone cofactors that positively act on the forward reaction cycles of heat shock proteins, such as Hsp70 and Hsc70, which favors the ADP-bound state and high-substrate affinity conformation.

The preferred polypeptide of the invention has been identified as having an apparent molecular weight of about 30 kD to about 40 kD, more preferably a molecular weight of about 33 kD to about 37 kD, and most preferably about 35 kD, as determined by SDS-polyacrylamide gel electrophoresis. A preferred polypeptide of the invention has greater than about 40% amino acid sequence identity to that of at least one of SEQ ID NOs. 2, 7, and 8, and preferably has at least 50% sequence identity.

Human CHIP ("hCHIP") (SEQ ID NO: 1) can be isolated from striated muscle, such as a human heart cDNA library, using nucleic acid having nucleic acid identity to a TPR containing nucleic acid, such as human CyP-40. Homologous mouse and *Drosophila* cDNAs can be identified in a similar manner. For example, expressed sequence tag (EST) clones for mouse and *Drosophila* are also readily available from GENBANK databases (Example 1). Positive clones for all CHIP species can be identified by employing suitable hybridization conditions or genetic database search parameters described herein. Positive clones can be identified, for example, from a human heart cDNA library employing a suitable probe such as a CyP-40 cDNA or fragment thereof. These clones can then be isolated and the open reading frame (ORF) of the nucleotides associated with the negative regulation of ATPase activity and chaperone, activities of heat shock proteins can be identified (Examples 11 and 12). An exemplary assay for assessing the regulatory activity of CHIP clones is provided in Example 6.

The complete open reading frame (ORF) of the hCHIP polypeptide spans an area of 909 base pairs of the full-length nucleic acid (1286 base pairs, SEQ ID NO: 1) predicting a mature polypeptide of about 303 amino acids (SEQ ID NO: 2). Exemplary nucleotides encoding hCHIP, mCHIP, and *Drosophila* CHIP polypeptides are provided in FIGS. 1, 9, and 10. The amino acid sequences of these polypeptides are also provided in FIG. 3 (SEQ ID NOs. 2, 7, and 8). The human CHIP genomic nucleic acid is shown in FIG. 11 (SEQ ID NO: 11).

Using SEQ ID NO: 2, the amino acid sequence of the hCHIP polypeptide was shown to have limited sequence identity and similarity in the GENBANK or SWISS PROT databases to other polypeptides in the conserved tandem TPR domains, e.g., about 35% to about 40% amino acid identity, and about 50% to about 60% amino acid similarity. The nucleic acid for *Drosophila* CHIP (SEQ ID NO: 10), human CHIP (SEQ ID NO: 1), and mouse CHIP (SEQ ID NO: 9), have been deposited into GENBANK and have been assigned the nucleotide accession numbers AF129084, AF129085, and AF129086, respectively.

The full-length nucleic acid encoding a polypeptide according to the present invention can be inserted into an expression system employing an expression vector. The recombinant polypeptide can be isolated as described in the examples (Example 5). Those of ordinary skill in the art recognize that, given a particular nucleic acid sequence such as that provided in any one of SEQ ID Nos. 1, 9, 10, and 11, there are a variety of expression systems that could be used for expression of the nucleic acid. As used herein, a "nucleic acid vector," "expression vector," or "expression cassette" is a replicon, or a genetic element that functions as an autonomous unit of nucleic acid, either DNA or RNA, replication in vivo and capable of replication under its own control, such as a plasmid, a chromosome, a virus, phage, or cosmid. Another nucleic acid may be attached to the replicon or genetic element so as to bring about the replication of the attached nucleic acid. Additionally, nucleic acids according to the present invention, can be introduced into expression cassettes, which, when expressed in a host, provide "antisense" nucleic acid transcripts.

Accordingly, the present invention provides a nucleic acid fragment in a nucleic acid vector and a method of using the nucleic acid fragment wherein the nucleic acid fragment encodes a polypeptide, the presence of which is associated with negative regulation of a heat shock protein, and further wherein the method provides for expressing the nucleic acid fragment in a host cell that is transformed with an expression vector having the nucleic acid fragment operably linked to control sequences recognized by the host cell.

Expression cassettes or expression vectors for host cells ordinarily include an origin of replication, a promoter located upstream from the coding region, together with a ribosome binding site, a polyadenylation site, and a transcriptional termination sequence. Those of ordinary skill will appreciate that some of the aforementioned sequences are not required for expression in certain hosts. For example, an expression vector for use with bacteria need only contain an origin of replication recognized by the host, a promoter that will function in the host and a selection nucleic acid.

Furthermore, there are a variety of methods known in the art that could be used to produce and isolate the polypeptide of this invention, and those of ordinary skill in the art also recognize that several assays described herein, including the yeast-two hybrid screen (Example 6) and the in vitro binding assays (Example 7), will determine whether or not a particular expression system, in addition to those expression systems provided in the examples, is functioning, without requiring undue experimentation. A variety of molecular and immunological techniques can be found in basic technique texts such as those of Sambrook et al., *Molecular Cloning, A Laboratory Manual*, Cold Spring Harbor Laboratory Press, Cold Spring Harbor, N.Y. (1989), and Harlow et al., *Antibodies: A Laboratory Manual*, Cold Spring Harbor Laboratory Press, Cold Spring Harbor, N.Y. (1988).

Transformation may be by any known method for introducing nucleic acids into a host cell, including, for example, packaging the nucleic acid in a virus and transducing a host cell with the virus, and by direct uptake of the nucleic acid. The terms "transformed" or "transformation" or "stably transformed", as used herein, refer to the insertion of a nucleic acid into a host cell, irrespective of the method used for the insertion, for example, direct uptake, transduction, f-mating, or electroporation. The nucleic acid may be maintained as a non-integrated vector, for example, a plasmid, or alternatively, may be integrated into the host genome. A cell has been "transformed" by a nucleic acid when such nucleic acid has been introduced into the cell membrane. According to the present invention, a nucleic acid may or may not be integrated (covalently linked) to chromosomal DNA making up the genome of the cell. In prokaryotes and yeast, for example, the nucleic acid may be maintained on an episomal element such as a plasmid. With respect to eukaryotic cells, a stably transformed cell is one in which the nucleic acid has become integrated into a chromosome so that it is inherited by daughter cells through chromosomal replication. This stability is demonstrated by the ability of the eukaryotic cell to establish cell lines or clones that include a population of daughter cells containing the nucleic acid.

The transformation procedure used depends upon the host to be transformed. Bacterial transformation by direct uptake generally employs treatment with calcium or rubidium chloride (Cohen, *Proc. Natl. Acad. Sci. USA*, 69:2110–2114 (1972)). Yeast transformation by direct uptake may be carried out using the method of Hinnen et al., *Proc. Natl. Acad. Sci.*, 75:1929–1933 (1978). Mammalian transformations by direct uptake may be conducted using the calcium phosphate precipitation method of Graham and Van der Eb, *Virology*, 52: 456–467 (1973), or the various known modifications thereof. Other methods for the introduction of recombinant nucleic acids into cells, particularly into mammalian cells, that are known in the art include dextran-mediated transfection, calcium phosphate mediated transfection, polybrene mediated transfection, protoplast fusion, electroporation, encapsulation of the nucleic acid(s) in liposomes, and direct microinjection of the nucleic acids into nuclei.

The control sequences that are suitable for prokaryotic cells, for example, include a promoter and optionally an operator sequence, and a ribosome binding site. A "promoter" or "promoter sequence" is a DNA regulatory region to which RNA polymerase binds and initiates transcription of a downstream (3' direction) coding sequence. For purposes of defining the present invention, the promoter sequence is bounded at its 3' terminus by the translation start codon of a coding sequence and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences.

Eukaryotic cells are known to utilize promoters, polyadenylation signals and enhancers. Expression control sequences for prokaryotes include promoters, optionally containing operator portions and ribosome binding sites. Among prokaryotic hosts, including gram negative and gram positive organisms, *E. coli* is most frequently used. A number of prokaryotic expression vectors are known in the art. See, for example, U.S. Pat. No. 4,440,859 (Rutter et al.) and U.S. Pat. No. 4,436,815 (Hershberger et al.).

Nucleic acid vectors compatible with prokaryotic hosts are commonly derived from pBR322, a plasmid containing operons conferring ampicillin and tetracycline resistance, and various pUC vectors, which also contain sequences conferring antibiotic resistance markers. These markers may be used to obtain successful transformants by selection.

Commonly used prokaryotic control sequences include the Beta-lactamase (penicillinase) and lactose promoter systems 275:617 (1978); Itakura et al., *Science*, the tryptophan (trp) promoter system (Goeddel et al., *Nucleic Acids Res.*, 8: 4057–4074 (1980)) and the lambda-derived $P_L$ promoter and N gene ribosome binding site (Shimatake et al., *Nature* 292:128–132 (1981)) and the hybrid tac promoter (De Boer et al., *Proc. Natl. Acad. Sci. USA*, 80:21–25 (1983)) derived from sequences of the trp and lac UV5 promoters. The foregoing systems are particularly compatible with *E. coli*. If desired, other prokaryotic hosts such as strains of *Bacillus* or *Pseudomonas* may be used with appropriate control sequences. Although the promoters cited above are commonly used, other microbial promoters know in the art, are also suitable.

For routine vector constructions, ligation mixtures are transformed into *E. coli* strain HB101 or other suitable host, and successful transformants selected by antibiotic resistance or other markers. Plasmids from the transformants are then prepared according to the method of Clewell et al., *Proc. Natl. Acad. Sci. USA*, 62:1159–1166 (1969), usually following chloramphenicol amplification (Clewell, *J. Bacteriol.*, 110: 667–676 (972)). The DNA is isolated and analyzed, usually by restriction enzyme analysis and/or sequencing. Sequencing may be by the dideoxy method of Sanger et al., *Proc. Natl. Acad. Sci. USA*, 74: 5463–5467 (1977) as further described by Messing et al., *Nucleic Acids Res.*, 9:309–321 (1981), or by the method of Maxam et al., *Methods in Enzymology*, 65:499–560 (1980). Problems with band compression, which are sometimes observed in GC rich regions, are overcome by use of 7-deazoguanosine according to Barr et al., *Biotechniques*, 4:428–432 (1986).

Eukaryotic hosts include yeast and mammalian cells in culture systems. *Saccharomyces cervisiae* and *Saccharomy-* ces carlsbergensis are the most commonly used yeast hosts and are convenient fungal hosts. Yeast compatible vectors carry markers which permit selection of successful transformants by conferring prototrophy to auxotrophic mutants or resistance to heavy metals on wild-type strains. Yeast compatible vectors may employ the 2 micron origin of replication (Broach, Meth. Enz,. 101:307–325 ((1983)), the combination of CEN3 and ARS1 or other means for assuring replication, such as sequences which will result in incorporation of an appropriate fragment into the host cell genome.

Control sequences for yeast vectors are known in the art and include promoters for the synthesis of glycolytic the promoter for 3 phosphoglycerate kinase (Hitzeman et al., J. Biol. Chem., 255:12073–12080 (1980)). Terminators may also be included, such as those derived from the enolase gene (Holland et al., J. Biol. Chem., 256: 1385–1395 (1981)). Particularly useful control systems are those that comprise the glyceraldehyde-3 phosphate dehydrogenase (GAPDH) promoter or alcohol dehydrogenase (ADH) regulatable promoter, terminators also derived from GAPDH, and if secretion is desired, leader sequence from yeast alpha factor.

In addition, an operably linked transcriptional regulatory region and transcriptional initiation region do not have to be ones that are naturally associated in a wild-type organism. Other yeast promoters, which have the additional advantage of transcription controlled by growth conditions, are the promoter regions for alcohol dehydrogenase 1 or 2, isocytochrome C, acid phosphatase, as well as enzymes responsible for maltose and galactose utilization.

Mammalian cell lines available as hosts for expression are known in the art. Suitable host cells for expressing CHIP in higher eukaryotes include the following: monkey kidney CVI line transformed by SV40 (COS-7, ATCC CRL 1651); baby hamster kidney cells (BHK, ATCC CRL 1651): Chinese hamster ovary-cells-DHFR (described by Urlaub and Chasin, PNAS, 77:4216–4220 (1980, USA)); mouse sertoli cells (TM4, Mather, Biol. Reprod., 23:243–252 (1980)); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A ATCC CRL 1442); human lung cells (W138, ATCC CCL 75); human liver cells (Hep G2 HB 8065); mouse mammary tumor (MMT 060652, ATCC CCL 51); rat hepatoma cells (HTC. M1. 54, Baumann et al., J. Cell Biol., 85:1–8 (1980) and TR1 cells (Mather et al., Annals N.Y. Acad. Sci., 383:44–68 (1982)).

Suitable promoters for mammalian cells are also known in the art and include viral promoters such as that from Simian Virus 40 (SV40) (Fiers et al., Nature, 273:113–120 (1978)), Rous sarcoma virus (RSV), adenovirus (ADV), and bovine papilloma virus (13PV). Mammalian cells may also require terminator sequences and poly A addition sequences. Enhancer sequences that increase expression can also be included, and sequences which cause amplification of the gene may also be desirable. These sequences are known in the art. It will be appreciated that when expressed in mammalian tissue, a recombinant polypeptide according to the present invention may have higher molecular weight due to glycosylation or phosphorylation. It is therefore intended that partially or completely glycosylated forms of phosphorylated forms of the preferred CHIP, for example, having molecular weights greater than provided by the amino acid back-bone are within the scope of this invention.

Vaccinia virus may be used to express foreign DNA and may be used in an inhibitory preparation according to the present invention. In this case the heterologous DNA is inserted into the Vaccinia genome. Techniques for the insertion of foreign DNA into the vaccinia virus genome are known in the art, and use, for example, homologous recombination. The insertion of the heterologous DNA is generally into a gene that is non-essential in nature, for example, the thymidine kinase gene (tk), which also provides a selectable marker. Plasmid vectors that greatly facilitate the construction of recombinant viruses have been described (see, for example, Mackett et al., J. Virol. 49: 857–264 (1984); Chakrabarti et al., Mol. Cell Biol. 5: 3403–3409 (1985); and Moss, Gene Transfer Vectors for Mammalian Cells, Miller and Calos, eds., Cold Spring Harbor Laboratory, Cold Spring Harbor, N.Y., p. 10–14 (1987)). Expression of a polypeptide according to the invention then occurs in cells or mammalian subjects, e.g., humans, that are immunized with the live recombinant vaccinia virus.

Other systems for expression of eukaryotic or viral genomes include insect cells and vectors suitable for use in these cells. These systems are known in the art, and include, for example, insect expression transfer vectors derived from the baculovirus Autographa californica nuclear polyhedrosis virus (AcNPV), which is a helper-independent, viral expression vector. Expression vectors derived from this system usually use the strong viral polyhedrin gene promoter to drive expression of heterologous genes. Currently the most commonly used transfer vector for introducing foreign genes into AcNPV is pAc373. The vector pAc373 also contains the polyhedrin polyadenylation signal and the ampicillin-resistance (amp) gene and origin of replication for selection and propagation in E. coli. Many other vectors, known to those of skill in the art, have also been designed for improved expression. These include, for example, pVL985 (which alters the polyhedrin start codon from ATG to ATT, and which introduces a BamHI cloning site 32 base pairs downstream from the ATT. (See, e.g., Luckow and Summers, Virology—170:31–39, (1989)). Good expression of nonfused foreign proteins usually requires foreign genes that ideally have a short leader sequence containing suitable translation initiation signals preceding an ATG start signal.

Methods for the introduction of heterologous DNA into the desired site in the baculovirus virus are known in the art. (See, e.g., Smith et al., Mol. & Cell Biol., 3: 2156–2165 (1983); and Luckow and Summers, Virology,—170:31–39 (989)). For example, the insertion can be into a gene such as the polyhedrin gene, by homologous recombination. Insertion can also be into a restriction enzyme site engineered into the desired baculovirus gene. The inserted sequences may be those which encode all or varying segments of the polypeptide, or other ORFs which encode viral polypeptides.

The signals for posttranslational modifications, such as signal peptide cleavage, proteolytic cleavage and phosphorylation, appear to be recognized by insect cells. The signals required for secretion and nuclear accumulation also appear to be conserved between the invertebrate cells and vertebrate cells. Examples of the signal sequences from vertebrate cells which are effective in invertebrate cells are known in the art, for example, the human interleukin 2 signal ($IL2_s$) which is a signal for transport out of the cell, is recognized and properly removed in insect cells.

As stated above, a preferred polypeptide of this invention has an apparent molecular weight as determined by SDS-PAGE of about 30 kD to about 40 kD. Exemplary polypeptides are provided by SEQ ID NOs. 2, 7, and 8. Those of ordinary skill in the art will recognize that some variability in amino acid sequence identity is expected and that this variability should not detract from the scope of this invention. For example, conserved mutations do not detract from this invention nor do variations in amino acid sequence identity of less than about 40% amino acid sequence identity, for example, where the polypeptide is capable of negatively regulating the binding of a substrate to a heat shock protein.

Some nucleotide sequence variability is observed among the species as is some amino acid variability (FIGS. 1, 2, 3, 9, and 10). Conserved amino acid substitutions are known in the art and include, for example, amino acid substitutions using other members from the same class to which the amino acid belongs. For example, the nonpolar (hydrophobic) amino acids include alanine, leucine, isoleucine, valine, proline, phenylalanine, tryptophan, and tyrosine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Such alterations are not expected to affect apparent molecular weight as determined by polyacrylamide gel electrophoresis or isoelectric focusing point. Particularly preferred conservative substitutions include, but are not limited to, Lys for Arg to maintain a positive charge, Glu for Asp to maintain a negative charge, Ser for Thr so that a free —OH is maintained, and Gln for Asn to maintain a free $NH_2$.

Preferred polypeptides of the invention include polypeptides with the amino acid sequences of any one of SEQ ID NOs. 2, 7, and 8. Other polypeptides include those polypeptides capable of negatively regulating binding or complexing of a heat shock protein to a substrate by any one of several possible mechanisms, which include but are not limited to, reducing or inhibiting heat shock protein ATPase activity, inhibiting or reducing binding of one or more accessory chaperone cofactors to the heat shock protein, and/or by the direct binding or complexing of the heat shock protein with a polypeptide of the present invention (preferably, CHIP).

A nucleic acid fragment encoding the polypeptide of the invention preferably hybridizes under stringent hybridization conditions to at least one of SEQ ID NOs. 1, 9, 10, and 11 or a complement thereof. "Hybridization under stringent conditions" refers to those conditions that employ low ionic strength and high temperature for washing, for example, (1) 0.015 M NaCl/0.0015 M sodium citrate (SSC) about 0.1% sodium dodecyl sulfate (SDS) at about 50° C. to about 65° C.; or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 50° C. to about 65° C. Another example (3) is the use of 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC and 0.1% SDS. The term "hybridization" or "hybridize" as used herein refers to the process by which a single-stranded nucleic acid joins with a complementary strand of nucleic acid through nucleotide base pairing.

A polypeptide of the invention also can include an active analog or active fragment of any one of SEQ ID NOs. 2, 7, and 8. For example, it can be a polypeptide containing amino acid residue 1 to amino acid residue 303 of any one of SEQ ID NOs. 2, 7, and 8. An active analog or active fragment preferably is characterized by negative regulating activity properties with respect to a heat shock protein similar to the negative regulating activity properties of the polypeptides shown in any one SEQ ID NOs. 2, 7, and 8.

An active analog of any one of SEQ ID NOs. 2, 7, and 8 of the invention includes a polypeptide having one or more amino acid residue substitutions that do not eliminate negative regulating activity for a heat shock protein. For example, an active analog of the invention can be characterized by the ability to interfere with heat shock protein ATPase activity.

Nucleic acid fragments encoding of a polypeptide, such as CHIP, are also part of this invention. Any one of SEQ ID NOs. 1, 9, 10, and 11 are preferred nucleic acids encoding a polypeptide of the invention. Those of ordinary skill in the art will recognize that some substitution of the nucleotide sequence will not alter a nucleic acid fragment to an extent that the character or nature of the nucleic acid fragment is substantially altered. For example, a nucleic acid fragment with a nucleic acid identity of at least about 60% of at least one of SEQ ID NOs. 1, 9, 10, and 11, is contemplated to be within the scope of this invention. A method for determining whether a particular nucleic acid fragment falls within the scope of this invention is to consider whether or not a particular nucleic acid fragment encodes a polypeptide of the invention, preferably CHIP, and preferably has a nucleic acid identity of at least about 60% as compared with at least one of SEQ ID NOs. 1, 9, 10, and 11.

The terms "complement nucleic acid" and "complementary nucleic acid" as used herein, refer to a nucleic acid fragment that is capable of hybridizing to a specified nucleic acid fragment, particularly under stringent hybridization conditions. "Complementary," further refers to the capacity of purine and pyrimidine nucleotides to associate through hydrogen bonding in double stranded nucleic acid molecules. The following base pairs are complementary: guanine and cytosine; adenine and thymine; and adenine and uracil.

It is further contemplated that complementary nucleic acid includes "antisense" nucleic acid sequences of the nucleic acid encoding a polypeptide, preferably a CHIP, according to the present invention. Antisense nucleic acid is defined as a non-coding sequence that is "complementary" to all or at least a portion of at least one of SEQ ED NOs. 1, 9, 10, and 11. For example, the complementary nucleic acid or antisense sequence for 5'-ATGTC-3' is 3'-TACAG-5'.

Other nucleic acids encoding a polypeptide of the invention include those with some degeneracy with respect to the nucleotide sequence. A degenerate codon means that a different three letter codon is used to specify the same amino acid. For example, it is well known in the art that the following RNA codons (and therefore, the corresponding DNA codons, with a T substituted for a U) can be used interchangeably to code for each specific amino acid:

| | |
|---|---|
| Phenylalanine (Phe or F) | UUU, UUC, UUA or UUG |
| Leucine (Leu or L) | CUU, CUC, CUA or CUG |
| Isoleucine (Ile or I) | AUU, AUC or AUA |
| Methionine (Met or M) | AUG |
| Valine (Val or V) | GUU, GUC, GUA, GUG |
| Serine (Ser or S) | AGU or AGC |
| Proline (Pro or P) | CGU, CCC, CCA, CCG |
| Threonine (Thr or T) | ACU, ACC, ACA, ACG |
| Alanine (Ala or A) | GCU, GCG, GCA, GCC |
| Tryptophan (Trp) | UGG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |

-continued

| | |
|---|---|
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | AGA or AGG |
| Glycine (Gly or G) | GGU or GGC or GGA or GGG |
| Termination codon | UAA, UAG or UGA |

Furthermore, a particular nucleic acid can be modified to employ the codons preferred for a particular cell type. For example, preferred codon usage for *E. coli* is known, as are preferred codons for animals including *Drosophila*, mice and humans. These changes are known to those of ordinary skill in the art and therefore these nucleic acids are considered part of this invention. Other nucleotide sequences include nucleotide fragments of at least 12 nucleic acids in length from at least one of SEQ ED NOs. 1, 9, 10, and 11, preferably nucleic acid fragments of at least 17 nucleic acids in length, where these fragments hybridize to at least a portion of at least one of SEQ ID NOs. 1, 9, 10, and 11, under stringent hybridization conditions. The nucleic acids of this invention can encode all, none (e.g., fragments that cannot be transcribed, fragments that include regulatory portions of the gene, or the like) or a fragment of at least one of SEQ ID NOs. 2, 7, and 8, and preferably contain a contiguous nucleic acid fragment that encodes at least about 197 amino acids from at least one of SEQ ID NOs. 2, 7, and 8. Because nucleic acid fragments encoding a portion of a CHIP are contemplated in this invention, it will be understood that not all of the nucleic acid fragments will encode a polypeptide capable of negatively regulating binding or complexing of a heat shock protein to a substrate. Furthermore, the nucleic acid of this invention can be mutated to remove or otherwise inactivate the negative regulating activity of the polypeptide. Therefore, amino acid fragments without negatively regulating activity that meet the hybridization requirements described above are also contemplated. Methods for mutating or otherwise altering nucleic acids are well described in the art and the production of an inactive polypeptide can be tested for activity as described herein.

The nucleic acid fragments of this invention can be incorporated into vectors or stably incorporated into host genomes to produce recombinant polypeptides including recombinant chimeric polypeptides. In one embodiment, the polypeptide of the invention is encoded by a nucleic acid fragment in a vector and the vector is in a cell. Preferably, the cell is a prokaryotic cell such as a bacterium, or a eukaryotic cell from yeast, or *Drosophila* or baculovirus. The nucleic acid fragments can exist as the fusion of all or a portion of the nucleic acid of a preferred CHIP with another nucleic acid fragment, and the polypeptide of the invention can exist as a fusion polypeptide, such as a glutathione S-transferase (GST) polypeptide (Example 5), of one or more polypeptides wherein the fusion polypeptide is expressed as a single polypeptide. A variety of nucleic acid vectors of this invention are known in the art and include a number of commercially available expression plasmids or viral vectors. The use of these vectors is well within the scope of what is ordinary skill in the art. Exemplary vectors are employed in the examples, but should not be construed as limiting on the scope of this invention.

Inhibitors and methods of preparing inhibitors that can be employed in an inhibitory composition directed to a polypeptide or a nucleic acid of the invention are also contemplated in the present invention. As used herein, the term "inhibitor composition," refers to a composition or preparation administered in an amount, preferably a therapeutically effective amount, that is effective to treat and/or prevent a disease. A "disease" as used herein, refers to diseases such as a neoplastic disease, which includes such diseases as cancer and lymphoma, an ischemic disease, which includes such diseases as stroke, vascular disease, and myocardial infarction, or a disease characterized by inflammation, which includes infections and autoimmune diseases, in a mammal diagnosed with such a disease. Preferably, the inhibitory composition further provides some therapeutic benefit or effect so as to result in a response that inhibits, reduces, or prevents the disease in a mammal so treated by interfering with the negative regulating activity of a polypeptide of the invention. Both local and systemic administration is contemplated. Systemic administration is preferred.

The inhibitory compositions are often mixed with excipients or diluents that are pharmaceutically acceptable as carriers and compatible with the active ingredient. The term "pharmaceutically acceptable carrier" refers to a carrier(s) that is "acceptable" in the sense of being compatible with the other ingredients of a composition and not deleterious to the recipient thereof. Suitable excipients are, for example, water, saline, dextrose, glycerol, ethanol, or the like and combinations thereof. In addition, if desired, the inhibitory composition may contain minor amounts of auxiliary substances such as wetting or emulsifying agents, pH buffering agents, and/or adjuvants which enhance the effectiveness of the inhibitory composition.

Examples of adjuvants or carriers that may be effective include but are not limited to: aluminum hydroxide, N-acetyl-muramyl-L-threonyl-D-isoglutamine (thr-MDP); N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

An inhibitor directed to a polypeptide or nucleic acid, i.e., sense or antisense nucleic acids, of the invention is preferably administered to a mammal to provide a response specific for the polypeptide or nucleic acid, including the polypeptide encoded by the nucleic acid or its complement. The inhibitory compositions of the present invention are conventionally administered parenterally, by injection, for example, either subcutaneously or intramuscularly either as liquid solutions or suspensions. Solid forms suitable for suspension in a liquid vehicle prior to injection or infusion can also be prepared. Additional formulations that are suitable for administration include oral formulations. Oral formulations include such normally employed excipients as, for example, pharmaceutical grades of mannitol, lactose, starch, magnesium stearate, sodium saccharine, cellulose, magnesium carbonate and the like. Polypeptides of the invention may be formulated into an inhibitory composition as neutral or salt forms. These compositions take the form of solutions, suspensions, tablets, pills, capsules, sustained release formulations or powders and contain about 10%–95% of active ingredient, preferably about 25%–70%.

Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium, or ferric hydroxides and such organic bases as isopropylamine, trimethylamine, ethylamino ethanol, histidine, procaine, and the like.

Inhibitory compositions comprising sense or antisense nucleic acids, or inhibitors of polypeptides of the instant invention, are typically administered to a mammal, e.g., human, in a manner compatible with the dosage formulation, and in such amount as will be prophylactically and/or therapeutically effective and result in a response that is specific for a polypeptide of the invention. It is very common to express dosage units in mg/kg (i.e., mg/kg of body weight) or, if a continuing series of doses over many days is contemplated, mg/kg/day. An inhibitory composition of the invention will usually contain an effective amount, e.g., an amount capable of eliciting a response in a mammal, of an inhibitor to a polypeptide of the invention in conjunction with a conventional, pharmaceutically acceptable carrier. The dosage will vary depending upon the specific purpose for which the polypeptide is being administered. The prepared compounds and compositions can be administered to mammals.

This invention also relates to an antibody capable of binding specifically to a polypeptide according to the present invention. A polyclonal or monoclonal antibody can be prepared to a portion of or to the full-length polypeptides represented by SEQ ID NOs. 2, 7, and 8, for example. Methods for preparing antibodies to polypeptides are well known and well described, for example, by Harlow et al., *Antibodies: A Laboratory Manual*, Cold Spring Harbor, N.Y.; Cold Spring Harbor Laboratory Press (1988). In a preferred example, the antibodies can be human derived, rat derived, mouse derived, or rabbit derived. Polypeptide-binding antibody fragments and chimeric fragments are also known and are within the scope of this invention.

The present invention also includes a method for identifying and isolating an inhibitor of a polypeptide of the invention. The method includes identifying an inhibitor that inhibits the negative regulating activity of the polypeptide by incubating the polypeptide with the inhibitor under conditions that promote the negative regulating activity of the polypeptide and determining if the negative regulating activity of the polypeptide is reduced relative to the negative regulating activity of the polypeptide in the absence of the inhibitor or by using such an agent to exert the same effect in vivo.

Objects and advantages of this invention are further illustrated by the following examples, but the particular materials and amounts thereof recited in these examples, as well as other conditions and details, should not be construed to unduly limit this invention.

EXAMPLES

Example 1 cDNA Cloning of Human, Mouse, and *Drosophila* Carboxyl Terminus of Hsc70 Interacting Protein (CHIP)

A nucleic acid fragment corresponding to nucleotides 721–1150 of the human cyclophilin 40 (CyP-40) cDNA was radiolabeled with [α-$^{32}$P]dCTP (New England Nuclear, Cambridge, Mass.) and used to screen a phage library of human heart cDNA in the vector λgt11 (Clontech, Palo Alto, Calif.) as described by Patterson et al., *J. Biol. Chem.* 270:23111–23118 (1995). Phage colonies were grown on agarose and transferred to nitrocellulose membranes. Phage colonies that hybridized preferentially under low-stringency conditions (0.2×SSC, 0.1% SDS at 42° C.) but not high-stringency conditions (0.2×SSC, 0.1% SDS at 55° C.) final washes were analyzed and characterized. A total of 12 colonies were characterized by plaque isolation, amplification and sequencing, and it was determined that eight colonies contained human CyP-40 cDNA sequences, and four colonies encoded a novel cDNA having no sequence identity to known genes available in GENBANK. The novel cDNA was analyzed using BLAST 2.0 SEQUENCES at National Center for Biotechnology Information (NCBI) website on the world wide web at ncbinlm.nih.gov. and GENBANK databases.

The following human expressed sequence tag EST) sequences (available from GENBANK EST database) were found to be identical to the cDNA sequence of the novel cDNA obtained by phage screening; Clone ID Nos: 548268, 177869, and 647520. Clones 548268 and 177869 contained polyadenylated sequence at the 3' end. Plasmids containing these EST sequences were obtained from Genome Systems, Inc, St. Louis, Mo. The 5' end of the cDNA was defined by 5' rapid amplification of cDNA ends using human heart mRNA and primers designed on the basis of EST sequences: GCTGTAAGCTCGCTGCAGAT (SEQ ID NO: 14), and GCCTCATCATAGCTCTCCATCTC (SEQ ID NO: 15). Products of these reactions, as well as plasmids containing the EST fragments, were sequenced as described by Patterson et al., *J. Biol. Chem.* 270:23111–23118 (1995), and a single contiguous human cDNA sequence was assembled. Homologous mouse (SEQ ID NO: 9) and *Drosophila* cDNAs (SEQ ID NO: 10) were identified in a similar manner, based on EST clones ID Nos. 525111 and 846365 (mouse) and clone ID No. LD 16049 (*Drosophila*). Sequence comparisons were made using GENEWORKS 2.5.1 software using the CLUSTRAL alignment default parameters (IntelliGenetics, Inc., Campbell, Calif.).

Example 2

Cell Culture and mRNA Isolation

Saos-2 human osteosarcoma, cells (Accession No. HTB-85), HeLa human epidermoid carcinoma cells (Accession No. CCL-2), HepG2 human hepatoma cells (Accession No. HB-8065), human fibroblasts (Accession No. CRL-7282), U937 human histiocytic lymphoma cells (Accession No. HB-172), RD human embryonal rhabdomyosarcoma, cells (Accession No. CCL-136), IM9 human lymphoblastoid cells (Accession No. CCL-159), HCN-1A human neuronal cells (Accession No. CRL-10442), and COS-7 monkey kidney-derived cells (Accession No. CRL-1651) were obtained from the American Type Culture Collection, Bethesda, Md. Primary-culture human skeletal muscle and aortic smooth muscle cells were obtained from Clonetics Corp., Walkersville, Md. Primary-culture human umbilical vein endothelial cells were also obtained from Clonetics and were grown in Endothelial Growth Medium containing 2% fetal calf serum (Clonetics, Walkersville, Md.). All other cell types were cultured in Dulbecco's modified Eagle's medium supplemented with 10% fetal calf serum (Gibco, Rockville, Md.) as described in Patterson et al., *J. Biol. Chem.*, 270:23111–23118 (1995). Similarly, the total RNA from cells in culture was prepared by guanidinium isothiocyanate extraction and centrifugation through cesium chloride as described by Patterson et al., *J. Biol. Chem.*, 270:23111–23118 (1995).

Example 3

Northern Blot Analysis

RNA blots were hybridized as described by Patterson et al., *J. Biol. Chem.* 270:23111–23118 (1995). The total RNA, 10 micrograms (µg), from cells in culture was fractionated on a 1.3% formaldehyde-agarose gel and transferred to a nitrocellulose filter. Multiple tissue Northern blots were purchased from Clontech, Palo Alto, Calif. Full-length hCHIP and β-actin cDNAs (Courtesy of Tom Quertermous, Stanford, Calif.) were labeled with $^{32}P$ by random priming and used to hybridize filters. Filters were autoradiographed for 16 hours at –80° C. on Kodak XAR film (Eastman Kodak, Rochester, N.Y.).

Example 4

Intracellular Localization

Three plasmid constructs were prepared. A full-length hCHIP cDNA (SEQ ID NO: 1) was inserted into the green fluorescent protein (GFP) fusion vector pEGFP-C3 (Clontech, Palo Alto, Calif.) to create the plasmid pEGFP-CHIP. Additionally, plasmid pEGFP-GKLF expressing amino acid fragment 400–483 of GKLF (GenBank U20344) of the gut-enriched Krüppel-like factor (GKLF) as a fusion with GFP, was provided by Janiel M. Shields (The Johns Hopkins University School of Medicine, Baltimore, Md.) and served as a control for nuclear localization. Plasmid pEGFP-C3, expressing GFP alone, served as a control for nonlocalized expression. Two µg of each plasmid were transfected into COS-7 monkey kidney-derived cells obtained from the American Type Culture Collection, Bethesda, Md. (Accession No. CRL-1651) by the Lipofectin method (Life Technologies, Rockville, Md.) as described by Wu et al., *Biochem. J.,* 330:1469–1474 (1998). After 48 hours in the conditions described above, cells were examined for GFP expression by direct epifluorescence using a Nikon DIAPHOT 300 microscope (Nikon, Melville, N.Y.)

Example 5

In vitro Transcript ion/Translation and Recombinant Polypeptide Production $^{35}S$-labeled in vitro-transcribed and translated proteins were produced using a T7-antisense hCHIP coding region or T3 sense hCHIP coding region-coupled rabbit reticulocyte lysate system (Promega, Madison, Wis.), according to the manufacturer's instructions. To determine the molecular mass at which native hCHIP migrates, clone ID No. 526948, which contains the entire open reading frame (ORF) of the hCHIP cDNA in pBluescript SK, was used. For binding assays, the human CHIP ORF was inserted into vector pCITE-4a (Novagen, Madison, Wis.) as a 43-kD S-tagged fusion to optimize in vitro translation.

The ORF of hCHIP (SEQ ID NO: 2) was inserted in frame into vector pET-30a (Novagen, Madison, Wis.), as a Histagged fusion to create plasmid pET-hCHIP. Glutathione S-transferase (GST) fusions were created by inserting the entire human CHIP ORF or appropriate restriction fragments in frame in vector pGEX KG (Pharmacia, Piscataway, N.J.) to create plasmids pGST-hCHIP (amino acid residues 1–303) pGST-hCHIP (amino acid residues 1–142), pGST-hCHIP (amino acid residues 1–197), pGST-hCHIP (amino acid residues 143–303), and pGST-hCHIP (amino acid residues 198–303). GST fusion plasmids pGEXHsc70 (amino acid residues 1–540 of Hsc70, GENBANK accession number no. Y00371), pGEXsc70 (amino acid residues 373–540, GENBANK accession number no. Y00371), pGEXHsc70 (amino acid residues 373–650, GENBANK accession number no. Y00371), and pGEXHsc70 (amino acid residues 540–650, GENBANK accession number no. Y00371), containing the indicated fragments of Hsc70, were obtained from Ernst Ungewickell (Washington University School of Medicine, St. Louis, Mo.) and have been previously described in Ungewickell et al., *J. Biol. Chem,* 272:19594–19600 (1997).

The plasmid pGEX-2T (Pharmacia, Piscataway, N.J.), expressing GST alone, served as a control. Recombinant polypeptides were expressed in *E. coli* BL21 (Novagen, Madison, Wis.). The cells were grown for 4 hours at 37° C., then 1 millimolar (mM) isopropyl-1-thio β-D-galactopyranoside was added (Novagen, Madison, Wis.). The cells were additionally grown for 5 hours at 37° C., and the *E. coli* cells were then lysed by sonication. GST fusion proteins were purified by affinity chromatography on glutathione-Sepharose 4B (Pharmacia, Piscataway, N.J.) following the manufacturer's instructions. His-tagged recombinant proteins were purified using $Ni^{2+}$ chelation chromatography. Briefly, bacterial lysates were passed over a $Ni^{2+}$ column and bound proteins were eluted in a low-salt buffer (Novagen, Madison, Wis.).

Recombinant BAG-1 (GENBANK, NM 004323) produced in a baculovirus expression system was provided by Jörg Höhfeld (Max Planck Institute, Munich, Germany). Protein concentrations of recombinant proteins were determined by a modified Lowry procedure (DC Protein Assay; Bio-Rad, Oakland, Calif.) and were confirmed by 8% SDS-polyacrylamide gel factionation of samples, followed by Coomassie Blue staining.

Example 6

Yeast Two-hybrid System

A yeast two-hybrid screen was performed according to Gyuris et al., *Cell,* 75:791–803 (1993), using the MATCHMAKER two-hybrid system (Clontech, Palo Alto, Calif.). Full-length hCHIP (SEQ ID NO: 2) was produced as a fusion with the GAL4 DNA-binding domain (GENBANK U57443) in plasmid pAS2–1 (Clontech) and used as a bait, i.e., a polypeptide expressed in yeast that binds potential interaction partners.

A human heart cDNA library in pACT2 (Clontech) which expresses fusions with the GAL4 activation domain, was screened for potential prey, i.e., an interaction partner, in the yeast strain CG-1945. A total of $2.5 \times 10^6$ transformants were screened. The screen was dependent upon interactions between the bait and prey to complement His auxotrophy. 15 $His^+/Trp^+/Leu^+$ colonies were obtained, and it was determined that ten of these colonies were also $LacZ^+$. pACT2-based plasmids from these ten colonies were isolated from yeast, transformed into *E. coli* BL21 (Novagen, Madison, Wis.) and the cDNA inserts were sequenced.

Example 7

Binding Assays

To examine the interactions between Hsc70 domains and in vitro-translated hCHIP, binding assays were performed with 3 µg of pGEXHsc70 deletion mutants (as prepared in Example 5) bound to glutathione-Sepharose 4B beads (Pharmacia, Piscataway, N.Y.) and 3 microliters (µl) of in vitro translation mixture containing $^{35}$S-labeled hCHIP as described in Example 5. Binding assays were performed in a binding buffer containing 50 millimolar (mM) NaCl and 1 milligram/milliliter (mg/ml) bovine serum albumin (BSA) (Sigma, St. Louis, Mo.) and agitated by rocking for 30 minutes at 4° C.

The glutathione-Sepharose 4B beads were pelleted in a centrifuge at 1500×g for 5 minutes and washed 4 times with a 0.1% NP-40 detergent (Sigma, St. Louis, Mo.) in phosphate buffered saline (PBS). The final pellet was resuspended in 2× Laemmli reducing buffer (Sigma, St. Louis, Mo.).

Two 12% SDS-polyacrylamide gels containing the products of the binding reactions above, were electrophoresed. The first gel was stained with Coomassie Blue and dried in cellophane. The second gel was dried onto chromatography paper (Fisher Biotech, Atlanta, Ga.) for autoradiography.

Additional in vitro binding assays were performed with 1 µg of purified Hsc70, Hsp70 or Hsp40 proteins or recombinant Hsc70, Hsp70 or Hsp40 proteins, and 15 µg of GST-fusion proteins (pGEXHsc70 or pGST-hCHIP) bound to glutathione-Sepharose 4B beads in the binding buffer. After binding, washing and electrophoresis as described above, a gel was transferred to nitrocellulose. Bound proteins were detected by immunoblotting. Bovine Hsc70, human Hsp70, and human Hsp40 were obtained from Stressgen Biotechnologies Corp., Victoria, British Columbia.

In a separate experiment to further study the interaction of CHIP with Hsp90, fragments of Hsp90, obtained from Stressgen, fused to GST (3 µg) were incubated with 200 ng of recombinant CHIP. The binding assay was performed as described in Ballinger et al., *Mol. Cell. Biol.*, 19: 4535–4545 (1999).

Example 8

Immunoblotting with Hsc70, Hsp70, and Hsp40

Western blots were stained with Fast Green (Sigma, St. Louis, Mo.) destained with Milli-Q purified water, and blocked with 5% dry milk/Tris buffered saline with Tween (TBST) buffer (20 millimolar (mM) Tris, 150 mM NaCl and 0.05% Tween 20 (Fisher Biotech, Houston, Tex.) for 1 hour at room temperature. The western blots were subsequently washed 3 times with TBST buffer, and incubated with the appropriate protein-specific primary antibody for 2 hours in TBST buffer. The mouse anti-human Hsp70/Hsc70 monoclonal antibodies (clone N27F3-4) and rabbit anti-human Hsp40 polyclonal antibodies were obtained from Stressgen Biotechnologies Corp., Victoria, British Columbia.

Following 3 washes in TBST buffer, the western blots were incubated for 1 hour with the appropriate horseradish peroxidase-conjugated anti-IgG secondary antibody in TBST buffer. All horseradish peroxidase-conjugated anti-IgG secondary antibodies (goat anti-mouse-HRP (product number A-19917) and goat anti-rabbit-HRP (product number A-9169) were from Sigma, St. Louis, Mo. Immunoreactive protein bands were detected by chemiluminescence.

Example 9

Antisera

Polyclonal antisera were generated in rabbits against the full-length recombinant hCHP, coupled to keyhole limpet hemagluttinin by standard procedures (performed by Alpha Diagnostics International, Inc., San Antonio, Tex.). Preimmune serum, i.e., serum removed from rabbits prior to antigen inoculation served as a control. The antiserum (hCHIP-3067) was shown to be specific for hCHIP in whole cell lysates as shown by Western blotting with competing protein.

Example 10

Immunoprecipitation

To test for in vivo binding partners, confluent 150-mm dishes of human skeletal muscle cells were lysed in 0.75 ml of radio-immune precipitation assay (RIPA) buffer (150 mM NaCl, 50 mM Tris, pH 7.5, 1 mM ethylene glycol-bis (β-aminoethyl ether-N,N, N', N'-tetraacetic acid (EGTA), 0.25% sodium deoxycholate, 1% NP-40 (Igepal (CA-630)), 1 mM sodium orthovanadate (Sigma) with complete protease inhibitor cocktail tablets (Boehringer Mannheim, Germany). After a 10 minute incubation period on ice, cells were scraped and centrifuged at 13,000×g for 10 minutes to remove cellular debris. The protein concentration of the whole cell lysate was determined by a Bio-Rad Protein Assay (Bio-Rad, Hercules, Calif.) and equal amounts of lysate were incubated with the appropriate antibodies (rabbit anti-hCHIP antiserum, rabbit preimmune serum, mouse anti-Hsp70/Hsc70-agarose conjugate, or a mouse IgG-agarose conjugate specific for nitric oxide synthase as a negative control) overnight (about 18 hours) at 4° C. The mouse anti-Hsp70/Hsc70-agarose conjugate antibody (W27) and the nitric oxide synthase-agarose conjugate were purchased from Santa Cruz Biotechnology, Santa Cruz, Calif. The anti-hCHIP and preimmune serum complexes were incubated with Protein A-Sepharose beads (Pharmacia, Uppsala, Sweden) for 2 hours at 4° C., and all complexes were pelleted and centrifuged at 3000×g for 3 minutes. The beads were then recovered, washed three times with RIPA buffer and once with PBS and resuspended in 2× Laemmli reducing buffer (2% SDS, 0.01 bromophenol blue, 20% glycerol, 114 mM Tris, pH 6.8, 10% α-mercaptoethanol).

Samples were separated on multiple 8% polyacrylamide gels by SDS-PAGE and transferred to nitrocellulose and immunoblotted as described above for the presence of Hsp70/Hsc70 and hCHIP. Mouse anti-human Hsp70/Hsc70 monoclonal antibodies (clone 3a3) used for immunoblotting were purchased from Affinity Bioreagents, Golden, Colo.

In a separate experiment to further study the interaction of CHIP with Hsp90, immunoprecipitations were performed with equal amounts of protein extracts from transfected COS-7 cells or human skeletal muscle cells. Lysates were incubated with antibodies (rabbit anti-human CHIP, mouse anti-Hsp90 3G3, or anti-nitric oxide synthase as a control) and blotted. For in vitro determination of Hsp90 complexes, rabbit reticulocyte lysates (50 µl) were incubated for 30 minutes at 30° C. in the absence or presence of increasing concentrations of recombinant CHIP (0.75, 3, or 30 µM). Hsp90 heterocomplexes were immunoprecipitated from lysates with 3G3 according to Owens-Grillo et al., *J. Biol. Chem.*, 270: 20479–20484 (1995). Antibodies used for blotting were: mouse anti-p60, mouse anti-Hsp90 AC88, mouse anti-human Hsc70 (StressGen); mouse anti-p23; and rabbit anti-human CHIP (Ballinger et al., *Mol. Cell. Biol.*, 19: 4535–4545 (1999)).

Example 11

ATPase Activity

ATPase assays were performed as described by Boice et al., *J. Biol. Chem.*, 272:24825–24831 (1997). Hsc70, Hsp, 70, Hsp90, and Hsp40 heat shock proteins were obtained from Stressgen Biotechnologies Corp., Victoria, British Columbia. Briefly, duplicate 25 μl reactions were assembled containing 1.25 microgram (μg) of heat shock protein (Hsc70, Hsp70, Hsp40, and/or Hsp90), 50 micromolar (μM) ATP (Sigma) and 1 μCi of [γ-$^{32}$P]ATP (3000 Ci/mmol, NEN/Dupont) (NEN/Dupont, Boston, Mass.) in the presence or absence of 1 μg recombinant hCHIP in Buffer C (20 mM Hepes, 10 mM $(NH_4)_2SO_4$, 25 mM KCl, 2 mM $Mg(OAc)_2$, 0.1 mM EDTA, and 0.1 mM dithiothrietol (DTT)).

Experiments were performed using 10 μg of hCHIP. There was no observable difference in the ATPase activity when compared to experiments performed using 1 μg of hCHIP (data not shown). At the beginning of the reaction time (time zero) and after 20 minutes, 8 microliters (μl) were removed from each reaction tube and added to 0.25 ml acidified, activated charcoal (Sigma) (50 mM HCl, 5 mM $H_3PO_4$ and 7% (w/v) activated charcoal), which is capable of binding any free nucleotides. The reaction tubes were centrifuged at 4,000 rpm for 20 minutes at 20° C. Duplicate 100 μl aliquots of the supernatant, containing $^{32}$P-labeled inorganic phosphate, were counted in a Beckman LS 3801 Scintillation Counter (Beckman Instruments, Fullerton, Calif.). The ATPase activity at each time point was calculated by subtracting the final counts per minute (cpms) from the initial background cpms.

Three additional independent experiments were performed as described above, and at least six measurements of ATPase activity were determined for each experimental condition. Data were normalized to the ATPase activity of Hsc70 alone.

Example 12

Nucleotide Binding Assay

Measurement of nucleotide species bound to Hsc70 was determined using the methods as described in Liberek et al., *Proc. Natl. Acad. Sci.*, (USA) 88:2874–2878 (1991) and Minami et al., *J. Biol. Chem.*, 271:19617–19624 (1996). Briefly, 1 μg of Hsc70 (Stressgen Biotechnologies Corp.) was incubated with 1 μg of recombinant hCHIP, (Hsp40 Stressgen Biotechnologies, Corp.), and/or BAG-1 (courtesy of Jörg Höhfeld (Max Planck Institute, Munich, Germany) in 25 μl of Buffer C containing 1 μCi of [α-$^{32}$P]ATP (3000 Ci/mmol) (NEN/Dupont). Employing these conditions, ATP was rapidly hydrolyzed (usually within about 1 minute) and ADP dissociation was measured. The results were consistent with previous reports (Minami et al., *J. Biol. Chem.*, 271: 19617–19624 (1996)). After 20 minutes, nucleotides bound to Hsc70 were separated from the free nucleotides by size-exclusion chromatography using a G-50 spin column (Amersham Pharmacia, Piscataway, N.J.). Aliquots of 2 μl each were subsequently analyzed by thin-layer chromatography on Selecto™ Cellulose PEI sheets (Fisher Biotech, Houston, Tex.) using 1 molar (M) formic acid/1 M LiCl (Fisher Biotech, Houston, Tex.). Unlabelled ATP and ADP were run simultaneously as standards and identified by UV light. The cellusose PEI Sheets were air-dried in a fume hood, covered in plastic wrap, and exposed to film in a light-tight cassette at −80° C. The binding of ATP and ADP were determined by densitometry (Molecular Dynamics, Sunnyvale, Calif.).

Example 13

Rhodanese Aggregation Assay

The aggregation of denatured rhodanese was measured by a modification of the protocol described by Minami et al., *J. Biol. Chem.*, 271:19617–19624 (1996)). Bovine liver rhodanese (30 μM, Sigma) was denatured in 6 M guanidine-HCl (Gibco BRL, Grand Island, N.Y.) 30 mM MOPS-KOH (Sigma) pH 7.2, and 2 mM DTT (Sigma) at-room temperature for 30 minutes. The denatured rhodanese was diluted to a final concentration of 1.2 μM in Buffer E (10 mM MOPS-KOH, pH 7.2, 50 mM KCl, 3 mM $MgCl_2$, 2 mM ATP and 2 mM DTT) in the presence or absence of 4 μM Hsp70, 2.5 μM Hsp40 and/or 2.5 μM recombinant hCHIP. The aggregation of rhodanese was measured by the absorbance of light at 340 nm.

The measured optical densities (OD) were normalized, to account for the addition of different proteins in the wells of a microtiter plate, to the zero reading for each individual well in the microtiter plate and the increase in absorbance plotted as a percent of the total increase for rhodanese alone. Each condition was repeated for a total of eight replicates. Absorbance plots were drawn using Microsoft Excel 98 to a polynomial of the $4^{th}$ order, i.e., a best fit line drawn to the equation $y=Ax^4+Bx^3+Cx^2+Dx+E$, wherein y=percent absorbance and x=time in minutes.

Example 14

Denatured Luciferase Binding Assay

Binding of denatured luciferase (Promega, Madison, Wis.) to Hsc70 was performed with modifications of the method described in Minami et al., *J. Biol. Chem.* 271: 19617–19624 (1996). Briefly, 0.57 μM Hsc70 was incubated in the presence or absence of 1.1 μM hCHIP and/or 1.1 μM Hsp40 in 50 μl of buffer C with 2 mM ATP for 5 minutes at 25° C. Luciferase, which was denatured as described below in reference to the luciferase folding assay, was added to a concentration of 0.16 μM, and the reaction was further incubated for 15 minutes at 25° C. Proteins interacting with Hsc70 were immunoprecipitated with the W27 conjugate antibody and washed as described above. The samples were separated by 8% SDS-PAGE and blotted with an anti-luciferase antibody (Rockland Immunochemicals, Gilbertsville, Pa. (product number 100-401-137)).

Example 15

Luciferase Folding Assay

Refolding of thermally denatured firefly luciferase (Promega, Madison, Wis.) was performed with modifications, i.e., deletions and concentration of proteins, of the procedure described by Lu et al., *J. Biol. Chem.*, 273:

5970–5978 (1998). 14.8 mg/ml of luciferase was diluted to 129 nanomolar (nM) in a buffered solution containing 25 mM Hepes, 50 mM KCl, 5 mM $MgCl_2$ at pH 7.4, and denatured by incubating at 42° C. for 20 minutes. During this incubation period, reaction tubes were prepared on ice containing 0.2 µM Hsp70 and/or 0.4 µM Hsp40 in the absence or presence of 0.4 µM recombinant hCHIP in 50 µl in the same buffered solution additionally containing 1 mm ATP.

Refolding assays were initiated by adding 2 µl of denatured luciferase to these reaction tubes at 30° C. At various time points from 0–120 minutes, i.e., 0, 15, 30, 45, 75, 120 minutes, 2 µl aliquots were removed from the reaction tubes and mixed with 60 µl of luciferase assay reagent (Promega) to measure luciferase activity on a Packard TopCount™ Microplate Scintillation Counter (Packard Instruments, Downers Grove, Ill.) Luciferase activity for each reaction was normalized to luciferase in refolding buffer alone. Experiments were repeated for a total of at least 12 measurements of refolding activity for each experimental condition. Refolding plots were prepared using Microsoft Excel to a polynomial of the $2^{nd}$ order.

Example 16

Ubiquitylation Assays

GR mRNA was transcribed with an Sp6-Ribomax™ kit according to protocol (Promega), followed by translation and $^{35}$S-labeling in reticulocyte lysate containing 25 mm MOPS pH 7.2, 100 mM KOAc, 5% glycerol, 0.5 mm DTT for 1 hour at 30° C. Unlabeled methionine, puromycin, and cycloheximide (2 mM) were added and samples were centrifuged for 10 minutes at 30,000×g. Phosphocreatine (10 mM), creatine phosphokinase (50 µg/ml), ATP (0.5 mM) and $MgCl_2$ (2 mM) were added to the supernatants. Samples were incubated for an additional 2 hours in the presence of recombinant CHIP and/or Hsc70 (1.8 µM) with or without ubiquitin (250 µg/ml) and ubiquitin-aldehyde (10 µg/ml), an inhibitor of ubiquitin isopeptidases.

Example 17

Steroid Binding Assays

Reticulocyte lysate (50 µl) was incubated with or without the indicated concentrations of CHIP or heat-inactivated CHIP (100° C. for 5 minutes) for 30 minutes at 30° C. GR was $^{35}$S-labeled by coupled transcription/translation in this lysate according to protocol (Promega). Following translation, 5 µl of each sample was removed for electrophoresis. The remaining samples were incubated with 50 nM $^3$H-triamcinolone acetonide for 2 hours at 4° C., followed by gel filtration, as described by Segnitz et al., *J. Biol. Chem.*, 272: 18694–18701 (1997). Fractions (150 µl) were collected and binding of steroid determined by scintillation counting. To assess the effects of CHIP on GR bound to Hsp90, reticulocyte lysate containing $^{35}$S-labeled GR was incubated in the presence or absence of CHIP or heat-inactivated CHIP, followed by immunoprecipitation with 3G3. Samples were electrophoresed (to assess binding of GR to Hsp90) or incubated with 50 nM $^3$H-triamcinolone acetonide for 3 hours at 4° C. (to measure steroid binding activity).

Example 18

Transient Transfections

COS-7 cells were transiently transfected using FuGene™ (Boehringer Mannheim) according to protocol. For luciferase reporter assays, pRShGRC (expressing human GR), pcDNA3-CHIP (expressing untagged human CHIP), or pcDNA3 alone were transfected with the dexamethasone-responsive reporter pHH-Luc and a β-galactosidase expression vector to normalize for transfection efficiency. Cells were incubated in the presence or absence of dexamethasone (1 µM) for 24 hours. Reporter gene activities were determined as described in Wu et al., *J. Biol. Chem.*, 274: 3207–3214 (1999). For steroid binding, COS-7 cells transfected with the appropriate expression vectors were incubated with 50 nM $^3$H-triamcinolone acetonide in the presence or absence of 100-fold molar excess unlabeled triamcinolone as described in Whitesell et al., *Mol. Endo.*, 10: 705–712 (1996). Incorporated steroid was extracted with ethanol and determined by scintillation counting. For analysis of GR expression, pcDNA3-CHIP, pcDNA3-CHIPΔTPR (amino acid residues 32–145 deleted), or pcDNA3-CHIPΔE4 (amino acid residues 196–303 deleted) were transfected with pRShGR-C. In some experiments, transfected cells were treated wtih MG-132 (20 µM) or vehicle for 2.5 hours before harvesting. Western blots were performed using an anti-human GR polyclonal antibody (Affinity Bioreagents).

Results

Cloning of a Novel Tetratricopeptide (TPR)-Containing Protein from a Human Heart cDNA Library.

A human heart cDNA library was screened at low stringency conditions (as shown in Example 1) with the cDNA fragment (nucleotides 721–1150) from human CyP-40 corresponding to the three carboxy-terminal TPR domains Kieffer et al., *J. Biol. Chem.*, 268:12303–12310 (1993). With this technique, 12 positive colonies were identified, 8 colonies were shown to contain human CyP-40 sequences, and 4 colonies were identified as encoding a novel partial cDNA sequence. The full-length cDNA (SEQ ID NO: 1) of the identified nucleotide sequence was shown to contain 1286 nucleotides, and contain a single open reading frame (ORF) encoding a deduced amino acid sequence of 303 residues (SEQ ID NO: 2, FIG. 3). The predicted molecular weight of the translated protein is 34.8 kD based on the deduced amino acid sequence.

In vitro transcription/translation using the full-length cDNA as a template, produced a specific protein product of the expected size, thus validating the predicted ORF. The primary amino acid sequence was shown to contain three 34-amino acid TPR domains at its amino terminus, a central domain rich in charged residues, and two potential nuclear localization signals (amino acids 143–146 and amino acids 221–225 of SEQ ID NO: 2). The $NH_2$-terminus shares similarity with other TPR-containing proteins (FIG. 2), and most particularly, those TPR containing proteins that interact with members of the heat shock protein family, i.e., HIP, protein phosphatase 5, and cyclophilin-40. The carboxy-terminal region contains no defining structural motifs, although amino acids 218–293 share approximately 50% similarity as determined by GeneWorks™ 2.5.1, with three proteasome-linked proteins, UFD2, NOSA, and the p40 subunit of the 26S proteasome (Dubiel et al., *FEBS Letters*, 363:97–100 (1995), Johnson et al., *J. Biol. Chem.*, 270: 17442–17456 (1995), Pukatzki et al., *J. Biol. Chem.*, 273: 24131–24138 (1998), respectively.

The mouse CHIP (SEQ ID NO: 9) and *Drosophila* CHIP (SEQ ID NO: 10) homologues of hCHIP were also cloned as described above, to determine the degree of conservation that extended to other species and to further define potential functional domains. When compared by GeneWorks™ 2.5.1 with hCHIP (SEQ ID NO: 1) there was about 97% sequence identity and a about 98% sequence similarity with the mouse sequence, and a 53% sequence identity and 60% sequence similarity with the *Drosophila* sequence (FIG. 2). Surprisingly, the most highly conserved region was determined to be the 94 amino acid residues of the carboxy-terminus (amino acids 209–303), which showed an 87% sequence similarity and a 75% sequence identity among these species. Whereas the amino-terminal residues (amino acids 1–127) place CHIP in the general category of a TPR-containing protein, the unique, highly conserved carboxyl terminus suggest a cellular function different from that of other members of this class involved in protein degradation.

Tissue Distribution of CHIP

In a first step in the characterization of hCHIP, the expression of hCHIP mRNA in human tissues and cell lines by Northern blot analysis was examined. Hybridization under the low-stringency conditions shown in Example 3 with the full-length hCHIP cDNA (amino acids 1–303) resulted in a single band of approximately 1.3 kilobases (kb). hCHIP was most highly expressed in human striated muscle (skeletal muscle and heart), with somewhat lesser expression in pancreas and brain, and relatively little message present in lung, liver, placenta, and kidney.

In tissue culture, hCHIP mRNA was easily detected in most human cell lines and primary culture cells tested, i.e., HASMC, HeLa, HepG2, HuSkMC, HUVEC, RD, and SaOS-2. The exceptions were cells of hematopoietic origin (IM-9 lymphoblastoid and U937 monocytic cells) and HCN-1A undifferentiated neuronal cells.

Intracellular Localization of CHIP

Expressed fusions of full-length hCHIP with green fluorescent protein (GFP) by transient transfection in COS-7 monkey kidney-derived cells obtained from the American Type Culture Collection, Bethesda, TVID, (Accession No. CRL-1651) to localize expression of hCHIP within the cell. For controls, expressed GFP alone and GFP fused to a nuclear localizing fragment of GKLF (Shields et al., *J. Bio. Chem.* 29:18504–18507 (1997)) were employed using the same method.

It was observed that the GKLF fragment localized GFP to the nucleus and that GFP alone exhibited diffuse expression throughout the cell. In contrast, hCHIP localized GFP strictly to the cytoplasm in a diffuse pattern. Thus, in spite of having two potential nuclear localization signals, the hCHP-GFP fusion protein appears to localize to the cytoplasm. However, it is very possible that native hCHIP may be transported out of the cytoplasm in response to an appropriate stimulus, such as a response to phosphorylation events.

hCHIP interacts with Heat Shock Proteins Hsp70 and Hsc70 in the Yeast Two-Hybrid System The yeast two-hybrid system assay (Gyuris et al., *Cell*, 75:791–803 (1993)) was employed to identify proteins that interact with hCHIP. A bait vector as described in Example 6, was constructed to express full-length hCHIP fused to the GAL4-binding domain. A human heart cDNA expression library was screened with the prepared construct and ten positive (His$^+$, LacZ$^+$) clones from 2.5×10$^6$ transformants were identified. Of the ten positive clones, five clones encoded fragments of Hsc70 and three clones encoded fragments of Hsp70 in frame with the GAL4 activation domain. The five clones encoding fragments of Hsc70 and the three clones encoding fragments of Hsp70 identified contained the carboxyl terminus of either Hsp70 or Hsc70; the shortest clone encoded 225 amino acids of the carboxy-terminal domain of Hsp70. hCHIP did not interact with the negative control proteins p53, the SV40 large T antigen (Clontech, Palo Alto, Calif.) or GAL4 alone in this assay, nor did Hsc70 or Hsp70 interact with the negative control lamin C or GAL4 alone, demonstrating the specificity of these in vivo interactions.

hCHIP Interacts with Hsc70 and Hsp70 [Hep 70] In Vitro

In vitro binding assays using a GST-hCHIP fusion protein were performed to confirm the interactions between hCHIP and heat shock protein Hsc70 detected in the yeast two-hybrid screen. This assay was also performed to exclude the possibility that these interactions were indirect, i.e., requiring additional auxiliary proteins. It was observed that heat shock proteins Hsc70 and Hsp70 both bound to the GST-hCHIP fusion protein but not to GST alone. In contrast, there was no observable interaction between Hsp40 and hCHIP in this assay, although co-chaperone Hsp40 did interact specifically with the carboxy-terminal amino acid residues 540–650 of Hsc70 (a test of the binding activity of this Hsp40 preparation), as has been shown previously (Demand et al., *Mol. Cell. Biol.*, 18:2023–2028 (1998)). It should be noted that these binding assays were performed in the absence of ATP However, it was observed that neither the presence of ATP or ADP influenced the affinity of hCHIP for Hsc70 in these assays (data not shown). Thus, these experiments demonstrate that hCHIP interacts specifically with heat shock Hsc70 and Hsp70 in in vitro binding assays in an ATP-independent fashion.

CHIP Interacts with Hsc70 In Vivo

Co-immunoprecipitation experiments were performed to demonstrate that the interactions between hCHIP and heat shock proteins Hsc70 and Hsp70, identified in the in vitro binding assays and in the yeast two-hybrid system, also occur under physiologic conditions in mammalian cells. Immunoprecipitates of human skeletal muscle cellular lysates derived from cells described in Example 2 using a polyclonal anti-hCHIP antibody also described in Example 2, contained in addition to hCHIP, a single, specific 73-kD band which was identified by an anti-human Hsp70/Hsc70 monoclonal antibody (Santa Cruz Biotech, Santa Cruz, Calif.). This band is identical in size to the band identified by this antibody in whole cell lysates and co-migrates with purified Hsc70. Similarly, immunoprecipitates of skeletal muscle. lysates using an anti-Hsp70/Hsc70-agarose conjugate (Santa Cruz Biotech, Santa Cruz, Calif.) contained a 35-kD band recognized by the anti-hCHIP antisera and identical in size to hCHIP. In contrast, the specific 35-kD band was not detected in immunoprecipitates using a monoclonal mouse IgG (Santa Cruz Biotech, Santa Cruz, Calif.) recognizing nitric oxide synthase. HCHIP was also not detected in immunoprecipitates using rabbit preimmune serum as described in Example 10, or other nonspecific antibodies. Given the concordance of these data with those from the yeast two-hybrid system, it is most likely that these experiments indicate the formation of a stable complex between hCHIP and heat shock proteins Hsc70 and Hsp70 under physiologic conditions of the cellularlysates in mammalian cells, although the possibility that complexes may have formed after lysis cannot be excluded.

CHIP Interacts with the Carboxy-Terminal Domain of Hsc70 In Vitro

To characterize the Hsc70 domains necessary for interaction with hCHIP, binding was tested between $^{35}$S-labeled, in vitro translated hCHIP, and a series of GST-Hsc70 aminoand carboxy-terminal deletion mutants (Ungewickell et al., *J. Biol. Chem.*, 272:19594–19600 (1997)). These mutants were designed to delineate the binding activity of the nucleotide-binding domain of Hsc70 (amino acids 1–138 of Hsc70, GENBANK accession number no. Y00371), the substrate-binding domain of Hsc70 (amino acids 383–543, GENBANK accession number no. Y00371), and the carboxy-terminal domain of Hsc70 (amino acids 540–650, GENBANK accession number no. Y00371).

Affinity purification (see, Example 5) of the GST fusions by glutathione-Sepharose chromatography was efficient and nearly equivalent after the binding reactions, and demonstrated appropriate folding of the fusion proteins. hCHIP was observed to be bound to the carboxy-terminal Hsc70 amino acid fragments 373–650 and 540–650, but not to fragments lacking amino acids 540–650, nor to GST itself. Consistent with the observations in the yeast two-hybrid system, the carboxy-terminal domain seems to be both necessary and sufficient for hCHIP interacting with Hsc70, whereas the ATPase and substrate-binding domains of Hsc70 are expendable. This specific interaction provides the basis for defining this protein as CHIP, carboxyl terminus of Hsc70-interacting protein.

Figure 4:
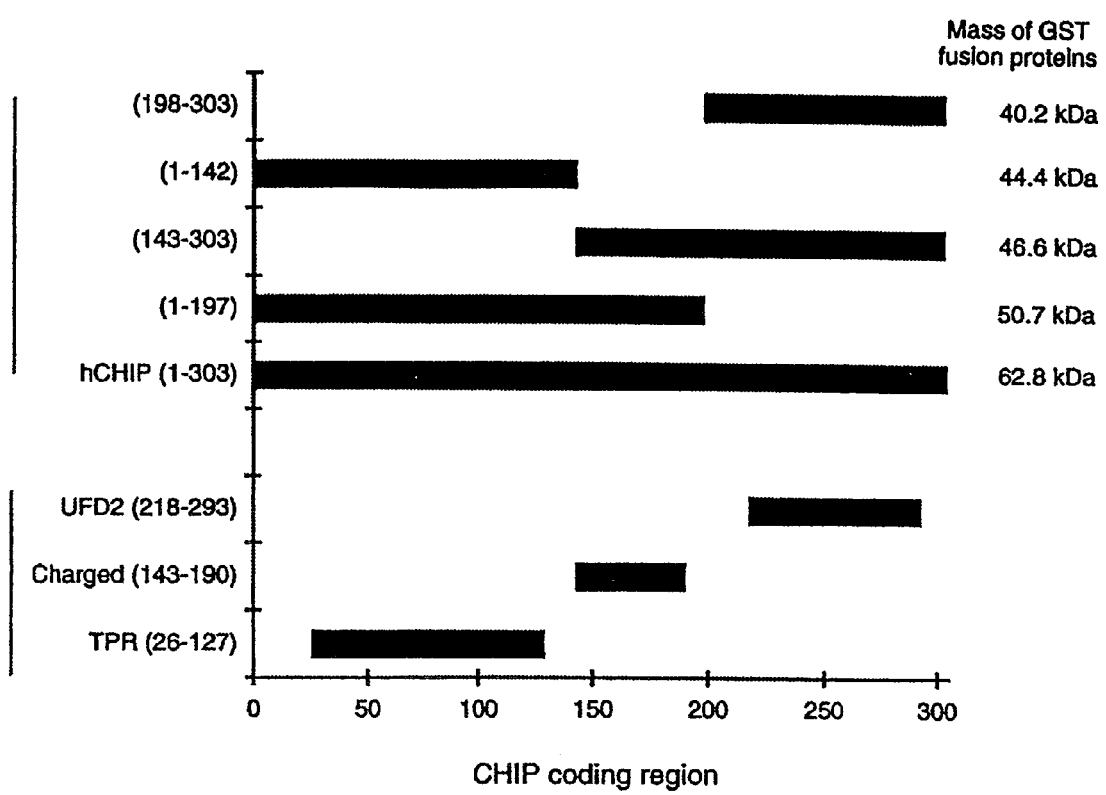
FIG. 4. The TPR domain of hCHIP and relative binding to Hsp70 and Hsc70: Diagram showing the location of the three TPR domains (amino acid residues 26–127), charged residues (amino acid residues 143–190), and proteasome-linked protein UFD2-like domains (amino acid residues 218–293) within the hCHIP coding region (SEQ ID NO: 2). The diagram also shows the constructs of five GST-hCHIP fusion proteins that contain one or more of these domains. GST construct 1 (amino acid residues 198–303) having an apparent molecular weight of about 40.2 kD, GST construct 2 (amino acid residues 1–142) having an apparent molecular weight of about 44.4 kD, GST construct 3 (amino acid residues 143–303) having an apparent molecular weight of about 46.6 kD, GST construct 4 (amino acid residues 1–197) having an apparent molecular weight of about 50.7 kD, and GST construct 5 (amino acid residues 1–303) having an apparent molecular weight of about 62.8 kD.

The TPR Domain of hCHIP is Necessary but not Sufficient for Binding with Heat Shock Proteins A series of hCHIP fragments fused to GST were prepared to determine the domains of hCHIP that are required for protein—protein interactions with heat shock proteins. The constructs generated, in relationship to hCHIP domains, are shown in FIG. 4. Binding of these GST fusions with Hsp70 and Hsc70 was tested by in vitro binding assays. Whereas full-length hCHIP interacted with Hsc70 in these experiments, fusions containing amino acids 143–303 alone did not, demonstrating the importance of the amino terminus of hCHIP in these interactions. Amino acids 1–142, which contain the three TPR domains, were not sufficient for this interaction either. It was determined that amino acid residues 143–197 of hCHIP were also required for binding with Hsc70 to occur. As expected, similar binding requirements were found for interactions with Hsp70. Although both HIP and HOP interact with Hsc70 by means of TPR domains (Demand et al., *Mol. Cell. Biol.*, 18:2023–2028 (1998)), these experiments establish that both the TPR domain and an adjacent charged domain are required for interactions between hCHIP and heat shock proteins.

Effects of Recombinant hCHIP on ATPase and Chaperone Activities of Heat Shock Proteins Hsp70 and Hsc70 contain an amino-terminal ATP-binding domain (amino acids 1–373). The intrinsic ATPase activity of these proteins is facilitated by co-factors such as HEP and Hsp40 (Hohfeld et al., *Cell*, 83:589–598 (1995), Liberek et al., *Proc. Natl. Acad. Sci.*, (USA) 88:2874–2878 (1991)). This cycle is necessary for peptide binding and folding, the so-called chaperone activity of heat shock proteins as reviewed in Netzer et al., *Trends Biochem. Sci.*, 23:68–73 (1998). Given the interactions of hCHIP with heat shock proteins Hsc70 and Hsp70, it was examined whether hCHIP had an effect on their ATPase and chaperone activities, in the presence or absence of Hsp40. Recombinant hCHIP expressed in *E. coli* BL21 (Novagen, Madison, Wis.) was used in these studies, given the precedence for retention of ATPase and folding activity when other proteins have been expressed in this system (Minami et al., *J. Biol. Chem.*, 271:19617–19624 (1996), Naylor et al., *J. Biol. Chem.*, 273:21169–21177 (1998)).

Figure 5:
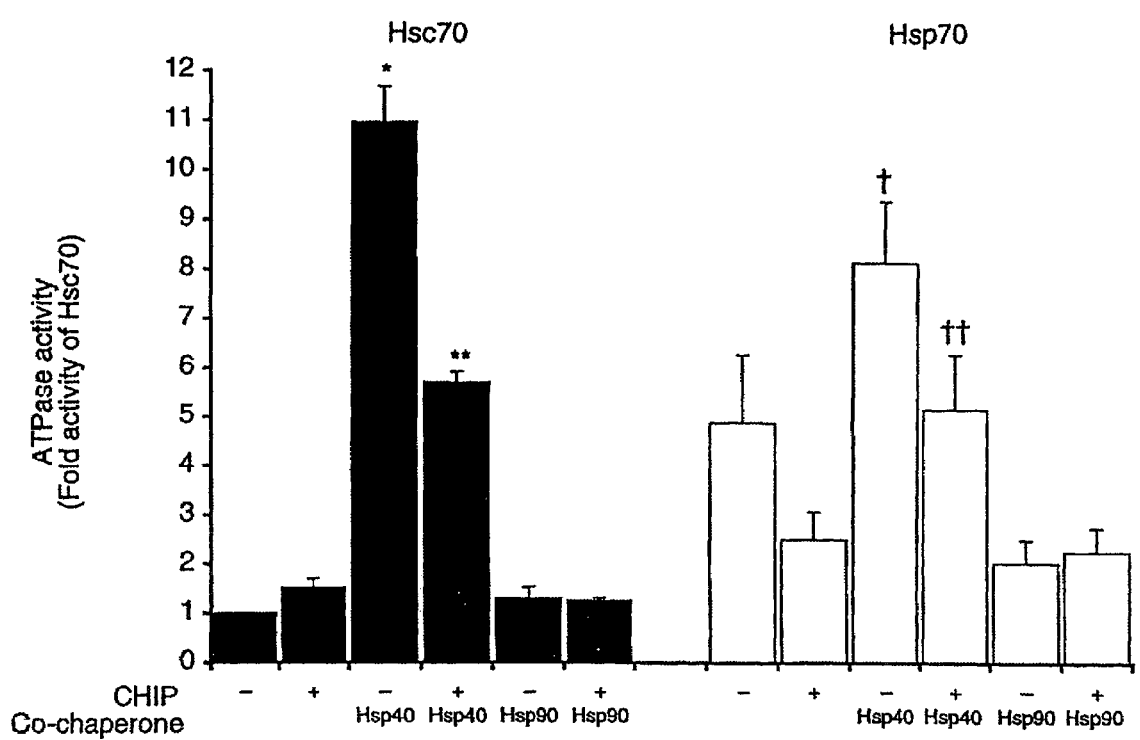
FIG. 5. Effects of hCHIP on ATPase activities and nucleotide binding of heat shock proteins: The ATPase activities of Hsc70 (black bars) and Hsp70 (white bars) were measured over 20 minutes in the presence or absence of hCHIP, Hsp40 and/or Hsp90 as indicated. Data were normalized to the ATPase activity of Hsc70 alone. * (or †) indicates a significant difference (p<0.05) between the ATPase activity of Hsc70 alone (or Hsp70 alone) and Hsc70+Hsp40 (or Hsp70+Hsp40). ** (or ††) indicates a significant difference (p<0.05) between the ATPase activity of Hsc70+Hsp40 (or Hsp70+Hsp40) and Hsc70+Hsp40+CHIP (or Hsp70+Hsp40+CHIP). Each condition was repeated for a total of six replicates.

It was confirmed that recombinant hCHIP retained binding activity to Hsc70, to ensure that it was correctly folded and processed in bacteria. The rate of ATPase activity of Hsc70 was significantly increased (11-fold) by the addition of Hsp40 ($p<0.05$, FIG. 5, black bars), consistent with previous observations (Frydman et al., *Nature*, 370: 11–117 (1994)). hCHIP had little effect on basal Hsc70 ATPase activity, but significantly blunted the augmentation of Hsc70 activity by Hsp40 ($p<0.05$). Similar experiments were performed using Hsp70 (FIG. 5, white bars). The basal ATPase activity of Hsp70 was higher and the enhanced induction by Hsp40 was lower in comparison with Hsc70 in this set of experiments, which likely reflects some Hsp40-like activity contaminating the preparation of Hsp70. In spite of this observation, hCHIP blocked the ATPase activity of Hsp70/Hsp40 to a degree similar to that observed for Hsc70/Hsp40 ($p<0.05$).

Without being bound by any particular theory, the effects of hCHIP on ATPase activity could be due to interference with ATP binding, inhibition of ATP hydrolysis, or modulation of nucleotide release. Thin-layer chromatography was also performed to determine whether hCHIP affected the nucleotide-bound state of Hsc70 under steady-state conditions (Example 12). Under these conditions, ATP is limiting and is rapidly and nearly completely hydrolyzed to ADP. Consistent with previous reports (Höhfeld et al., *EMBO J.* 16:6209–6216 (1997)), BAG-1 potently stimulated release of bound ADP from Hsc70. By comparison, hCHIP did not elicit nucleotide release from Hsc70, whether or not Hsp40 was present, suggesting that its regulation of Hsc70 function is not dependent on modulation of nucleotide release.

Figure 6:
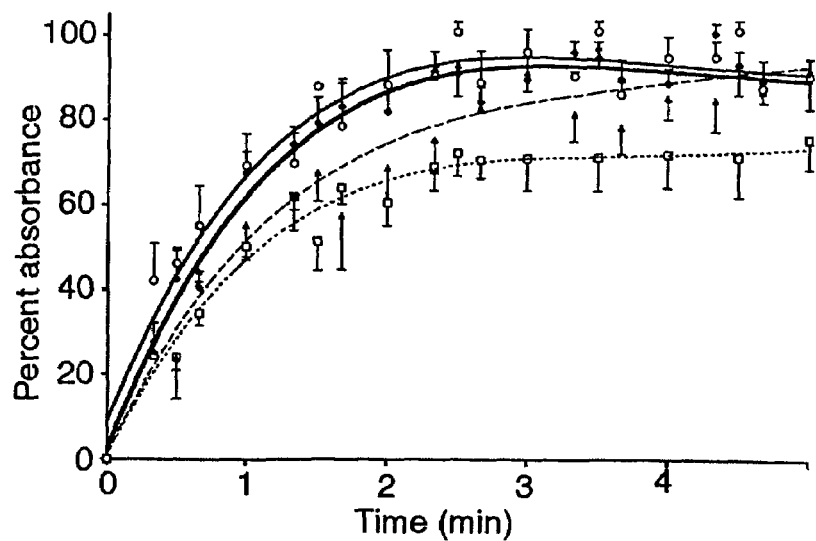
FIG. 6. Effects of CHIP on chaperone functions of heat shock proteins.

The aggregation of denatured rhodanese by spectrophotometry was measured to assess the effect of hCHIP on Hsp70 substrate binding. Under the conditions employed, rhodanese alone maximally aggregated after 2.5 minutes (FIG. 6). hCHIP alone had no affect on rhodanese aggregation. Addition of Hsp70 and Hsp40 reduced rhodanese aggregation by 30%, indicative of binding to denatured rhodanese. The addition of hCHIP markedly reduced the ability of Hsp70/Hsp40 to inhibit rhodanese aggregation, and aggregation of denatured rhodanese in the presence of hCHIP/Hsp70/Hsp40 at 5 minutes was no different than that of rhodanese alone. To confirm these results, the ability of Hsc70 to interact with denatured luciferase was measured by coimmunoprecipitation with an anti-Hsc70 antibody. Denatured luciferase was present in immunoprecipitates when incubated with Hsc70 or Hsc70/Hsp40. However, recovery of luciferase was significantly retarded when hCHIP was incubated with either Hsc70 or Hsc70/Hsp40. Taken together, these data indicate that hCHIP blocks the ability of the Hsp70/Hsp40 complex to bind denatured luciferase or prevent aggregation of denatured rhodanese, presumably by interfering with binding of substrates to Hsc70/Hsp70.

The well-characterized luciferase refolding assay was employed as a measure of Hsp70 chaperone function hCHIP alone had little effect on the rate of luciferase refolding, when corrected for that which occurred in buffer alone (FIG. 7). Hsp70 markedly enhanced the rate of refolding, an effect which was potentiated by Hsp40. In contrast, hCHIP decreased the folding activity of Hsp70 or Hsp70/Hsp40 by 65% and 64%, respectively. The extent to which hCHIP inhibited refolding was similar regardless of whether hCHIP polypeptide was present in molar excess or molar equivalency with other proteins in the assay (not shown), indicating that specific interactions with Hsp70, rater than nonspecific competition for substrates, is the more likely explanation for these results.

These experiments indicate that, at least in part, hCHIP functions as a negative regulator of Hsp70- and Hsc70-mediated chaperone functions. This occurs, most likely, by inhibiting the forward reaction of the substrate-binding cycle, resulting in lower substrate affinity of Hsc70/Hsp70.

Figure 12A:
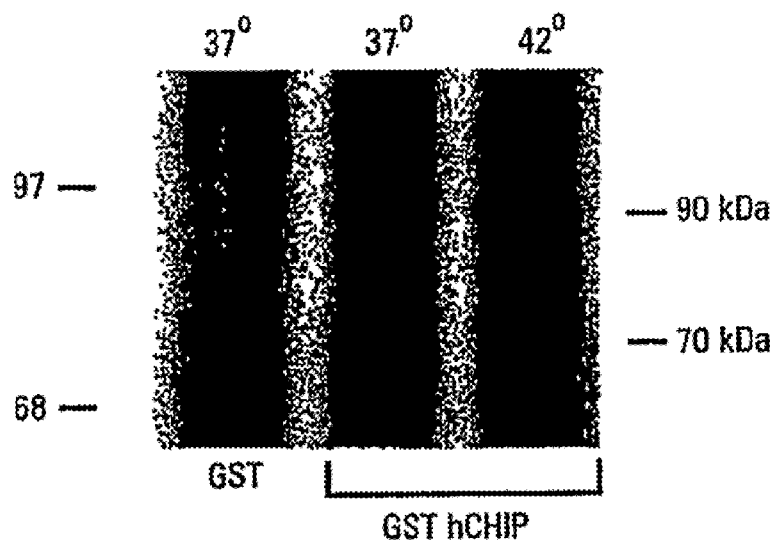
Figure 12B:
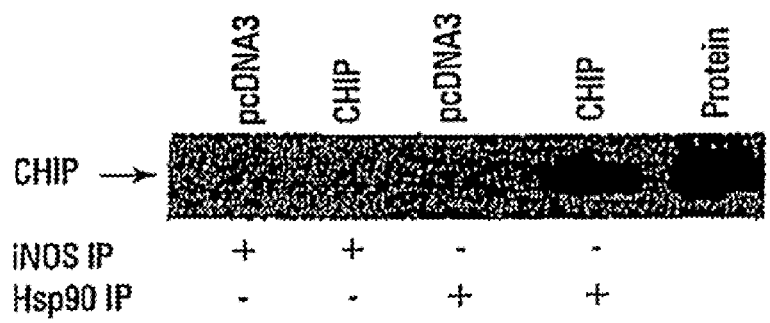
Figure 12C:
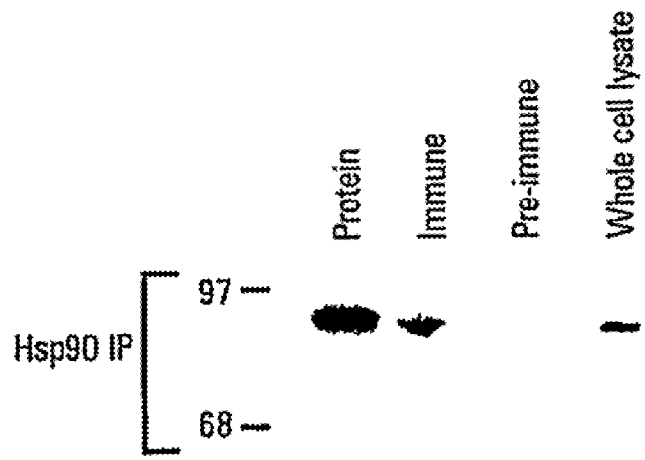

Regulation of Hsp90-Mediated Protein Triage Decisions by the Antic haperone CHIP GST-CHIP fusion proteins were used to coprecipitate proteins from lysates of human skeletal muscle cells (which express high levels of CHIP constitutively) to identify additional interacting proteins. In addition to a 70 kD protein, a prominent 90 kD, heat shock-inducible protein was observed that bound specifically to GST-CHIP (FIG. 12A). To determine whether this protein might be Hsp90, CHIP was overexpressed in COS-7 cells and CHIP was specifically immunoprecipitated using an antibody to Hsp90 (FIG. 12B). To verify the existence of endogenous CHIP/Hsp90 heterocomplexes, skeletal muscle cell lysates were immunoprecipitated with anti-CHIP antisera, and found Hsp90 in CHIP immunoprecipitates (FIG. 12C). These data indicate that, in addition to regulating the Hsp70 reaction cycle, CHIP is an in vivo interaction partner with Hsp90.

Hsc70 interacts with Hsp90 in vitro and in vivo to mediate the folding of a limited number of proteins. To establish whether CHIP's interactions with Hsp90 are direct and independent of binding to Hsc70, in vitro binding assays were performed using GST fusion proteins. Hsp90 was pulled down with GST-CHIP, but not GST alone, demonstrating a direct interaction between Hsp90 and CHIP (FIG. 13A). To identify the binding determinants required for CHIP's interaction with Hsp90, binding assays utilizing fusions of GST with specific domain(s) of CHIP were performed. Similar to CHIP's interaction with Hsc70, the binding interaction between CHIP and Hsp90 requires 3 TPR motifs and an adjacent charged domain of CHIP (FIG. 13B). As the determinants for binding CHIP with Hsc70 and Hsp90 are similar, it is unlikely that CHIP can bind both chaperones simultaneously; CHIP most likely regulates these chaperones independently of one another. Because Hsp90 contains multiple, structurally diverse functional domains, and to exclude the possibility that CHIP binds Hsp90 nonspecifically as a substrate, the domain(s) of Hsp90 bound by CHIP were determined using GST fusion proteins of Hsp90 fragments. A fragment that encompasses the carboxyl terminus of Hsp90 (residues 629–732) specifically bound CHIP (FIG. 13C). Because the carboxyl terminus of Hsp90 contains an acceptor site through which the binding of various TPR-containing proteins modulates Hsp90 heterocomplex function, it was ascertained whether CHIP bound to Hsp90 via the TPR acceptor site. Equimolar concentrations of Hop (which contains 6 TPR domains) interfered with CHIP's ability to bind Hsp90 (FIG. 13D), whereas 10-fold excess Hsp40 did not affect binding of CHIP to Hsp90 (not shown).

The binding of accessory proteins to Hsp90 via the TPR acceptor site is an important means by which Hsp90 function is regulated, therefore, CHIP's interactions with this site led to testing its effects on the Hsp90 heterocomplex. Reticulocyte lysate has sufficient quantities of Hsp90 heterocomplex components to assist in maturation of its substrates. Recombinant CHIP readily incorporated into Hsp90 heterocomplexes in these lysates (FIG. 14A). The presence of CHIP did not affect the ability to immunoprecipitate Hsp90, but did decrease the amount of Hop associated with the complex by 50% and led to total dissociation of p23. These data demonstrate that CHIP functions to remodel Hsp90 heterocomplexes in a manner that should be unfavorable to substrate activation and that is dissimilar to remodeling elicited by other cochaperones that contain TPR domains.

GR, transcribed and translated in vitro, was used as a model substrate to test the effects of CHIP on Hsp90 chaperone function. In the presence of CHIP, there was a dose-dependent decrease in the steroid-binding activity of GR to 10% of control values (FIG. 14B), an effect that was abolished by heat-inactivating CHIP. This effect could not be accounted for by a decrease in steady-state levels of full-length GR, which is synthesized efficiently (92% of control) in the presence of CHIP (FIG. 14C, upper panel). The decrease in GR activity may result in CHIP's effect on the Hsp90 heterocomplex. To address this, translated GR was incubated in the presence or absence of CHIP, and Hsp90 was immunoprecipitated to determine the amount of GR associated with the heterocomplex. 50% less GR co-precipitated with Hsp90 in the presence of CHIP (FIG. 14D, lower panel). To access the function of Hsp90-associated GR, whether or not Hsp90-associated GR bound steroid was examined. In contrast to GR from lysates incubated without CHIP or with heat-inactivated CHIP, the ligand-binding ability of GR associated with Hsp90 was decreased by 85% when CHIP was present in the lysates (FIG. 14D), indicating that Hsp90-bound GR in the presence of CHIP is not its in steroid-binding conformation. The decrease in GR associated with Hsp90 in the presence of CHIP was not due to decreased steady-state levels of GR, and therefore presumably results from dissociation of GR from Hsp90. Although the fate of GR that is dissociated from Hsp90 in the presence of CHIP is unknown. It is hypothesized it might be released to components of the ubiquitin-proteasome system. A shift in the Hsp90 chaperone system from refolding to degradation is well documented, although the cellular mechanisms regulating this transition are not known. To determine whether the effect of CHIP on the Hsp90 heterocomplex led to ubiquitylation of GR, GR was incubated with CHIP and ubiquitin after its translation. In reticulocyte lysate (which contains hemin to inhibit the proteasome), high molecular weight ubiquitylated forms of GR were markedly increased in the presence of CHIP and ubiquitin plus ubiquitin-aldehyde (FIG. 14E).

Figure 15A:
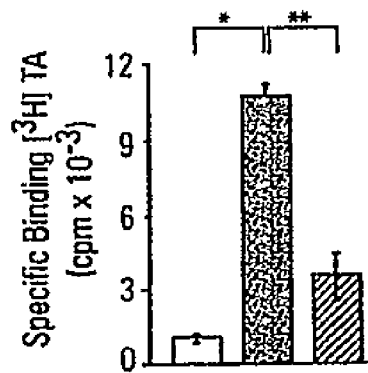
Figure 15B:
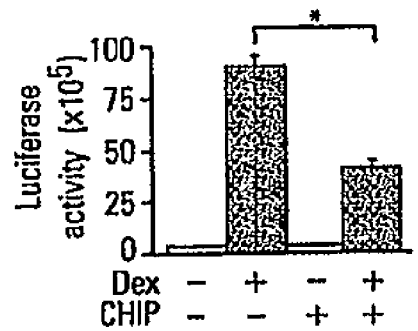
Figure 15C:
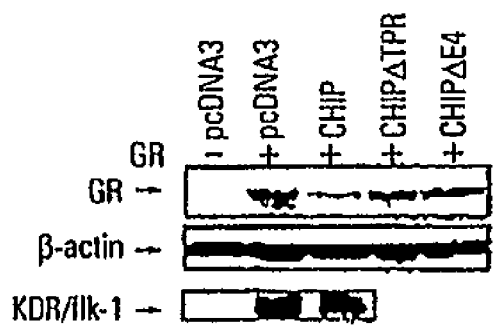

To determine whether the effects of CHIP on GR destiny in the cell-free system also occurred in vivo, GR, with or without CHIP was expressed, in COS-7 cells. Steroid-binding activity of GR-containing lysates was decreased by 75% in cells co-expressing CHIP (FIG. 15A). Similarly, CHIP expression decreased the ability of GR to transactivate a dexamethasone-responsive promoter in COS-7 cells by 60% (FIG. 15B). Based on the observation that CHIP elicited ubiquitylation of GR in vitro, the effect of CHIP on GR expression in COS-7 cells was examined. CHIP had no effect on GR mRNA expression (not shown). However, steady-state GR protein levels were dramatically reduced in cells overexpressing CHIP (FIG. 15C). The effects of CHIP on this Hsp90 substrate were specific, as endogenous β-actin expression and ectopically expressed KDR/flk-1 (which is not known to be an Hsp90 substrate) were unaffected by CHIP. To test the specificity of this effect, constructs were created in which the TPR (ΔTPR) and U-box (ΔE4) domains of CHIP were deleted. Although expression of these proteins was similar to that of wild-type CHIP, deletion of either of these domains abolished the effects of CHIP on GR.

Figure 15D:
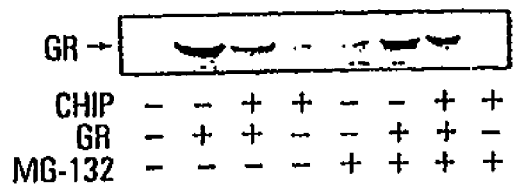

The consequences of the ΔTPR deletion are not surprising, as the TPR domains of CHIP are required for interaction with Hsp90 (FIG. 14B). The lack of activity of CHIPΔE4, which still binds Hsp90, indicates that the effects of CHIP are not merely due to interactions with Hsp90. The U-box was first identified in UFD2, a yeast protein required for multiubiquitylation. The requirement of this domain for CHIP's effects on GR expression and function suggests that CHIP enhanced ubiquitylation of GR and its transfer to the proteasome. This is consistent with our observation that CHIP elicits ubiquitylation of GR in vitro (FIG. 14E). To confirm that the effect of CHIP on GR protein levels require the proteasome pathway, cells were treated with selective inhibitor of the proteasome, MG-132[24]. GR expression was completely restored when cells co-transfected with CHIP were treated with MG-132 (FIG. 15D). It can be concluded that CHIP's interaction with Hsp90-bound GR directs it toward proteasome pathways. Consistent with this scenario, ternary complexes of GR, Hsp90, and CHIP in transfected COS-7 cells (not shown) have been observed.

The discovery that CHIP impairs maturation and elicits ubiquitylation of the model Hsp90 substrate GR in vitro, and decreases steady-state GR levels in a proteasome-dependent manner in vivo, indicates that CHIP is a molecular link between the chaperone and proteasome machinery. Consistent with this model, CHIP associates with multiubiquitylated proteins and the S5a component of the proteasome in vivo. It can be suggested that CHIP poses an antichaperone activity. Although it is known that Hsp90 can partition its substrates toward the degradation pathway, the molecular mechanism by which the cell commits to the degradation of chaperone substrates have been elusive. The interaction between CHIP and Hsp90 (and most probably Hsc70 as well may regulate a nodal step in the triage of substrates for cytoplasmic chaperones, directing the status of substrate folding or degradation as a means of regulating protein quality control in the cell. A kinetic model for maintaining quality control, in which the decision to degrade a substrate is determined by unproductive cycling on and off of the chaperone, has been proposed previously and is well-supported. This model relies on the affinity of a substrate for a chaperone or protease to dictate a protein's fate, and infers a competition between chaperones and components of the degradation machinery. A complementary mechanism of cooperation is proposed here, whereby the chaperone system, through expression and function of antichaperones such as CHIP, interacts functionally with the proteasome to maintain highly efficient quality control of proteins that are substrates for the cytosolic chaperones.

The complete disclosures of all patents, patent documents, publications, ATCC deposits, electronically available material (e.g., GENBANK amino acid and nucleotide sequence submissions), etc., cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

SEQUENCE LISTING

<160> NUMBER OF SEQ ID NOS: 20

<210> SEQ ID NO 1
<211> LENGTH: 1286
<212> TYPE: DNA
<213> ORGANISM: Homo sapiens

<400> SEQUENCE: 1

```
cggatcgcgg gctcgggctg cggggctccg gctgcgggcg ctgggccgcg aggcgcggag      60
cttgggagcg gagcccaggc cgtgccgcgc ggcgccatga agggcaagga ggagaaggag     120
ggcggcgcac ggctgggcgc tggcggcgga agccccgaga agagcccgag cgcgcaggag     180
ctcaaggagc agggcaatcg tctgttcgtg ggccgaaagt acccggaggc ggcggcctgc     240
tacggccgcg tgatcacccg gaacccgctg gtggccgtgt attacaccaa ccgggccttg     300
tgctacctga agatgcagca gcacgagcag gccctggccg actgccggcg cgccctggag     360
ctggacgggc agtctgtgaa ggcgcacttc ttcctggggc agtgccagct ggagatggag     420
agctatgatg aggccatcgc caatctgcag cgagcttaca gcctggccaa ggagcagcgg     480
ctgaacttcg gggacgacat ccccagcgct cttcgaatcg cgaagaagaa gcgctggaac     540
agcattgagg agcggcgcat ccaccaggag agcgagctgc actcctacct ctccaggctc     600 attgccgcg agcgtgagag ggagctggaa gagtgccagc gaaaccacga gggtgatgag     660
gacgacagcc acgtccgggc ccagcaggcc tgcattgagg ccaagcacga caagtacatg     720
gcggacatgg acgagctttt ttctcaggtg gatgagaaga ggaagaagcg agacatcccc     780
gactacctgt gtggcaagat cagctttgag ctgatgcggg agccgtgcat cacgcccagt     840
```

```
ggcatcacct acgaccgcaa ggacatcgag gagcacctgc agcgtgtggg tcattttgac    900
cccgtgaccc ggagccccct gacccaggaa cagctcatcc ccaacttggc tatgaaggag    960
gttattgacg cattcatctc tgagaatggc tgggtggagg actactgagg ttccctgccc   1020
tacctggcgt cctggtccag gggagccctg ggcagaagcc cccggcccct atacatagtt   1080
tatgttcctg ccaccccga ccgcttcccc caagttctgc tgttggactc tggactgttt   1140 ccccctctcag catcgctttt gctgggccgt gatcgtcccc ctttgtgggc tggaaaagca   1200
ggtgagggtg ggctgggctg aggccattgc cgccactatc tgtgtaataa aatccgtgag   1260
cacgaggtgg gacgtgctgg tgtgtg                                         1286
```

<210> SEQ ID NO 2
<211> LENGTH: 303
<212> TYPE: PRT
<213> ORGANISM: Homo sapiens

<400> SEQUENCE: 2

```
Met Lys Gly Lys Glu Lys Glu Gly Gly Ala Arg Leu Gly Ala Gly
 1               5                  10                  15

Gly Gly Ser Pro Glu Lys Ser Pro Ser Ala Gln Glu Leu Lys Glu Gln
                20                  25                  30

Gly Asn Arg Leu Phe Val Gly Arg Lys Tyr Pro Glu Ala Ala Cys
                35                  40                  45

Tyr Gly Arg Val Ile Thr Arg Asn Pro Leu Val Ala Val Tyr Tyr Thr
        50                  55                  60

Asn Arg Ala Leu Cys Tyr Leu Lys Met Gln Gln His Glu Gln Ala Leu
65                  70                  75                  80

Ala Asp Cys Arg Arg Ala Leu Glu Leu Asp Gly Gln Ser Val Lys Ala
                85                  90                  95

His Phe Phe Leu Gly Gln Cys Gln Leu Glu Met Glu Ser Tyr Asp Glu
                100                 105                 110

Ala Ile Ala Asn Leu Gln Arg Ala Tyr Ser Leu Ala Lys Glu Gln Arg
            115                 120                 125

Leu Asn Phe Gly Asp Asp Ile Pro Ser Ala Leu Arg Ile Ala Lys Lys
        130                 135                 140

Lys Arg Trp Asn Ser Ile Glu Glu Arg Ile His Gln Glu Ser Glu
145                 150                 155                 160

Leu His Ser Tyr Leu Ser Arg Leu Ile Ala Ala Glu Arg Glu Arg Glu
                165                 170                 175

Leu Glu Glu Cys Gln Arg Asn His Glu Gly Asp Glu Asp Ser His
                180                 185                 190

Val Arg Ala Gln Gln Ala Cys Ile Glu Ala Lys His Asp Lys Tyr Met
            195                 200                 205

Ala Asp Met Asp Glu Leu Phe Ser Gln Val Asp Glu Lys Arg Lys Lys
        210                 215                 220

Arg Asp Ile Pro Asp Tyr Leu Cys Gly Lys Ile Ser Phe Glu Leu Met
225                 230                 235                 240

Arg Glu Pro Cys Ile Thr Pro Ser Gly Ile Thr Tyr Asp Arg Lys Asp
                245                 250                 255

Ile Glu Glu His Leu Gln Arg Val Gly His Phe Asp Pro Val Thr Arg
                260                 265                 270

Ser Pro Leu Thr Gln Glu Gln Leu Ile Pro Asn Leu Ala Met Lys Glu
            275                 280                 285

Val Ile Asp Ala Phe Ile Ser Glu Asn Gly Trp Val Glu Asp Tyr
```

```
                290             295             300
```

<210> SEQ ID NO 3
<211> LENGTH: 34
<212> TYPE: PRT
<213> ORGANISM: Homo sapiens

<400> SEQUENCE: 3

Ala Asn Asp Lys Lys Val Ala Ala Ile Glu Ala Leu Asn Asp Gly Glu
1               5                   10                  15

Leu Gln Lys Ala Ile Asp Leu Phe Thr Asp Ala Ile Lys Leu Asn Pro
            20                  25                  30

Arg Leu

<210> SEQ ID NO 4
<211> LENGTH: 34
<212> TYPE: PRT
<213> ORGANISM: Homo sapiens

<400> SEQUENCE: 4

Ala Glu Glu Leu Lys Thr Gln Ala Asn Asp Tyr Phe Lys Ala Lys Asp
1               5                   10                  15

Tyr Glu Asn Ala Ile Lys Phe Tyr Ser Gln Ala Ile Glu Leu Asn Pro
            20                  25                  30

Ser Asn

<210> SEQ ID NO 5
<211> LENGTH: 34
<212> TYPE: PRT
<213> ORGANISM: Homo sapiens

<400> SEQUENCE: 5

Thr Glu Asp Leu Lys Asn Ile Gly Asn Thr Phe Phe Lys Ser Gln Asn
1               5                   10                  15

Trp Glu Met Ala Ile Lys Lys Tyr Ala Glu Val Leu Arg Tyr Val Asp
            20                  25                  30

Ser Ser

<210> SEQ ID NO 6
<211> LENGTH: 34
<212> TYPE: PRT
<213> ORGANISM: Artificial Sequence
<220> FEATURE:
<223> OTHER INFORMATION: consensus sequence
<221> NAME/KEY: UNSURE
<222> LOCATION: (2)..(2)
<223> OTHER INFORMATION: no amino acid present at an overwhelming
      frequency
<221> NAME/KEY: UNSURE
<222> LOCATION: (3)..(3)
<223> OTHER INFORMATION: no amino acid present at an overwhelming
      frequency
<221> NAME/KEY: UNSURE
<222> LOCATION: (9)..(9)
<223> OTHER INFORMATION: no amino acid present at an overwhelming
      frequency
<221> NAME/KEY: UNSURE
<222> LOCATION: (10)..(10)
<223> OTHER INFORMATION: no amino acid present at an overwhelming
      frequency
<221> NAME/KEY: UNSURE
<222> LOCATION: (11)..(11)
<223> OTHER INFORMATION: no amino acid present at an overwhelming
      frequency
<221> NAME/KEY: UNSURE
<222> LOCATION: (15)..(15)

-continued

```
<223> OTHER INFORMATION: no amino acid present at an overwhelming
      frequency
<221> NAME/KEY: UNSURE
<222> LOCATION: (16)..(16)
<223> OTHER INFORMATION: no amino acid present at an overwhelming
      frequency
<221> NAME/KEY: UNSURE
<222> LOCATION: (19)..(19)
<223> OTHER INFORMATION: no amino acid present at an overwhelming
      frequency
<221> NAME/KEY: UNSURE
<222> LOCATION: (25)..(25)
<223> OTHER INFORMATION: no amino acid present at an overwhelming
      frequency
<221> NAME/KEY: UNSURE
<222> LOCATION: (33)..(33)
<223> OTHER INFORMATION: no amino acid present at an overwhelming
      frequency
<221> NAME/KEY: UNSURE
<222> LOCATION: (34)..(34)
<223> OTHER INFORMATION: no amino acid present at an overwhelming
      frequency

<400> SEQUENCE: 6

Ala Xaa Xaa Tyr Lys Asn Arg Ala Xaa Xaa Xaa Leu Lys Leu Xaa Xaa
 1               5                  10                  15

Tyr Glu Xaa Ala Ile Ala Asp Tyr Xaa Arg Ala Ile Glu Leu Asp Pro
            20                  25                  30

Xaa Xaa

<210> SEQ ID NO 7
<211> LENGTH: 304
<212> TYPE: PRT
<213> ORGANISM: Mus musculus

<400> SEQUENCE: 7

Met Lys Gly Lys Glu Lys Glu Gly Gly Ala Arg Leu Gly Thr Gly Gly
 1               5                  10                  15

Gly Gly Gly Ser Pro Asp Lys Ser Pro Ser Ala Gln Glu Leu Lys Glu
            20                  25                  30

Gln Gly Asn Arg Leu Phe Val Gly Arg Lys Tyr Pro Glu Ala Ala Ala
        35                  40                  45

Cys Tyr Gly Arg Ala Ile Thr Arg Asn Pro Leu Val Ala Val Tyr Tyr
    50                  55                  60

Thr Asn Arg Ala Leu Cys Tyr Leu Lys Met Gln Gln Pro Glu Gln Ala
65                  70                  75                  80

Leu Ala Asp Cys Arg Arg Ala Leu Glu Leu Asp Gly Gln Ser Val Lys
                85                  90                  95

Ala His Phe Phe Leu Gly Gln Cys Gln Leu Glu Met Glu Ser Tyr Asp
            100                 105                 110

Glu Ala Ile Ala Asn Leu Gln Arg Ala Tyr Ser Leu Ala Lys Glu Gln
        115                 120                 125

Arg Leu Asn Phe Gly Asp Asp Ile Pro Ser Ala Leu Arg Ile Ala Lys
    130                 135                 140

Lys Lys Arg Trp Asn Ser Ile Glu Glu Arg Ile His Gln Glu Ser
145                 150                 155                 160

Glu Leu His Ser Tyr Leu Thr Arg Leu Ile Ala Ala Glu Arg Glu Arg
                165                 170                 175

Glu Leu Glu Glu Cys Gln Arg Asn His Glu Gly His Glu Asp Asp Gly
            180                 185                 190

His Ile Arg Ala Gln Gln Ala Cys Ile Glu Ala Lys His Asp Lys Tyr
        195                 200                 205
```

Met Ala Asp Met Asp Glu Leu Phe Ser Gln Val Asp Glu Lys Arg Lys
210                 215                 220

Lys Arg Asp Ile Pro Asp Tyr Leu Cys Gly Lys Ile Ser Phe Glu Leu
225                 230                 235                 240

Met Arg Glu Pro Cys Ile Thr Pro Ser Gly Ile Thr Tyr Asp Arg Lys
                245                 250                 255

Asp Ile Glu Glu His Leu Gln Arg Val Gly His Phe Asp Pro Val Thr
                260                 265                 270

Arg Ser Pro Leu Thr Gln Glu Gln Leu Ile Pro Asn Leu Ala Met Lys
            275                 280                 285

Glu Val Ile Asp Ala Phe Ile Ser Glu Asn Gly Trp Val Glu Asp Tyr
290                 295                 300

<210> SEQ ID NO 8
<211> LENGTH: 289
<212> TYPE: PRT
<213> ORGANISM: Drosophila melanogaster

<400> SEQUENCE: 8

Met Thr Thr Lys His Ile Tyr Ser Thr Thr Asn Leu Ser Asp Leu Gln
1               5                   10                  15

Leu Lys Glu Gln Gly Asn Cys Leu Phe Ala Ala Arg Lys Tyr Asp Asp
            20                  25                  30

Ala Ile Asn Cys Tyr Ser Lys Ala Ile Ile Lys Asn Pro Thr Asn Ala
        35                  40                  45

Thr Tyr Phe Thr Asn Arg Ala Leu Cys Asn Leu Lys Leu Lys Arg Trp
50                  55                  60

Glu Leu Cys Cys Gln Asp Ser Arg Arg Ala Leu Asp Ile Asp Gly Asn
65                  70                  75                  80

Leu Leu Lys Gly His Phe Phe Leu Gly Gln Gly Leu Met Glu Ile Asp
                85                  90                  95

Asn Phe Asp Glu Ala Ile Lys His Leu Gln Arg Ala Tyr Asp Leu Ser
            100                 105                 110

Lys Glu Gln Lys Gln Asn Phe Gly Asp Asp Ile Thr Leu Gln Leu Arg
        115                 120                 125

Leu Ala Arg Lys Lys Arg Trp Asn Val Met Glu Glu Lys Arg Ile Gln
130                 135                 140

Gln Glu Ile Glu Leu Gln Ser Tyr Leu Asn Gly Leu Ile Lys Gly Asp
145                 150                 155                 160

Met Glu Ser Arg Leu Ala Asn Leu Lys Leu Asn Gly Asn Val His Asp
                165                 170                 175

Glu Gln Leu Lys Asp Lys Gln Gln Glu Ile Gln Glu Cys Asp Asp
            180                 185                 190

His Ile Lys Glu Leu Asn Asn Ile Phe Ser Lys Val Asp Glu Arg Arg
        195                 200                 205

Lys Lys Arg Glu Val Pro Asp Phe Leu Cys Gly Lys Ile Ser Phe Glu
210                 215                 220

Ile Leu Thr Asp Pro Val Ile Thr Pro Ser Gly Ile Thr Tyr Glu Arg
225                 230                 235                 240

Lys Asp Ile Glu Glu His Leu Gln Arg Val Gly His Phe Asp Pro Val
                245                 250                 255

Thr Arg Val Lys Leu Thr Gln Asp Gln Leu Ile Pro Asn Phe Ser Met
            260                 265                 270

Lys Glu Val Val Asp Ser Phe Ile Ala Glu Asn Glu Trp Ser Leu Asp

Tyr

<210> SEQ ID NO 9
<211> LENGTH: 1218
<212> TYPE: DNA
<213> ORGANISM: Mus musculus

<400> SEQUENCE: 9

| | | | | | |
|---|---|---|---|---|---|
| gggctgcgag | atctaggtgg | ccgggcgcgg | agcccaagcc | gtgccgcgcg | gcgccatgaa | 60 |
| gggcaaggag | gaaaaggagg | gcggcgcgcg | gctgggcact | ggtggcggcg | gcagccctga | 120 |
| taagagcccg | agtgcgcaag | agctcaagga | gcagggaaac | cggctcttcg | tgggccgcaa | 180 |
| gtacccggag | gcggcggcct | gctacggccg | cgccatcact | cggaacccac | ttgtggcagt | 240 |
| gtactacacc | aaccgggccc | tgtgctatct | gaagatgcag | cagcctgaac | aggcacttgc | 300 |
| tgactgccgc | cgagccctgg | agctggacgg | cagtctgtg | aaggcgcact | tcttcctggg | 360 |
| gcagtgccag | ctggagatgg | agagttatga | tgaggccatt | gccaatctgc | agcgagccta | 420 |
| tagtttggcc | aaggagcagc | gactcaactt | tggggatgat | attcctagtg | cccttcgcat | 480 |
| tgctaagaag | aagcgctgga | acagtatcga | ggaacggcgc | atccaccagg | agagtgagct | 540 |
| gcattcatat | ctcaccaggc | tcattgctgc | tgagcgagag | agggaactgg | aggagtgtca | 600 |
| gcggaaccac | gagggtcatg | aagatgatgg | ccacatccgg | gcccagcagg | cctgcattga | 660 |
| ggccaagcac | gataaataca | tggcagatat | ggatgagctc | ttctctcagg | tggacgagaa | 720 |
| aagaaagaag | cgagatatcc | ctgactactt | gtgtggcaag | attagctttg | agctgatgcg | 780 |
| ggaaccctgc | attacaccca | gtggtatcac | ctatgaccgc | aaggacattg | aggagcacct | 840 |
| gcagcgtgtg | ggccactttg | accctgtgac | ccggagccct | ctgacccagg | aacagctcat | 900 |
| ccccaacttg | gccatgaagg | aagtcattga | cgctttcatc | tctgagaacg | gctgggtaga | 960 |
| ggactattga | ggccccatgt | cctgcctggc | accctggccc | aggaggatct | ggagacggaa | 1020 |
| gctccagtcc | ctgtatagtt | tgtgtccctg | ggcctgcccc | catcggccct | gctgatgggt | 1080 |
| tctgaactgc | tccccttctc | agcatacccc | ttgctggacc | atgagcctcc | cttgtccccc | 1140 |
| ttctgggctg | gagagtgggt | gagggtgggc | tgaggttgct | gctgctgcca | ctgtcctgta | 1200 |
| ataaagtctg | tgagcact | | | | | 1218 |

<210> SEQ ID NO 10
<211> LENGTH: 1225
<212> TYPE: DNA
<213> ORGANISM: Drosophila melanogaster

<400> SEQUENCE: 10

| | | | | | |
|---|---|---|---|---|---|
| aaaattgttt | tatgtttaat | taaatacagg | cgaatagctc | aagatctttt | tggtgttatg | 60 |
| agcgttcaaa | agtcactacc | gtttcccact | taatactttg | ttaactgtta | agttcgtgca | 120 |
| gcagttcccc | aattcttgca | gaggaaacaa | atttacgagt | gcttcggtgt | tgttggacac | 180 |
| acactcactt | ttcatcggtg | gaaaatcaaa | tttgggacca | ggcgcagaag | attcgtcagg | 240 |
| atgacgacca | agcacatcta | ttccacgacc | aatttatcag | atctgcaatt | aaaggagcag | 300 |
| ggaaactgct | tgtttgcagc | ccgaaaatat | gacgacgcaa | taaattgcta | ctcaaaggcc | 360 |
| atcataaaga | accccacaaa | cgccacatac | ttcacaaacc | gagccctctg | caacctgaaa | 420 |
| ctgaagagat | gggaactgtg | ctgccaggat | agtcggcgcg | ccctcgacat | cgatgggaat | 480 |
| ctgttgaagg | gtcacttctt | cctgggccaa | ggactcatgg | aaatcgacaa | cttgacgag | 540 |

-continued

```
gctataaagc accttcaacg ggcatacgat ctgtccaagg agcagaagca aaactttggg      600
gatgatatta cactacagtt gcgactagct cgcaaaaagc gctggaatgt tatggaggag      660
aagcgaatac agcaggaaat cgagctgcaa agctatttaa atggtctaat aaaagggac       720 atggaaagcc gtttggccaa tttaaagctg aatggaaatg tacacgatga gcagctgaaa      780
gacaagcaac aggaaattga gcaagaatgc gatgaccata ttaaggaact taacaatata      840
ttttctaagg ttgacgaacg tcgaaagaaa cgtgaagttc ccgattttct atgtggcaaa      900
ataagttttg aaatattaac agaccctgtg ataactccat ctggaattac gtatgaacga      960
aaagatatag aagaacactt gcagcgggtt ggacatttcg atcctgtgac acgcgttaag     1020
ctcactcagg atcaactaat accaaatttt tcaatgaagg aagtggttga ctcttttatt     1080
gccgagaatg aatggtcttt agattattaa gttacttatt agttggcatt gtcattgtaa     1140
ttgattagat gttagaaccc agttcccatt gtctaaaaac cagataagtg ataataaatg     1200
tggatctgca attgagattt atatg                                           1225
```

<210> SEQ ID NO 11
<211> LENGTH: 5246
<212> TYPE: DNA
<213> ORGANISM: Homo sapiens

<400> SEQUENCE: 11

```
ctgtgggagc tgggggcacg cgggatggct gggggccggg cgtgtggtca ggccaggtgt       60
gtggtcaggc cgggtgtgtg atcaggcgtg agtttgggaa gtgtttattg agctcccgta      120
gtggccagcc tcctcttcag cctccctgcc gtccagtgag acccggaggc ctgaggttct      180
gtggcaggtg agcaggcctg ggccatggcc aagtttactc ggcctgggtt ccatgcttct      240
tggctggcct agcatcctcg tgggtggcca ggctggggcc aaggttgggc agcaggtctg      300
ggcacagcct ctgccccaca gcccaggtcc acagtgctgt ctccactagg tagggagtcc      360
actgtcctga ggcactggct agggaggggc acacggactc aggcccaggg gcacgggcca      420
ccccaacctg cccacacaca gttcattccc cttggctcag agctgtggcc cgctcttgaa      480
cctggcccag gtacagcagg tagtacctga gggtgtactg tggggccggc cagccgggca      540
ctgtggccac cgcctcatct gacatgaagg cctccatctc tggagctcca gctgccagga      600
ctgctgtgaa cagcgaggag aagcagccag acacacccca tcaggacaag ctctgggaga      660
ccctgctccc agcagcccag ggccctatgg ttcctgctcc tagcgacacg caagggccca      720
gactgcccgc ttcacagaca agaacgccta tgtacccaag tcgtgcccac ccaactcacc      780
cgaggctgtg gtgggcccac accgcagagg gcacacagct cggtgactgc agcccccaca      840
tctggcagga ggcagaaggt ggcggtcgaa cagtgcacaa ccagctcagg gggattggtg      900
gccaccagct gctgcagacg tggccggaag cgccctctg tgggaggcca ggtcagggtg       960 cctgggtgc tggacccacc agggaggccc cgcccccact ggagacaccc gccccgccga     1020
tgccacgccc caatgaagac ccgcgctacg gaggccctgc cctcggggcg ggccgccctt     1080
cacagtcaag ctgccaggcc agcagccgct ccagctccct gtcacatgct tctctgctct     1140 gccctgatg gccgctggca actcttcccg ataccctgagg aagggcggtg aggggaggac     1200
tggccacgga ggacgctcgc cccaccgatc tctatcccct tccactctac caacagtccg     1260
gggcttccag ccgccctcgg gggctcgcgc tcgcccgtag cacctctcgt ggcgctccag     1320
aatggcagcc cagcgactgg ggtcctcaca ccccacagcg cgtgggaagc cgctacgttc     1380
```

-continued

```
acgcgcaggg gcgggaggcg gcggctgggg gcggggcctc tgctgatggg gccgggtgct      1440
gggggcgggg cctctggatt gggcggttgc tgggggcggg gcctctgcgg atggggctgg      1500
gggcggggcc tctgctgatg gggccggcgg ctggggcgg  ggcctctgga ttgggcgcgt     1560 gctggggcg  gggcctctgc ggatgggccc ggctgctggg ggcggggcct ctggatgggg     1620
ccggctgccg ggggagggt  ctctgcgcgt tgggacaggg gcggaacccc aggtggtcgg     1680
gacaggctgt tgcgggagcg cgccctcagc gaagcaagtg aggcatctca ctgggaaagt     1740
cgaatgtgtg tggcggccgc cgccgaggcg ggttccgaag agacctcagc agggcaggcc     1800
agggcctacg cgaacgccca cccttaagag cgcggggaca gggaactgga gcgttcctcc     1860
cagcccccga cgtcgcgggc ccagtgtccc cgtccaggct ggttgggcgc acgcgcggcc     1920
ccactcgccc ccacgcgtgc gtccccgctg gtcccgcccc cggccggaag ttccggcggc     1980
ggagctgggc cgggcccgag cggatcgcgg gctcgggctg cggggctccg gctgcgggcg     2040
ctgggccgcg aggcgcggag cttgggagcg gagcccaggc cgtgccgcgc ggcgccatga     2100
agggcaagga ggagaaggag ggcggcgcac ggctgggcgc tggcggcgga agccccgaga     2160
agagcccgag cgcgcaggag ctcaaggagc agggcaatcg tctgttcgtg ggccgaaagt     2220
acccggaggc ggcggcctgc tacggccgcg cgatcgtgag tgcgcccgcg cggggagggc     2280
ggcggcggtg gcaccgggga gggcgggcc  cgggccggc  cggccccacc gagggtctgg     2340
ctcctcttcg gggcgtgtcc tcggctccca agcccagcc  gtggttctcg agcccagcgc     2400
cgggtgccgg agaacgaggg tgcgatgctg gatggaggcc ggccgggtgg ggggagggca     2460
ggggccctcg acccttgagg accccaggtc ctaagcccgg actctccaaa gatttggaaa     2520
actttacaaa accaagtgga atcaagcgga taggctcagc cagtactcca ctgtgcacag     2580
atccttggac ccagggcctt tgacaactga gaaacctagt ttcttgattc tagccagagc     2640
gcagaagctg ggacgggccg tgggtcagag tgggcacgct gagcctacgc cctcatgcgg     2700
ctggcccggc cttggtccct agacccggaa cccgctggtg gccgtgtatt acaccaaccg     2760
ggccttgtgc tacctgaaga tgcagcagca cgagcaggcc ctggccgact gccggcgcgc     2820
cctggagctg gacgggcagt ctgtgaaggc gcacttcttc ctggggcagt gccagctgga     2880
gatggagagc tatgatgagg ccatcgccaa tctgcagcga ggttggctga caagctgccc     2940
ggttgtgggg cctctggggc caggcgggtg gactggccag agagtgacgt gaagcccccg     3000
ttccccagct tacagcctgg ccaaggagca gcggctgaac ttcggggacg acatccccag     3060
cgctcttcga atcgcgaaga agaagcgctg gaacagcatt gaggagcggc gcatccacca     3120
ggagagcgag ctgcactcct acctctccag gctcattgcc gcggagcgtg agaggtggga     3180 cccctcacccc aggccgccct gtcttgggat aattctgaat caccgactcc cgacacaagc     3240
gtttatcgaa ggctttactg gcaagcagga aatgtgggga agtgtggatg ttagctctga     3300
gattggggtg tggtcagaca tctggccagg tccatctctg accggctcct ggtcaacccc     3360
cagggagctg gaagagtgcc agcgaaacca cgagggtgat gaggacgaca gccacgtccg     3420
ggcccagcag gcctgcattg aggccaagca cgtgagggtg ccccccaccc acatgtgggt     3480
ctgtgtgtgt gcacgtggcg tgggagcatc cccgccttgt gttgggtctg tgccccatgg     3540
aggagggagg tggggtgtct ccccaagca  cagcactcaa ctcttcacag acaagtaca      3600 tggcggacat ggacgagctt ttttctcagg tgatgagaa  gaggaaggtg agtgtgtgtc     3660
gcttgctgcc gatggctggc aggtgctcgt gcagtgcccc ttttcagcct ctgaccgtgt     3720
gcccctgtgc cacagaagcg agacatcccc gactacctgt gtggcaagat cagctttgag     3780
```

-continued

```
ctgatgcggg agccgtgcat cacgcccagt ggcatcacct acgaccgcaa ggacatcgag    3840
gagcacctgc aggtgaggcc tgcggctggg ggagcagggc cagtggcatg gtcctgggcc    3900
ccatgactgc cctctgccct tcttgtcact gcagcgtgtg ggtcattttg accccgtgac    3960
ccggagcccc ctgacccagg aacagctcat ccccaacttg gctatgaagg aggttattga    4020
cgcattcatc tctgagaatg gctgggtgga ggactactga ggttccctgc cctacctggc    4080
gtcctggtcc aggggagccc tgggcagaag cccccggccc ctatacatag tttatgttcc    4140
tggccacccc gaccgcttcc cccaagttct gctgttggac tctggactgt ttccctctc     4200 agcatcgctt ttgctgggcc gtgatcgtcc ccctttgtgg gctggaaaag caggtgaggg    4260
tgggctgggc tgaggccatt gccgccacta tctgtgtaat aaaatccgtg agcacgaggt    4320
gggacgtgct ggtgtgtgac cggcagtcct gccagctgtt ttggctagcc gaggaaggtg    4380
gagatgaaga cgctggtgtc aaggttgagc gtagcatgcc accagcggtc ggggaagtac    4440
agcacctggt ggaggaaggg ggtgcagcag agattagctg cgggcctcta gcctggcctg    4500
gccctctcct gccagccact gacctcacca gcccggatgg tacactccag gggccgtgca    4560
gacggtggca gggcttgagc agcagtgtca cccttgcccg ttttggtcag cgagtcccaa    4620
gcctcaaccc ccaccccgtg ctgaccttac gaccgtagat cacttctgag tacccgggtc    4680
catgccagtg aagggcacc  cccgagccag ctcctgtggg gttatgagca cctggtgacc    4740
aacccatttt gtactcaccg acagaagcct cagtccttcc cagtcccaag aagcacccac    4800
ctgcgattcc aaagctgtaa gctggagcgg ttcccagcag gccaaatggg ggtggggagt    4860
agtgccgaaa gagagaggcc cactcggtga agttgttgtc cccgaagaag tacagggtgt    4920
ctgccaacag agacggcggg gacagggatc ctggcacctg gagactccaa gcgtccccac    4980
cccctaccgc cgcctagggc tgcctcacca ttgcccaggg aggtggggtc ctgggggtgc    5040
agcagctgct ccacatactc ctggaagggc aagtccactg caggaaagag acgggtcagg    5100
accgtctggt ccagccgccc cggtgttggc aaatgggcgg gccccagggg tgaggccgcg    5160
tacctttgtg gtaggagtag gtgttggcgg tgctcagccg gaccactctg tccccaaacg    5220
aagccagcaa cctgtcgcgg gagcac                                        5246
```

<210> SEQ ID NO 12
<211> LENGTH: 303
<212> TYPE: PRT
<213> ORGANISM: Artificial Sequence
<220> FEATURE:
<223> OTHER INFORMATION: consensus sequence
<221> NAME/KEY: UNSURE
<222> LOCATION: (15)..(15)
<223> OTHER INFORMATION: unique or no amino acid in sequences being
      compared
<221> NAME/KEY: UNSURE
<222> LOCATION: (21)..(21)
<223> OTHER INFORMATION: unique or no amino acid in sequences being
      compared
<221> NAME/KEY: UNSURE
<222> LOCATION: (76)..(76)
<223> OTHER INFORMATION: unique amino acid in sequences being compared
<221> NAME/KEY: UNSURE
<222> LOCATION: (166)..(166)
<223> OTHER INFORMATION: unique amino acid in sequences being compared
<221> NAME/KEY: UNSURE
<222> LOCATION: (191)..(191)
<223> OTHER INFORMATION: unique amino acid in sequences being compared
<221> NAME/KEY: UNSURE
<222> LOCATION: (193)..(193)
<223> OTHER INFORMATION: unique amino acid in sequences being compared

<400> SEQUENCE: 12

Met Lys Gly Lys Glu Glu Lys Glu Gly Gly Ala Arg Leu Gly Xaa Gly
1               5                   10                  15

Gly Gly Ser Pro Xaa Lys Ser Pro Ser Ala Gln Glu Leu Lys Glu Gln
            20                  25                  30

Gly Asn Arg Leu Glu Val Gly Arg Lys Tyr Pro Glu Ala Ala Ala Cys
            35                  40                  45

Tyr Gly Arg Ala Ile Thr Arg Asn Pro Leu Val Ala Val Tyr Tyr Thr
    50                  55                  60

Asn Arg Ala Leu Cys Tyr Leu Lys Met Gln Gln Xaa Glu Gln Ala Leu
65                  70                  75                  80

Ala Asp Cys Arg Arg Ala Leu Glu Leu Asp Gly Gln Ser Val Lys Ala
                85                  90                  95

His Phe Phe Leu Gly Gln Cys Gln Leu Glu Met Glu Ser Tyr Asp Glu
            100                 105                 110

Ala Ile Ala Asn Leu Gln Arg Ala Tyr Ser Leu Ala Lys Glu Gln Arg
            115                 120                 125

Leu Asn Phe Gly Asp Asp Ile Pro Ser Ala Leu Arg Ile Ala Lys Lys
130                 135                 140

Lys Arg Trp Asn Ser Ile Glu Glu Arg Arg Ile His Gln Glu Ser Glu
145                 150                 155                 160

Leu His Ser Tyr Leu Xaa Arg Leu Ile Ala Ala Glu Arg Glu Arg Glu
                165                 170                 175

Leu Glu Glu Cys Gln Arg Asn His Glu Gly Asp Glu Asp Xaa His
            180                 185                 190

Xaa Arg Ala Gln Gln Ala Cys Ile Glu Ala Lys His Asp Lys Tyr Met
    195                 200                 205

Ala Asp Met Asp Glu Leu Phe Ser Gln Val Asp Glu Lys Arg Lys Lys
    210                 215                 220

Arg Asp Ile Pro Asp Tyr Leu Cys Gly Lys Ile Ser Phe Glu Leu Met
225                 230                 235                 240

Arg Glu Pro Cys Ile Thr Pro Ser Gly Ile Thr Tyr Asp Arg Lys Asp
                245                 250                 255

Ile Glu Glu His Leu Gln Arg Val Gly His Phe Asp Pro Val Thr Arg
            260                 265                 270

Ser Pro Leu Thr Gln Glu Gln Leu Ile Pro Asn Leu Ala Met Lys Glu
    275                 280                 285

Val Ile Asp Ala Phe Ile Ser Glu Asn Gly Trp Val Glu Asp Tyr
290                 295                 300

<210> SEQ ID NO 13
<211> LENGTH: 34
<212> TYPE: PRT
<213> ORGANISM: Homo sapiens

<400> SEQUENCE: 13

Thr Lys Ala Leu Tyr Arg Arg Ala Gln Gly Trp Gln Gly Leu Lys Glu
1               5                   10                  15

Tyr Asp Gln Ala Leu Ala Asp Leu Lys Lys Ala Gln Gly Ile Ala Pro
            20                  25                  30

Glu Asp

<210> SEQ ID NO 14
<211> LENGTH: 20
<212> TYPE: DNA

-continued

<213> ORGANISM: Artificial Sequence
<220> FEATURE:
<223> OTHER INFORMATION: primer

<400> SEQUENCE: 14
gctgtaagct cgctgcagat                                           20

<210> SEQ ID NO 15
<211> LENGTH: 23
<212> TYPE: DNA
<213> ORGANISM: Artificial Sequence
<220> FEATURE:
<223> OTHER INFORMATION: primer

<400> SEQUENCE: 15
gcctcatcat agctctccat ctc                                       23

<210> SEQ ID NO 16
<211> LENGTH: 34
<212> TYPE: PRT
<213> ORGANISM: Homo sapiens

<400> SEQUENCE: 16

Ala Ile Leu Tyr Ala Lys Arg Ala Ser Val Phe Val Lys Leu Gln Lys
1               5                   10                  15

Pro Asn Ala Ala Ile Arg Asp Cys Asp Arg Ala Ile Glu Ile Asn Pro
            20                  25                  30

Asp Ser

<210> SEQ ID NO 17
<211> LENGTH: 34
<212> TYPE: PRT
<213> ORGANISM: Homo sapiens

<400> SEQUENCE: 17

Ala Gln Pro Tyr Lys Trp Arg Gly Lys Ala His Arg Leu Leu Gly His
1               5                   10                  15

Trp Glu Glu Ala Ala His Asp Leu Ala Leu Ala Cys Lys Leu Asp Tyr
            20                  25                  30

Asp Glu

<210> SEQ ID NO 18
<211> LENGTH: 34
<212> TYPE: PRT
<213> ORGANISM: Homo sapiens

<400> SEQUENCE: 18

Ala Ile Tyr Tyr Gly Asn Arg Ser Leu Ala Tyr Leu Arg Thr Glu Cys
1               5                   10                  15

Tyr Gly Tyr Ala Leu Gly Asp Ala Thr Arg Ala Ile Glu Leu Asp Lys
            20                  25                  30

Lys Tyr

<210> SEQ ID NO 19
<211> LENGTH: 34
<212> TYPE: PRT
<213> ORGANISM: Homo sapiens

<400> SEQUENCE: 19

Ile Lys Gly Tyr Tyr Arg Arg Ala Ala Ser Asn Met Ala Leu Gly Lys
1               5                   10                  15

```
Phe Arg Ala Ala Leu Arg Asp Tyr Glu Thr Val Val Lys Val Lys Pro
            20                  25                  30

His Asp

<210> SEQ ID NO 20
<211> LENGTH: 34
<212> TYPE: PRT
<213> ORGANISM: Homo sapiens

<400> SEQUENCE: 20

Leu Ser Cys Val Leu Asn Ile Gly Ala Cys Lys Leu Lys Met Ser Asn
1               5                   10                  15

Trp Gln Gly Ala Ile Asp Ser Cys Leu Glu Ala Leu Glu Leu Asp Pro
            20                  25                  30

Ser Asn
```

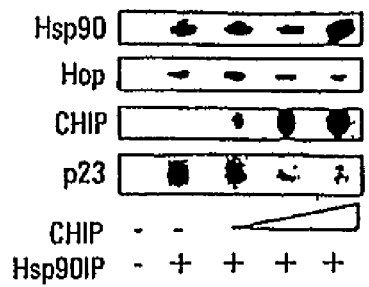
*Fig. 14A*
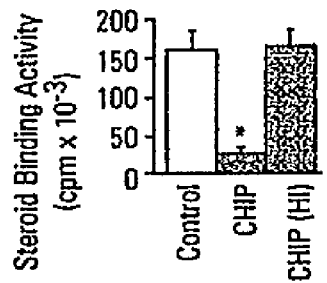
*Fig. 14D*
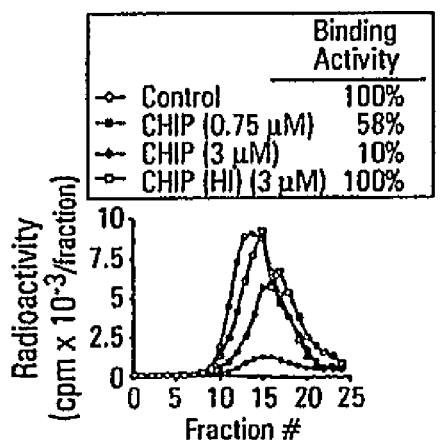
*Fig. 14B*
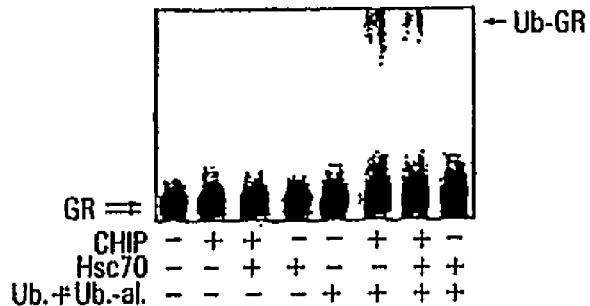
*Fig. 14E*
*Fig. 14C*
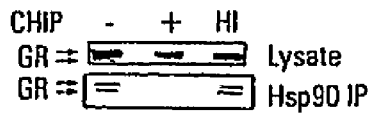

What is claimed is:

1. An isolated polypeptide comprising SEQ ID NO: 2.
2. The polypeptide of claim 1 wherein the polypeptide is a recombinant polypeptide.
3. A composition comprising the polypeptide of claim 1.
4. An isolated polypeptide comprising the amino acid sequence of amino acids 1–197 of SEQ ID NO:2, wherein the polypeptide binds to the carboxyl-terminal domain of the heat shock protein Hsc70.
5. The polypeptide of claim 4 having a molecular weight as determined by SDS polyacrylamide gel electrophoresis of about 30 kD to about 40 kD.
6. A composition comprising the polypeptide of claim 4.
7. An isolated polypeptide comprising SEQ ID NO:7.
8. A composition comprising the polypeptide of claim 7.
9. An isolated polypeptide encoded by a nucleic acid that hybridizes to the nucleic acid complement of SEQ ID NO:1 under hybridization conditions of 0.015 M NaCl/0.0015 M sodium citrate (SSC) and about 0.1% sodium dodecyl sulfate (SDS) at about 50° C. to about 65° C., wherein said polypeptide comprises at least the amino acid sequence of amino acid residues 1–197 of SEQ ID NO:2, and wherein said polypeptide binds with to the carboxyl-terminal domain of the heat shock protein Hsc70.
10. A composition comprising the polypeptide of claim 9.
11. An isolated polypeptide comprising the amino acid sequence of amino acids 1–197 of SEQ ID NO:7, wherein the polypeptide binds to the carboxyl-terminal domain of the heat shock protein Hsc70.
12. A composition comprising the polypeptide of claim 11.

* * * * *

UNITED STATES PATENT AND TRADEMARK OFFICE
CERTIFICATE OF CORRECTION

| | | |
|---|---|---|
| PATENT NO. | : 7,094,873 B1 | Page 1 of 21 |
| APPLICATION NO. | : 09/573473 | |
| DATED | : August 22, 2006 | |
| INVENTOR(S) | : Patterson et al. | |

It is certified that error appears in the above-identified patent and that said Letters Patent is hereby corrected as shown below:

On the title page, item [56]:

On page 2 under "Other Publications", column 2, line 23, delete "Graham et a.," and insert --Graham et al.,--;

Please replace sheets 1-15 of the drawings with the attached corrected drawings as filed on September 12, 2002 (20 Sheets total);

In column 2, line 1, delete "fHP" and insert --HIP--;

In column 3, line 10, delete "65C." and insert --65° C.--;

In column 19, line 19, delete "SEQ ED NOs." and insert --SEQ ID NOs.--;

In column 22, line 22, delete "ncbinlm.nih.gov." and insert --ncbi.nlm.nih.gov.--;

In column 26, line 26, delete "ether-N,N, N', N'-tetraacetic" and insert --ether -N, N, N', N'-tetraacetic--;

In column 26, line 31, delete "13,000xg" and insert --13,000 X g--;

In column 26, line 46, delete "3000xg" and insert --3000 X g--;

In column 26, line 50, delete "α-mercaptoethanol)" and insert --β-mercaptoethanol)--;

In column 32, line 9, delete "[Hep 70]".

Signed and Sealed this

Twenty-third Day of October, 2007

JON W. DUDAS
*Director of the United States Patent and Trademark Office*

```
   1                              CGGATCGCGGGCTCGGGCTGCGGGGCTCCGGCTGCG
  37  GGCGCTGGGCCGCGAGGCGCGGAGCTTGGGAGCGGAGCCCAGGCCGTGCCGCGCGGCGCC
  97  ATGAAGGGCAAGGAGGAGAAGGAGGGCGGCGCACGGCTGGGCGCTGGCGGCGGAAGCCCC
       M  K  G  K  E  E  K  E  G  G  A  R  L  G  A  G  G  G  S  P    20
 157  GAGAAGAGCCCGAGCGCGCAGGAGCTCAAGGAGCAGGGCAATCGTCTGTTCGTGGGCCGA
       E  K  S  P  S  A  Q  E  L  K  E  Q  G  N  R  L  F  V  G  R    40
 217  AAGTACCCGGAGGCGGCGGCCTGCTACGGCCGCGTGATCACCCGGAACCCGCTGGTGGCC
       K  Y  P  E  A  A  A  C  Y  G  R  V  I  T  R  N  P  L  V  A    60
 277  GTGTATTACACCAACCGGGCCTTGTGCTACCTGAAGATGCAGCAGCACGAGCAGGCCCTG
       V  Y  Y  T  N  R  A  L  C  Y  L  K  M  Q  Q  H  E  Q  A  L    80
 337  GCCGACTGCCGGCGCGCCCTGGAGCTGGACGGGCAGTCTGTGAAGGCGCACTTCTTCCTG
       A  D  C  R  R  A  L  E  L  D  G  Q  S  V  K  A  H  F  F  L   100
 397  GGGCAGTGCCAGCTGGAGATGGAGAGCTATGATGAGGCCATCGCCAATCTGCAGCGAGCT
       G  Q  C  Q  L  E  M  E  S  Y  D  E  A  I  A  N  L  Q  R  A   120
 457  TACAGCCTGGCCAAGGAGCAGCGGCTGAACTTCGGGGACGACATCCCCAGCGCTCTTCGA
       Y  S  L  A  K  E  Q  R  L  N  F  G  D  D  I  P  S  A  L  R   140
 517  ATCGCGAAGAAGAAGCGCTGGAACAGCATTGAGGAGCGGCGCATCCACCAGGAGAGCGAG
       I  A  K  K  K  R  W  N  S  I  E  E  R  R  I  H  Q  E  S  E   160
 577  CTGCACTCCTACCTCTCCAGGCTCATTGCCGCGGAGCGTGAGAGGGAGCTGGAAGAGTGC
       L  H  S  Y  L  S  R  L  I  A  A  E  R  E  R  E  L  E  E  C   180
 637  CAGCGAAACCACGAGGGTGATGAGGACGACAGCCACGTCCGGGCCCAGCAGGCCTGCATT
       Q  R  N  H  E  G  D  E  D  D  S  H  V  R  A  Q  Q  A  C  I   200
 697  GAGGCCAAGCACGACAAGTACATGGCGGACATGGACGAGCTTTTTTCTCAGGTGGATGAG
       E  A  K  H  D  K  Y  M  A  D  M  D  E  L  F  S  Q  V  D  E   220
 757  AAGAGGAAGAAGCGAGACATCCCCGACTACCTGTGTGGCAAGATCAGCTTTGAGCTGATG
       K  R  K  K  R  D  I  P  D  Y  L  C  G  K  I  S  F  E  L  M   240
 817  CGGGAGCCGTGCATCACGCCCAGTGGCATCACCTACGACCGCAAGGACATCGAGGAGCAC
       R  E  P  C  I  T  P  S  G  I  T  Y  D  R  K  D  I  E  E  H   260
 877  CTGCAGCGTGTGGGTCATTTTGACCCCGTGACCCGGAGCCCCCTGACCCAGGAACAGCTC
       L  Q  R  V  G  H  F  D  P  V  T  R  S  P  L  T  Q  E  Q  L   280
 937  ATCCCCAACTTGGCTATGAAGGAGGTTATTGACGCATTCATCTCTGAGAATGGCTGGGTG
       I  P  N  L  A  M  K  E  V  I  D  A  F  I  S  E  N  G  W  V   300
 997  GAGGACTACTGAGGTTCCCTGCCCTACCTGGCGTCCTGGTCCAGGGGAGCCCTGGGCAGA
       E  D  Y  *                                                    303
1057  AGCCCCGGCCCCTATACATAGTTTATGTTCCTGGCCACCCCGACCGCTTCCCCCAAGTT
1117  CTGCTGTTGGACTCTGGACTGTTTCCCCTCTCAGCATCGCTTTTGCTGGGCCGTGATCGT
1177  CCCCCTTTGTGGGCTGGAAAAGCAGGTGAGGGTGGGCTGGGCTGAGGCCATTGCCGCCAC
1237  TATCTGTGTAATAAAATCCGTGAGCACGAGGTGGGACGTGCTGGTGTGTG
```

*Fig. 1*

| | |
|---|---|
| Consensus | AXXYKNRAXXXLKLXXYEXAIADYXRAIELDPXX |
| hCHIP-TPR1 | AQELKEQGNRLFVGRKYPEAAACYGRVITRNPLV |
| hCHIP-TPR2 | AVYYTNRALCYLKMQQHEQALADCRRALELDGQS |
| hCHIP-TPR3 | VKAHFFLGQCQLEMESYDEAIANLQRAYSLAKEQ |
| hHIP-TPR1 | ANDKKVAAIEALNDGELQKAIDLFTDAIKLNPRL |
| hHIP-TPR2 | AILYAKRASVFVKLQKPNAAIRDCDRAIEINPDS |
| hHIP-TPR3 | AQPYKWRGKAHRLLGHWEEAAHDLALACKLDYDE |
| hPP5-TPR1 | AEELKTQANDYFKAKDYENAIKFYSQAIELNPSN |
| hPP5-TPR2 | AIYYGNRSLAYLRTECYGYALGDATRAIELDKKY |
| hPP5-TPR3 | IKGYYRRAASNMALGKFRAALRDYETVVKVKPHD |
| hCYP-TPR1 | TEDLKNIGNTFFKSQNWEMAIKKYAEVLRYVDSS |
| hCYP-TPR2 | LSCVLNIGACKLKMSNWQGAIDSCLEALELDPSN |
| hCYP-TPR3 | TKALYRRAQGWQGLKEYDQALADLKKAQGIAPED |

*Fig. 2*

Fig. 3A

```
Human ORF      MKGKEEKEGG ARLGAGGG-S PEKSPSAQEL KEQGNRLFVG RKYPEAAACY    4
Mouse ORF      MKGKEEKEGG ARLGTGGGGS PDKSPSAQEL KEQGNRLFVG RKYPEAAACY    5
Drosophila ORF MTKHIY-ST  ------- ----SDLQL KEQGNCLFAA RKYDDAINCY        3

Concsensus     MKGKEEKEGG ARLG.GGG-S P.KSPSAQEL KEQGNRLEVG RKYPEAAACY    5

Human ORF      GRVLTRNELV AVVYTNRAIC YLKMQQHEQA LADCRRAIEL DGQSVKAHFF    9
Mouse ORF      GRALTRNELV AVNYTNRAIC YLKMQQPEQA LADCRRATEL DGQSVKAHFF   10
Drosophila ORF SKAHTKNFTN ATYFTNRAIC NL-KLKRWELC CQDSRRAIDI DGNLLKGHFF   8

Consensus      GRALTRNELV AVVYTNRAIC YLKMQQ.EQA LADCRRAIEL DGQSVKAHFF   10

Human ORF      LGCCQLEMES YDEAIANLQR AYSLAKEQRL NFGDDIPSAL RIAKKKRWNS  14
Mouse ORF      LGCCQLEMES YDEAIANLQR AYSLAKEQRL NFGDDIPSAL RIAKKKRWNS  15
Drosophila ORF LGGLMEIDN FDEAIKHLQR AYDESKEQKQ NFGDDITLQL RLARKKRWNV  16

Consensus      LGCCQLEMES YDEAIANLQR AYSLAKEQRL NFGDDIPSAL RIAKKKRWNS  15

Human ORF      IEERRIHQES ELHSYLSRLI AAERERELEE CQRNHEGDED DSHVRAQQAC  19
Mouse ORF      IEERRIHQES ELHSYLTRLI AAERERELEE CQRNHECHED DGHIRAQQAC  20
Drosophila ORF MEEKRIQQEI ELQSYLNGLI KGDMESRHAN --LKLNCNVH DEQLKDKQQE  18

Consensus      IEERRIHQES ELHSYL.RLI AAERERELEE CQRNHEGDED D.H.RAQQAC  20
```

```
Human ORF         IEAKHDKYMA  DMDELFSQVD  EKRKKRDIPD  VLCGKISFEL  MREECITPSG   24
Mouse ORF         IEAKHDKYMA  DMDELFSQVD  EKRKKRDIPD  VLCGKISFEL  MREECITPSG   25
Drosophila ORF    IEQECDDHIK  ELNNIFSKVD  ERRKKREVPD  FLGGKISFEI  LTDFVTPRSG   23

Consensus         IEAKHDKYMA  DMDELFSQVD  EKRKKRDIPD  VLCGKISFEL  MREECITPSG   25

Human ORF         ITYDRKDIEE  HLQRVGHFDP  VTRSPLTQEQ  LIPNLAMKEV  IDAFISENGM   29
Mouse ORF         ITYDRKDIEE  HLQRVGHFDP  VTRSPLTQEQ  LIPNLAMKEV  IDAFISENGM   30
Drosophila ORF    ITYERKDIEE  HLQRVGHFDP  VTRVKLTQDQ  LIPNFSMKEV  IDAFISENGW   28

Consensus         ITYDRKDIEE  HLQRVGHFDP  VTRSPLTQEQ  LIPNLAMKEV  IDAFISENGM   30

Human ORF         VEDY                                                        30
Mouse ORF         VEDY                                                        30
Drosophila ORF    SLDY                                                        28

Consensus         VEDY                                                        30
```

*Fig. 3B* mouse cDNA II Sequence

```
GGGCTGCGAG ATCTAGGTGG CCGGGCGCGG AGCCCAAGCC GTGCCGCGCG    50
GCGCCATGAA GGGCAAGGAG GAAAAGGAGG GCGGCGCGCG GCTGGGCACT   100
GGTGGCGGCG GCAGCCCTGA TAAGAGCCCG AGTGCGCAAG AGCTCAAGGA   150
GCAGGGAAAC CGGCTCTTCG TGGGCCGCAA GTACCCGGAG GCGGCGGCCT   200
GCTACGGCCG CGCCATCACT CGGAACCCAC TTGTGGCAGT GTACTACACC   250
AACCGGGCCC TGTGCTATCT GAAGATGCAG CAGCCTGAAC AGGCACTTGC   300
TGACTGCCGG CGAGCCCTGG AGCTGGACGG GCAGTCTGTG AAGGCGCACT   350
TCTTCCTGGG GCAGTGCCAG CTGGAGATGG AGAGTTATGA TGAGGCCATT   400
GCCAATCTGC AGCGAGCCTA TAGTTTGGCC AAGGAGCAGC GACTCAACTT   450
TGGGGATGAT ATTCCTAGTG CCCTTCGCAT TGCTAAGAAG AAGCGCTGGA   500
ACAGTATCGA GGAACGGCGC ATCCACCAGG AGAGTGAGCT GCATTCATAT   550
CTCACCAGGC TCATTGCTGC TGAGCGAGAG AGGGAACTGG AGGAGTGTCA   600
GCGGAACCAC GAGGGTCATG AAGATGATGG CCACATCCGG GCCCAGCAGG   650
CCTGCATTGA GGCCAAGCAC GATAAATACA TGGCAGATAT GGATGAGCTC   700
TTCTCTCAGG TGGACGAGAA AAGAAAGAAG CGAGATATCC CTGACTACTT   750
GTGTGGCAAG ATTAGCTTTG AGCTGATGCG GGAACCCTGC ATTACACCCA   800
GTGGTATCAC CTATGACCGC AAGGACATTG AGGAGCACCT GCAGCGTGTG   850
GGCCACTTTG ACCCTGTGAC CCGGAGCCCT CTGACCCAGG AACAGCTCAT   900
CCCCAACTTG GCCATGAAGG AAGTCATTGA CGCTTTCATC TCTGAGAACG   950
GCTGGGTAGA GGACTATTGA GGCCCCATGT CCTGCCTGGC ACCCTGGCCC  1000
AGGAGGATCT GGAGACGGAA GCTCCAGTCC CTGTATAGTT TGTGTCCCTG  1050
GGCCTGCCCC CATCGGCCCT GCTGATGGGT TCTGAACTGC TCCCCTTCTC  1100
AGCATACCCC TTGCTGGACC ATGAGCCTCC CTTGTCCCCC TTCTGGGCTG  1150
GAGAGTGGGT GAGGGTGGGC TGAGGTTGCT GCTGCTGCCA CTGTCCTGTA  1200
ATAAAGTCTG TGAGCACT                                    1218
```

*Fig. 9A* mouse ORF II Sequence

```
MKGKEEKEGG ARLGTGGGGS PDKSPSAQEL KEQGNRLFVG RKYPEAAACY    50
GRAITRNPLV AVYYTNRALC YLKMQQPEQA LADCRRALEL DGQSVKAHFF   100
LGQCQLEMES YDEAIANLQR AYSLAKEQRL NFGDDIPSAL RIAKKKRWNS   150
IEERRIHQES ELHSYLTRLI AAERERELEE CQRNHEGHED DGHIRAQQAC   200
IEAKHDKYMA DMDELFSQVD EKRKKRDIPD YLCGKISFEL MREPCITPSG   250
ITYDRKDIEE HLQRVGHFDP VTRSPLTQEQ LIPNLAMKEV IDAFISENGW   300
VEDY                                                    304
```

*Fig. 9B*

Drosophila cDNA Sequence

```
AAAATTGTTT TATGTTTAAT TAAATACAGG CGAATAGCTC AAGATCTTTT    50
TGGTGTTATG AGCGTTCAAA AGTCACTACC GTTTCCCACT TAATACTTTG   100
TTAACTGTTA AGTTCGTGCA GCAGTTCCCC AATTCTTGCA GAGGAAACAA   150
ATTTACGAGT GCTTCGGTGT TGTTGGACAC ACACTCACTT TTCATCGGTG   200
GAAAATCAAA TTTGGGACCA GGCGCAGAAG ATTCGTCAGG ATGACGACCA   250
AGCACATCTA TTCCACGACC AATTTATCAG ATCTGCAATT AAAGGAGCAG   300
GGAAACTGCT TGTTTGCAGC CGAAAATAT GACGACGCAA TAAATTGCTA    350
CTCAAAGGCC ATCATAAAGA ACCCCACAAA CGCCACATAC TTCACAAACC   400
GAGCCCTCTG CAACCTGAAA CTGAAGAGAT GGAACTGTG CTGCCAGGAT    450
AGTCGGCGCG CCCTCGACAT CGATGGGAAT CTGTTGAAGG GTCACTTCTT   500
CCTGGGCCAA GGACTCATGG AAATCGACAA CTTTGACGAG GCTATAAAGC   550
ACCTTCAACG GCATACGAT CTGTCCAAGG AGCAGAAGCA AAACTTTGGG    600
GATGATATTA CACTACAGTT GCGACTAGCT CGCAAAAAGC GCTGGAATGT   650
TATGGAGGAG AAGCGAATAC AGCAGGAAAT CGAGCTGCAA AGCTATTTAA   700
ATGGTCTAAT AAAAGGGGAC ATGGAAAGCC GTTTGGCCAA TTTAAAGCTG   750
AATGGAAATG TACACGATGA GCAGCTGAAA GACAAGCAAC AGGAAATTGA   800
GCAAGAATGC GATGACCATA TTAAGGAACT TAACAATATA TTTTCTAAGG   850
TTGACGAACG TCGAAAGAAA CGTGAAGTTC CCGATTTTCT ATGTGGCAAA   900
ATAAGTTTTG AAATATTAAC AGACCCTGTG ATAACTCCAT CTGGAATTAC   950
GTATGAACGA AAAGATATAG AAGAACACTT GCAGCGGGTT GGACATTTCG  1000
ATCCTGTGAC ACGCGTTAAG CTCACTCAGG ATCAACTAAT ACCAAATTTT  1050
TCAATGAAGG AAGTGGTTGA CTCTTTTATT GCCGAGAATG AATGGTCTTT  1100
AGATTATTAA GTTACTTATT AGTTGGCATT GTCATTGTAA TTGATTAGAT  1150
GTTAGAACCC AGTTCCCATT GTCTAAAAAC CAGATAAGTG ATAATAAATG  1200
TGGATCTGCA ATTGAGATTT ATATG                            1225
```

*Fig. 10A*

Drosophila ORF Sequence

```
MTTKHIYSTT NLSDLQLKEQ GNCLFAARKY DDAINCYSKA IIKNPTNATY    50
FTNRALCNLK LKRWELCCQD SRRALDIDGN LLKGHFFLGQ GLMEIDNFDE   100
AIKHLQRAYD LSKEQKQNFG DDITLQLRLA RKKRWNVMEE KRIQQEIELQ   150
SYLNGLIKGD MESRLANLKL NGVHDEQLK DKQQEIEQEC DDHIKELNNI    200
FSKVDERRKK REVPDFLCGK ISFEILTDPV ITPSGITYER KDIEEHLQRV   250
GHFDPVTRVK LTQDQLIPNF SMKEVVDSFI AENEWSLDY              289
```

*Fig. 10B*

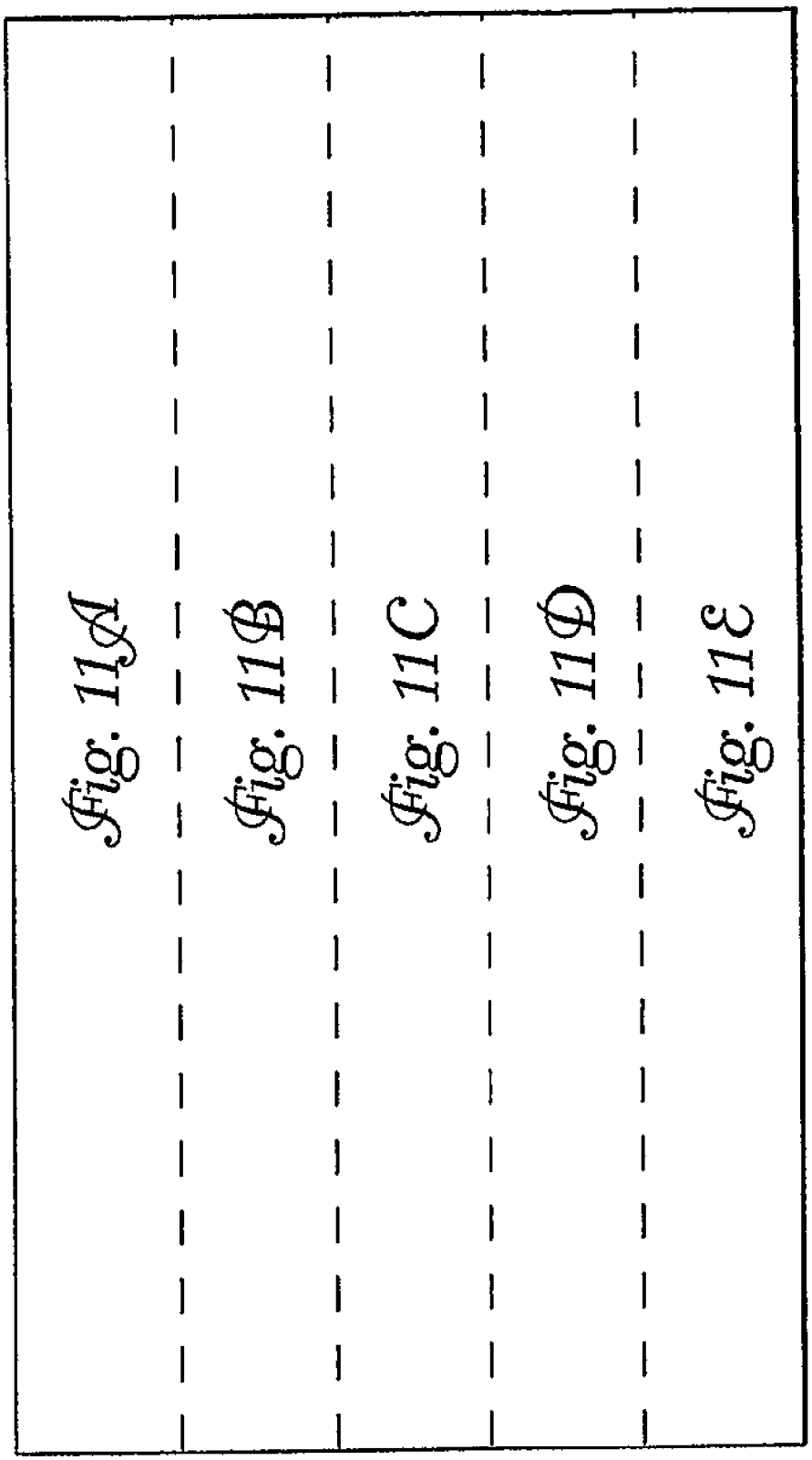

Fig. 11A

```
                          ARNT                 ARNT              MyoD
  -2000  ctgtgggagctgtgggacacgcgggatggctgggggccgggcgtgtggtcaggccaggtgtgtggtcaggccgggt
                                       ets/Nkx-2.5
  -1925  gtgtgatcagggcgtgagtttgggaagtgtttattgagctcccgtagtcccgcctcctcttcagcctccctgcc
                                                       MyoD
  -1850  gtccagtgagaccccgaggcctgaggttctgtggcaggtgagcaggcctggccatggccaagtttactcggcct
                                                            NF-1
  -1775  gggttccatgcttcttggctggcctagcatcctcgtgtggtgggccaaggttgggcagcaggtctg
               GR      NF-E2                                                 GR
  -1700  ggcacagcctctgccccacagcccagtgccagtgctgtctcccactaggagtccactgtcctgaggcac
              GR                                                      GR
  -1625  tggctagggagggcacaggactcaggccagggcccaccaacctgcccacacactgccacacagttcattccc
                                                                     MyoD
  -1550  cttggctcagagctgtggcccgtcttgaacctgtacagcaggtagtacctgagggtgtactgtgggg
                                                       GR                MyoD
  -1475  ccggccagccgggcactgtggccaccgcctcatctgacatgaaggcctccatctctggagctccagtgccagga
                                          GR                     ARNT
  -1400  ctgctgtgaacagcgaggagaagcagcagcagacacacaccccatcaggacaagtctgggagaccctgctcccagcag
                                                             ARNT        GR
  -1325  cccagggcccctatggttcctgcccaactcacccgaggctgtgtgggcccccaccccgagagggcacacagtcggtg
                              MyoD                                          CCAAT
  -1250  tgtacccaagtcgtgctgcagactgtagacaccgcagaggtggccgccgcatccaggagagacagaagacgccta
                                                                       GR
  -1175  actgcagcccccacatctggcaggaggcagaaggtgcaggtcgaacagtgcacaaccagtcagggggattggtg
              MyoD                                          NFkB          Myogenin
  -1100  gccaccagagtgctgtgcagacgtggccgcagacccccacccccactgaggaggccgatgccacccgctacg
                NFkB/Sp1                                                       GR
  -1025  ccaccaggaggcccccgccccactggagacccctcacagtcaaggccagccaagctgccaggccgcggctacg
                   Sp1                                            ets/Sp1
   -950  gaggccctgcctccgggggcggccgggcggccgcccttcacagtcaaggccgccagcggcctccagtccctgtcac
              USF        NF-E2                                    ets/GATA
   -875  atgcttctctgctcgccctgcaactcttcccgataccctgaactcttcccgatacctgaggaaggcggtgagggaggac
                                                     GATA
           Sp1
   -800  tggccacggaggaggacgctcgcgccccaccgatctctatcccttccactctaccaacagtccgggcttccagcgcc
```

```
-725  ctcggggctcgctcgcccgtagcaacctctcgtggcgctccagaatggcagccagcgactggggtcctcaca
                      Ets                                              Sp1
-650  ccccacagcgcgtgggaagccgctacgttcacgcgcaggggcggaggcggcggctggtggggggcggggcctctgctg
                         Sp1            CCAAT                            Sp1
-575  atggggccggtgctggggcggggcctctggattgggcgttgctggggggcctctgcggatgggctgg
               Sp1                                     CCAAT/Sp1        Sp1
-500  gggcggggcctctgctgatgggccctggggcgctggggcgctggggcctctgattgggcgctgtggggggccc
                Sp1                                                       Sp1
-425  tctgcggatgggccggtgctgggggcggggccctctgatgggcgctgccggggggaggggtctctgcgt
         GR      Sp1    MyoD                 GR                    NKX-2.5/IRF
-350  tgggacaggggcggaacccagtggtcggaacagcgtgttgcgggagcgcgccctcagcgaagcaagtgaggca
             C/EBP/NF-1
-275  tctccactgggaaagtcgaatgtgtgtggcgcccgcgagggttccgaagagaacctcagcagggcaggcc
                                                  GR                    ets
-200  agggcctacgcgaaccgcccaccctaagagcgcgggacagggaactgagcgttcctcccagccccgacgtcg
           GR
-125  cgggcccagtgtccccgtccaggctggttgggcgcacgcggccccactcgcccccacgcgtgcgtcccgctg
         Sp1           NFkB (pal)
-50   gtcccgccccccggccggaagttccggcgggagctggccggcggccgggccccgagCCGATCCGGCGCTCGGGG
                                       GR
+26   CTTCCGGCTGCCGCGGCTGGGCCCGAGGGGCGGCTGGGGAGCTTGGGAGCGGAGCGCGTGCGCGGCCATGA
                                                             Exon 1A         Sp1
                                                                GR
+101  AGGGCAAGGAGGAGAAGGAGAGGGGGGCCAATCGTCACGGCTGGGCCTGGCGGCCCGGAAGCCCGAGCGCGGC
+176  AGGAGCTCAAGGAGCAGGGCAATCGTCTGTTCCGTGGCCGAAAGTACCCCTGCTACCGGCCG
         E2F           EGR           Sp1
+251  CGATCgtgagtgcgcccgcggccgggggaggggccggtggcacccggggcgcggtggggcacggggcccggcc
                                                                   GR
```

*Fig. 11B*

```
+326    ccaccgagggtctgtggctcctcttcgggtcgtcctcggctccaaagccagccagccgtgttggttctcgagCCCAGCGC
+401    CGGGTGCCGAGAACGAGGGTGCGATGCTGGGATGGAGGCCGGTGGGGGAGGCAGGGCCCCTCGACCCT
+476    TGAGGACCCAGGTCCTAAGCCCGGACTCCAAAGATTTGGAAAACTTTACAAACCAAGTGGAATCAAGCGGA
```
Exon 1B
```
+551    TAGGCTCAGCCAGTACTCCACTGTGCACAGATCCTTGGACCCCAGGGCTTTGACAACTGAGAAACCTAGTTCTT
+626    GATTCTAGCCAGAGCGCAGAAGCTGGGACGAGAGCCGTGGGTCAGAGTGGGCACGCTGAGCCTACGCCCTCATGCGG
+701    CTGGCCCGGCCTTGGTCCCTAGAACCCGGAACCCGTGGCCGTGTATTACACCAACGGGCCTTGTGCTACCT
+776    GAAGATCAGCAGCCACGAGCAGGCCCCTGGCCGACTGCCGCGCCCTGGAGCTGGACCGGCAGTCTGTGAAGGC
```
Exon 2
```
+851    GCACTTCTCCTGGGGCAGTGCCAGCTGGAGATGCCAATCGCCAATCGCCAGCGGAGgttg
+926    gctgacaagctgccgtttgtgggcctctgggggcaggcggggtggactggccagagagagtgacgtgaagccccg
+1001   ttcccagcCTTACAGCCTGGCCAAGGAGCAGCCGTGAACTTCGGGACGACATCCCCAGCGCTCTTCGAATCGC
```
Exon 3A
```
+1076   GAAGAAGAGGCGCTGGAACAGCATTGAGGAGCGGCATCCACCAGGAGCGAGCTGCACTCCTACCTCTCCAG
+1151   GCTCATTGCCGCCGAGCGTGAGAGgtgggaccctcaccccaggccgccctgtcttggataattctgaatcaccg
```
Exon 3B
```
+1226   actcccgacacaagcgttatcgaaggcttactgcaagcaggaaatgtgggaagtgtggatgttagctctga
+1301   gattggggtgtggtcagacatctctggccaggtccatctctgaccccagGGAGCTGGAAGA
```
Exon 3C
```
+1376   GTGCCAGCGAAACCACGAGGGTGATGAGGACGACAGCCACGTCCCGGCCCTGCATTGAGGCCAAGCA
```

Fig. 11C

```
+1451  Cgtgagggtgcccccaccacatgtgggtctgtgtgttgtgcacgtgtgcgtgggagcatccccgccttgtgttgg
       Exon 3D
+1526  gtctgtgcccatggaggaggaggtggggtgtctccccaagcacagcactcaactctttcacagGACAAGTACA
       Exon 3E
+1601  TGGCGGACATGGACGAGCTTTTTCTCAGGTGGATGAGAGAGGAAGgtgagtgtgtgtcgttgctgccgatgg
+1676  ctggcaggtgctcgtgcagtgccccttcagcctctgaccgtgtgccctgtgccacagAAGCGAGACATCCCC
+1751  GACTACCTGTGTGTGGCAAGATCAGCTTTGAGCTGAACGCCGTGCATCACGCCCAGTGGCATCACCTACGAC
       Exon 4
+1826  CGCAAGGACATCGAGGAGCACCTGCAGgtgagctgcgggctgcggggagcaggcagtggcatggtcctgggcc
+1901  ccatgactgccctctgccctcttgtcactgcagCGTGTGGGTCATTTTGACCCGTGACCCGAGCCCCCTGAC
+1976  CCAGGAACAGCTCATCCCCAACTTGGCTATGAAGGAGGTTATTGACGCATTCATCTCTGAGAATGCTGGGTGGA
       Exon 5
+2051  GGACTACTGAGGTTCCCTGCCCTACCTGGCGTCCTGGTCCGTCCTGGTCCAGGGGAGCCCTGGCAGAAGCCCCCGGCCCCTATA
+2126  CATAGTTTATGTTCCTGGCCACCCCGACCGCTTCCCCAAGTTCTGCTGTTGGACTCTGGACTGTTCCCCTCTC
+2201  AGCATCGCTTTGCTGGGCCGTGATCGTCCCCCTTTGTGGGCTGGAAAAGCAGTGAGGGTGAGGGCTGGGCTGAGG
```

*Fig. 11D*

```
+2276  CCATTGCCGCCACTATCTGTGTAATAAAATCCGTGAGCACGAGGTGGGACGTGCTGGTGTGTGacggcagtcct
       gccagctgttttggctagccgaggaaggtggagatgaagacgctggtgtcaagttgagcgtagcatgccaccag
+2426  cggtcggggaagtacagcacctgtgtgaggaaggggtgcagcagagattagctgcgggcctctagcctggcctg
       gccctctcctgccagccactgaccctgcccgttttggtcagcgagtccaaccccaaccccgtgctgaccttac
+2576  tgagcagcagtgtcaccttctgagtaccccggtccatgccagtgccagacagaagcctcagtcctcctgtggggttat
       gaccgtagatcacttctgagtaccccggtccatgccagtgccagacagaagcctcagtcctccaagaagcaccac
+2726  gagcacctggtgaccaacccattttgtactcaccgacagcaggccaaatggggtggggagtagtgccgaaagagag
       ctgcgattccaaagctgtaagctggagcggttcccgaagaagtacaccgcgcctcaacagagacgcgggacaggatc
+2876  aggcccactcggtgaagttgttgtccccaagcgtcccaccccctaggggtgtctgccaacagagacgcgggacaggagtg
       ctggcacctggagactccaagcgctgctccagcagctgctcactgcaagtccactgcaggaagggcaagtccaggaggtcagg
+3026  gggtcctggggtgcagccgccccggtcccagcccccgtgttggcaaatgggcgggcccccaggggtgaggccgtacctttgtggtagg
       accgtctggttccagcgccccggtgttggcaaatgggcgggcccccaggggtgaggccgtacctttgtgtagg
+3176  agtaggtgttggccggtgctcagccggccagccggaccactctgtccccaaacgaaccagcaaccagcaagcaacctgtcgcgggagcac
```

*Fig. 11ε*

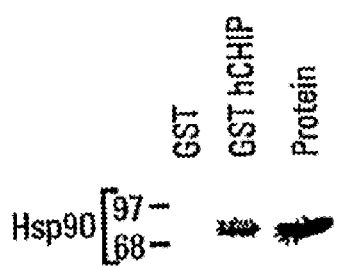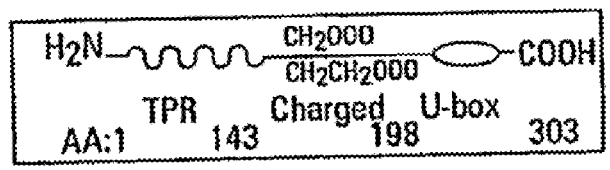
*Fig. 13A*
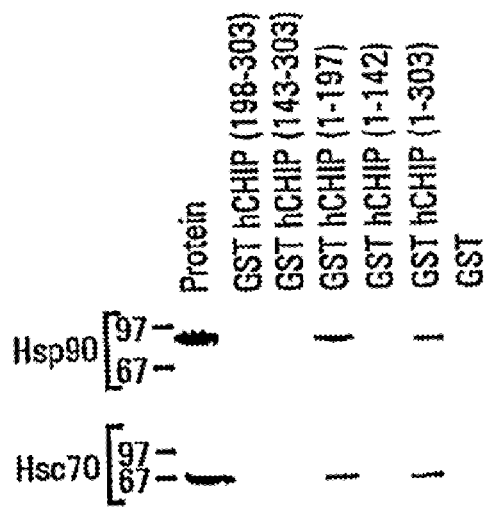
*Fig. 13B*
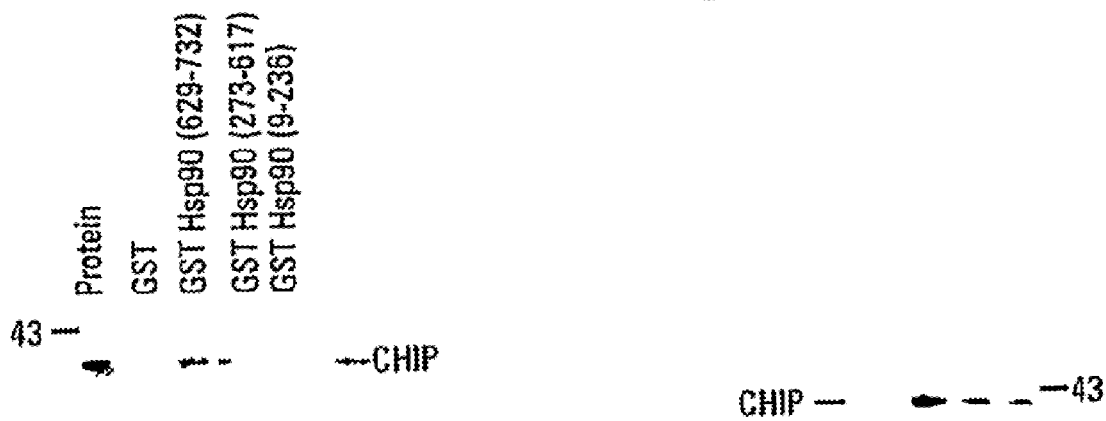
*Fig. 13C*
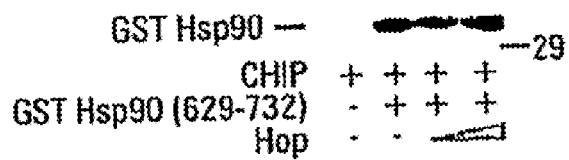
*Fig. 13D*